United States Patent [19]

Okamoto et al.

[11] 4,097,591

[45] * Jun. 27, 1978

[54] $N^2$-ARYLSULFONYL-L-ARGININAMIDES AND THE PHARMACEUTICALLY ACCEPTABLE SALTS THEREOF

[75] Inventors: Shosuke Okamoto, Akiko Hijikata, both of Kobe; Ryoji Kikumoto, Machida; Yoshikuni Tamao, Yokohama; Kazuo Ohkubo, Machida; Tohru Tezuka, Yokohama; Shinji Tonomura, Tokyo, all of Japan

[73] Assignees: Mitsubishi Chemical Industries Limited, Tokyo; Shosuke Okamoto, both of Japan

[ * ] Notice: The portion of the term of this patent subsequent to Jan. 3, 1995, has been disclaimed.

[21] Appl. No.: 776,195

[22] Filed: Mar. 10, 1977

Related U.S. Application Data

[60] Continuation-in-part of Ser. No. 760,677, Jan. 19, 1977, which is a continuation-in-part of Ser. No. 638,985, Dec. 9, 1975, Pat. No. 4,055,636, Ser. No. 646,522, Jan. 5, 1976, Pat. No. 4,018,915, Ser. No. 649,219, Jan. 14, 1976, Pat. No. 4,018,913, Ser. No. 656,014, Feb. 6, 1976, Pat. No. 4,041,156, Ser. No. 656,870, Feb. 10, 1976, Pat. No. 4,046,876, Ser. No. 669,743, Mar. 24, 1976, Pat. No. 4,070,457, Ser. No. 671,436, Mar. 29, 1976, Pat. No. 4,066,758, and Ser. No. 703,704, Jul. 8, 1976, Pat. No. 4,069,323, said Ser. No. 671,436, is a division of Ser. No. 622,390, Oct. 14, 1975, abandoned.

[51] Int. Cl.[2] .................... A61K 37/00; C07C 103/52

[52] U.S. Cl. ............................ 424/177; 260/112.5 R; 260/293.56; 260/501.7; 260/518 R; 260/518 A; 260/501.11; 260/516; 260/519; 260/544 B; 260/293.62; 260/501.14; 260/501.18; 260/501.2; 424/309; 424/310; 424/316; 260/544 S

[58] Field of Search .................... 260/112.5 R, 293.56, 260/501.1, 518, 501.11, 516, 544, 293.62, 501.14, 501.18, 501.2, 556; 424/177, 309, 310, 316, 319, 321, 390, 298; 560/115, 121, 10, 13, 123, 124, 125

[56] References Cited

U.S. PATENT DOCUMENTS

| | | | |
|---|---|---|---|
| 3,131,174 | 4/1964 | Schwyzer | 260/112.5 R |
| 4,018,913 | 4/1977 | Okamoto et al. | 260/112.5 R |
| 4,018,915 | 4/1977 | Okamoto et al. | 260/112.5 R |
| 4,036,955 | 7/1977 | Okamoto et al. | 260/112.5 R |
| 4,036,955 | 7/1977 | Okamoto et al. | 424/177 |

*Primary Examiner*—Delbert R. Phillips
*Attorney, Agent, or Firm*—Oblon, Fisher, Spivak, McClelland & Maier

[57] ABSTRACT

$N^2$-arylsulfonyl-L-argininamides and the pharmaceutically acceptable salts thereof have been found to be effective as pharmaceutical agents for the inhibition and suppression of thrombosis in mammals.

3 Claims, No Drawings

$N^2$-ARYLSULFONYL-L-ARGININAMIDES AND THE PHARMACEUTICALLY ACCEPTABLE SALTS THEREOF

CROSS-REFERENCE TO RELATED APPLICATIONS

This application is a continuation-in-part of application Ser. No. 760,672 filed Jan. 19, 1977 which in turn is a continuation-in-part of the following prior filed applications:

Ser. No. 638,985 of Dec. 9, 1975-U.S. Pat. No. 4,055,636

Ser. No. 646,522 of Jan. 5, 1976-U.S. Pat. No. 4,018,915

Ser. No. 649,219 of Jan. 14, 1976-U.S. Pat. No. 4,018,913

Ser. No. 656,014 of Feb. 6, 1976-U.S. Pat. No. 4,041,156

Ser. No. 656,870 of Feb. 10, 1976-U.S. Pat. No. 4,046,876

Ser. No. 669,743 of Mar. 24, 1976-U.S. Pat. No. 4,070,457

Ser. No. 671,436 of Mar. 29, 1976-U.S. Pat. No. 4,066,758

Ser. No. 703,704 of Jul. 8, 1976-U.S. Pat. No. 4,069,323

Application Ser. No. 671,436 in turn is a division of application of Ser. No. 622,390 filed Oct. 14, 1975 now abandoned.

BACKGROUND OF THE INVENTION

1. Field of the Invention

This invention relates to the discovery of certain new and useful $N^2$-arylsulfonyl-L-argininamides and the pharmaceutically acceptable salts thereof, which are of especial value in view of their outstanding antithrombotic properties and low toxicities.

2. Description of the Prior Art

In the past, there have been many attempts to obtain new and improved agents for the treatment of thrombosis. The $N^2$-(p-tolysulfonyl)-L-arginine esters have been found to be one type of agent which can be used and these have been found to be effective in dissolving blood clots. (U.S. Pat. No. 3,622,615, issued Nov. 23, 1971). One family of compounds which have been found to be particularly useful as highly specific inhibitors of thrombin for the control of thrombosis is the $N^2$-dansyl-L-arginine ester or amide. (Our pending U.S. Application Ser. No. 496,939, filed Aug. 13, 1974 now U.S. Pat. No. 3,978,045). However, there is a continuing need for a highly specific inhibitor of thrombin for the control of thrombosis, which exhibits lower toxicity.

SUMMARY OF THE INVENTION

It has now been discovered that $N^2$-arylsulfonyl-L-argininamides exhibit antithrombotic activity and even lower toxicity levels at the same relative potencies, as compared with the $N^2$-dansyl-L-arginine ester or amide. An $N^2$-arylsulfonyl-L-argininamide having the formula (I):

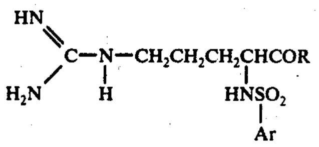
(I)

or a pharmaceutically acceptable salt thereof, wherein R is

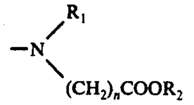
(1)

wherein $R_1$ is $C_2$-$C_{10}$ alkyl, $C_3$-$C_{10}$ alkenyl, $C_3$-$C_{10}$ alkynyl, $C_2$-$C_{10}$ alkoxyalkyl, $C_2$-$C_{10}$ alkylthioalkyl, $C_2$-$C_{10}$ alkylsulfinylalkyl, $C_1$-$C_{10}$ hydroxyalkyl, $C_2$-$C_{10}$ carboxyalkyl, $C_3$-$C_{10}$ alkoxycarbonylalkyl, $C_1$-$C_{10}$ haloalkyl, $C_7$-$C_{15}$ aralkyl, $C_8$-$C_{15}$ $\alpha$-carboxyaralkyl, $C_3$-$C_{10}$ cycloalkyl or $C_4$-$C_{10}$ cycloalkylalkyl; $R_2$ is hydrogen, $C_1$-$C_{10}$ alkyl, $C_6$-$C_{10}$ aryl, $C_7$-$C_{12}$ aralkyl or 5-indanyl; and *n* is an integer of 1, 2 or 3; or

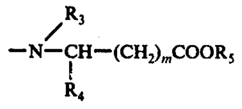
(2)

wherein $R_3$ is hydrogen, $C_1$-$C_{10}$ alkyl, $C_3$-$C_{10}$ alkenyl, $C_3$-$C_{10}$ alkynyl, $C_2$-$C_{10}$ alkoxyalkyl, $C_2$-$C_{10}$ alkylthioalkyl, $C_2$-$C_{10}$ alkylsulfinylalkyl, $C_1$-$C_{10}$ hydroxyalkyl, $C_2$-$C_{10}$ carboxyalkyl, $C_3$-$C_{10}$ alkoxycarbonylalkyl, $C_1$-$C_{10}$ haloalkyl, $C_7$-$C_{15}$ aralkyl, $C_8$-$C_{15}$ $\alpha$-carboxyaralkyl, $C_3$-$C_{10}$ cycloalkyl or $C_4$-$C_{10}$ cycloalkyloalkyl; $R_4$ is $C_1$-$C_5$ alkyl, carboxy, $C_2$-$C_{10}$ alkoxycarbonyl, phenyl, $C_7$-$C_{12}$ aralkyl or ring substituted benzyl wherein said substituent is $C_1$-$C_5$ alkyl or $C_1$-$C_5$ alkoxy; $R_5$ is hydrogen, $C_1$-$C_{10}$ alkyl, $C_6$-$C_{10}$ aryl, $C_7$-$C_{12}$ aralkyl or 5-indanyl; and *m* is an integer of 0, 1 or 2;

Ar is a phenyl or naphthyl group, either substituted with at least one substituent selected from the group consisting of sulfoamino, carbamoyl, $C_3$-$C_{10}$ N,N-dialkylcarboamoyl, amino, $C_1$-$C_{10}$ alkylamino, mercapto, $C_1$-$C_{10}$ alkylthio, $C_7$-$C_{12}$ aralkyl, carboxy, $C_2$-$C_{10}$ alkoxycarbonyl, $C_2$-$C_{10}$ carboxyalkyl, $C_1$-$C_{10}$ acylamino, $C_2$-$C_{10}$ alkylcarbonyl, $C_1$-$C_{10}$ hydroxyalkyl, $C_1$-$C_{10}$ haloalkyl and phenyl optionally substituted with at least one hydroxy, $C_1$-$C_5$ alkoxy, or mixtures thereof; a phenyl or naphthyl group, either substituted with at least one substituent selected from the group consisting of sulfoamino, carbamoyl, $C_3$-$C_{10}$ N,N-dialkylcarbamoyl, amino, $C_1$-$C_{10}$ alkylamino, mercapto, $C_1$-$C_{10}$ alkylthio, $C_7$-$C_{12}$ aralkyl, carboxy, $C_2$-$C_{10}$ alkoxycarbonyl, $C_2$-$C_{10}$ carboxyalkyl, $C_1$-$C_{10}$ acylamino, $C_2$-$C_{10}$ alkylcarbonyl, $C_1$-$C_{10}$ hydroxyalkyl, $C_1$-$C_{10}$ haloalkyl and phenyl optionally substituted with at least one hydroxy, $C_1$-$C_5$ alkoxy, or mixtures thereof, and at least one substituent selected from the group consisting of halo, nitro, cyano, hydroxy, $C_1$-$C_{10}$ alkyl, $C_1$-$C_{10}$ alkoxy and $C_2$-$C_{20}$ dialkylamino;

an oxanthrenyl or dibenzofuranyl group substituted with at least one substituent selected from the group consisting of halo, nitro, cyano, hydroxy, $C_1$-$C_{10}$ alkyl, $C_1$-$C_{10}$ alkoxy, $C_2$-$C_{20}$ dialkylamino, sulfoamino, carbamoyl, $C_3$-$C_{10}$ N,N-dialkylcarbamoyl, amino, $C_1$-$C_{10}$ alkylamino, mercapto, $C_1$-$C_{10}$ alkylthio, $C_7$-$C_{12}$ aralkyl, carboxyl, $C_2$-$C_{10}$ alkoxycarbonyl, $C_2$-$C_{10}$ carboxyalkyl, $C_1$-$C_{10}$ acylamino, $C_2$-$C_{10}$ alkylcarbonyl, $C_1$-$C_{10}$ hydroxyalkyl, $C_1$-$C_{10}$ haloalkyl, and phenyl optionally substituted with at least one hydroxy, $C_1$-$C_5$ alkoxy, or mixtures thereof;

a $C_7$-$C_{12}$ aralkyl, tetrahydronaphthyl, 1, 2-ethylenedioxyphenyl, chromanyl, 2, 3-ethylenedioxynaphthyl or xanthenyl group, any substituted with at least one substituent selected from the group consisting of halo, nitro, cyano, hydroxy, $C_1$-$C_{10}$ alkyl, $C_1$-$C_{10}$ alkoxy, $C_2$-$C_{20}$ dialkylamino, sulfoamino, carbamoyl, $C_3$-$C_{10}$ N,N-dialkylcarbamoyl, amino, $C_1$-$C_{10}$ alkylamino, mercapto, $C_1$-$C_{10}$ alkylthio, $C_7$-$C_{12}$ aralkyl, carboxyl, $C_2$-$C_{10}$ alkoxycarbonyl, $C_2$-$C_{10}$ carboxyalkyl, $C_1$-$C_{10}$ acylamino, $C_2$-$C_{10}$ alkylcarbonyl, $C_1$-$C_{10}$ hydroxyalkyl, $C_1$-$C_{10}$ haloalkyl, oxo and phenyl optionally substituted with at least one hydroxy, $C_1$-$C_5$ alkoxy, or mixtures thereof;

a naphthoquinonyl, anthryl, phenanthryl, pentalenyl, heptalenyl, azulenyl, biphenylenyl, as -indacenyl, S-indacenyl, acenaphthylenyl, phenylcarbonylphenyl, phenoxyphenyl, benzofuranyl, isobenzofuranyl, benzo (b) thienyl, isobenzothienyl, thianthrenyl, dibenzothienyl, phenoxathiinyl, indolyl, 1H-indazolyl, quinolyl, isoquinolyl, phthalazinyl, 1,8-naphthyridinyl, quinoxalinyl, quinazolinyl, cinnolinyl, carbazolyl, acridinyl, phenazinyl, phenothiazinyl, phenoxazinyl or benzimidazolyl group any of which is unsubstituted or substituted with one or more groups selected from the group consisting of halo, nitro, cyano, hydroxy, $C_1$-$C_{10}$ alkyl, $C_1$-$C_{10}$ alkoxy, $C_2$-$C_{20}$ dialkylamino, sulfoamino, carbamoyl, $C_3$-$C_{10}$ N,N-dialkylcarbamoyl, amino, $C_1$-$C_{10}$ alkylamino, mercapto, $C_1$-$C_{10}$ alkylthio, $C_7$-$C_{12}$ aralkyl, carboxyl, $C_2$-$C_{10}$ alkoxycarbonyl, $C_2$-$C_{10}$ carboxyalkyl, $C_1$-$C_{10}$ acylamino, $C_2$-$C_{10}$ alkylcarbonyl, $C_1$-$C_{10}$ hydroxyalkyl, $C_1$-$C_{10}$ haloalkyl and phenyl optionally substituted with at least one hydroxy, $C_1$-$C_5$ alkoxy, or mixtures thereof; a $C_9$-$C_{16}$ cycloalkylphenyl, $C_{10}$-$C_{18}$ cycloalkylalkylphenyl, $C_9$-$C_{16}$ cycloalkyloxyphenyl, $C_9$-$C_{16}$ cycloalkylthiophenyl, 9,10-dihydroanthryl, 5,6,7,8-tetrahydroanthryl, 9,10-dihydrophenanthryl, 1,2,3,4,5,6,7,8-octahydrophenanthryl, indenyl, indanyl, fluorenyl, acenaphthenyl, phenylthiophenyl, isochromanyl, 2,3-dihydrobenzofuranyl, 1,3-dihydroisobenzofuranyl, thioxanthenyl, 2H-chromenyl, 3,4-dehydro-1-isochromanyl, 4H-chromenyl, indolinyl, isoindolinyl, 1,2,3,4-tetrahydroquinolyl or 1,2,3,4-tetrahydroisoquinolyl group any of which is unsubstituted or substituted with one or more groups selected from the group consisting of halo, nitro, cyano, hydroxy, $C_1$-$C_{10}$ alkyl, $C_1$-$C_{10}$ alkoxy, $C_2$-$C_{20}$ dialkylamino, sulfoamino, carbamoyl, $C_3$-$C_{10}$ N,N-dialkylcarbamoyl, amino, $C_1$-$C_{10}$ alkylamino, mercapto, $C_1$-$C_{10}$ alkylthio, $C_7$-$C_{12}$ aralkyl, carboxyl, $C_2$-$C_{10}$ alkoxycarbonyl, $C_2$-$C_{10}$ carboxyalkyl, $C_1$-$C_{10}$ acylamino, $C_2$-$C_{10}$ alkylcarbonyl, $C_1$-$C_{10}$ hydroxyalkyl, $C_1$-$C_{10}$ haloalkyl, oxo and phenyl optionally substituted with at least one hydroxy, $C_1$-$C_5$ alkoxy, or mixtures thereof; or benzene ring-substituted

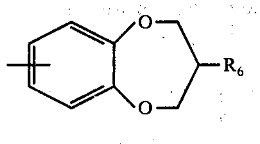

wherein $R_6$ is hydrogen, $C_1$-$C_{10}$ alkyl or $C_1$-$C_{10}$ alkoxy, and said substituent is at least one $C_1$-$C_5$ alkyl, $C_1$-$C_5$ alkoxy or mixtures thereof.

Also encompassed within this invention are pharmaceutically acceptable salts thereof.

This invention also relates to a method for inhibiting activity and suppressing activation of thrombin in vivo in mammals which comprises administering to a mammal a pharmaceutically (antithrombotically) effective amount of an $N^2$-arylsulfonyl-L-argininamide or the pharmaceutically acceptable salts thereof.

DETAILED DESCRIPTION OF THE PREFERRED EMBODIMENTS

This invention relates to a group of $N^2$-arylsulfonyl-L-argininamides of the formula (I):

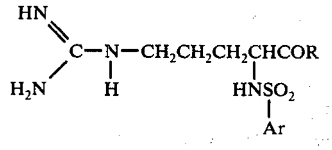

(I)

wherein R is selected from the group consisting of

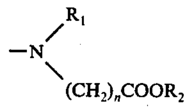

(I)

wherein $R_1$ is selected from the group consisting of $C_2$-$C_{10}$ alkyl, such as ethyl, propyl, butyl, isobutyl, pentyl, hexyl, octyl, decyl or the like, alkenyl or 3-10 (preferably 3-6) carbon atoms, such as allyl, 2-butenyl, 3-butenyl, 2-pentenyl or the like, alkynyl of 3-10 (preferably 3-6) carbon atoms, such as 2-propynyl, 2-butynyl, 3-butynyl or the like, alkoxyalkyl of 2-10 (preferably 2-6) carbon atoms, such as methoxymethyl, ethoxymethyl, propoxymethyl, 2-methoxyethyl, 2-ethoxyethyl, 2-propoxyethyl, 2-methoxypropyl, 3-methoxypropyl, 3-ethoxypropyl, 3-propoxypropyl, 4-methoxybutyl, 4-ethoxybutyl, 4-butoxybutyl, 5-butoxypentyl or the like, alkylthioalkyl of 2-10 (preferably 2-6) carbon atoms, such as methylthiomethyl, ethylthiomethyl, propylthiomethyl, 2-methylthioethyl, 2-ethylthioethyl, 2-propylthioethyl, 3-methylthiopropyl, 2-methylthiopropyl, 3-ethylthiopropyl, 3-propylthiopropyl, 4-methylthiobutyl, 4-ethylthiobutyl, 4-butylthiobutyl, 5-butylthiopentyl or the like, alkylsulfinylalkyl of 2-10 (preferably 2-6) carbon atoms, such as methylsulfinylmethyl, ethylsulfinylmethyl, propylsulfinylmethyl, 2-methylsulfinylethyl, 2-ethylsulfinylethyl, 2-propylsulfinylethyl, 3-methylsulfinylpropyl, 3-ethylsulfinylpropyl or the like, hydroxyalkyl of 1-10 (preferably 1-6) carbon atoms, such as hydroxymethyl, 2-hydroxyethyl, 3-hydroxypropyl, 2-hydroxypropyl, 4-hydroxybutyl, 3-hydroxybutyl, 5-hydroxypentyl or the like, carboxyalkyl of 2-10 (perferably 2-7) carbon atoms, such as carboxymethyl, 2-carboxyethyl, 2-carboxypropyl, 3-carboxypropyl, 1-carboxybutyl, 2-carboxybutyl, 4-carboxybutyl or the like, alkoxycarbonylalkyl of 3-10 (preferably 3-8) carbon atoms, such as methoxycarbonylmethyl, 2-ethoxycarbonylethyl, 2-ethoxycarbonylpropyl, 3-methoxycarbonylpropyl, 1-methoxycarbonylbutyl, 2-ethoxycarbonylbutyl, 4-methoxycarbonylbutyl or the like, alkylcarbonylalkyl of 3 to 10 carbon atoms such as methylcarbonylethyl or the like, haloalkyl of 1-10 (preferably 1-5) carbon atoms such as chloromethyl, 2-chloroethyl, 2-bromoethyl, 2-chloropropyl, 3-chloropropyl, 2-chlorobutyl, 4-chlorobutyl or the like, aralkyl of 7-15 (preferably 7-10) carbon atoms, such as benzyl, phenethyl, 3-phenylpropyl, 4-phenylbutyl, 6-phenylhexyl, 1-phenylethyl, 2-phenylpropyl or the like, $\alpha$-carboxyaralkyl of 8-15 (preferably 8-12) carbon atoms, such as $\alpha$-carboxybenzyl, $\alpha$-carboxyphenethyl or the like, $C_3$-$C_{10}$ cycloalkyl, such as cyclopropyl, cyclobutyl, cyclopentyl, cyclohexyl, cycloheptyl, cyclooctyl, cyclononyl or cyclodecyl, $C_4$-$C_{10}$ cycloalkylalkyl, such as cyclopropylmethyl, cyclopentylmethyl, cyclohexylmethyl, 2-cyclohexylethyl, cyclooctylmethyl or the like; $R_2$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, or 5-indanyl; and $n$ is an integer of 1, 2 or 3, and

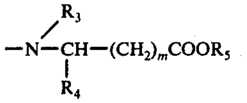
(2)

wherein $R_3$ is selected from the group consisting of hydrogen, $C_1$-$C_{10}$ alkyl, such as methyl, ethyl, propyl, butyl, isobutyl, pentyl, hexyl, octyl, decyl or the like, alkenyl of 3-10 (preferably 3-6) carbon atoms, such as allyl, 2-butenyl, 3-butenyl, 2-pentenyl or the like, alkynyl of 3-10 (preferably 3-6) carbon atoms, such as 2-propynyl, 2butynyl, 3-butynyl or the like, alkoxyalkyl of 2-10 (preferably 2-6) carbon atoms, such as methoxymethyl, ethoxymethyl, propoxymethyl, 2-methoxyethyl, 2-ethoxyethyl, 2-propoxyethyl, 2-methoxypropyl, 3-methoxypropyl, 3-ethoxypropyl, 3-propoxypropyl, 4-methoxybutyl, 4-ethoxybutyl, 4-butoxybutyl, 5-butoxypentyl or the like, alkylthioalkyl of 2-10 (preferably 2-6) carbon atoms, such as methylthiomethyl, ethylthiomethyl, propylthiomethyl, 2-methylthioethyl, 2-ethylthioethyl, 2-propylthioethyl, 3-methylthiopropyl, 2-methylthiopropyl, 3-ethylthiopropyl, 3-propylthiopropyl, 4-methylthiobutyl, 4-ethylthiobutyl, 4-butylthiobutyl, 5-butylthiopentyl or the like, alkylsulfinylalkyl of 2-10 (preferably 2-6) carbon atoms, such as methylsulfinylmethyl, ethylsulfinylmethyl, propylsulfinylmethyl, 2-methylsulfinylethyl, 2-ethylsulfinylethyl, 2-propylsulfinylethyl, 3-methylsulfinylpropyl, 3-ethylsulfinylpropyl or the like, hydroxyalkyl of 1-10 (preferably 1-6) carbon atoms, such as hydroxymethyl, 2-hydroxyethyl, 3-hydroxypropyl, 2-hydroxypropyl, 4-hydroxybutyl, 3-hydroxybutyl, 5-hydroxypentyl or the like, carboxyalkyl of 2-10 (preferably 2-7) carbon atoms, such as carboxymethyl, 2-carboxyethyl, 2-carboxypropyl, 3-carboxypropyl, 1-carboxybutyl, 2-carboxybutyl, 4-carboxybutyl or the like, alkoxycarbonylalkyl of 3-10 (preferably 3-8) carbon atoms, such as methoxycarbonylmethyl, 2-methoxycarbonylethyl, 2-ethoxycarbonylpropyl, 3-methoxycarbonylpropyl, 1-methoxycarbonylbutyl, 2-ethoxycarbonylbutyl, 4-methoxycarbonylbutyl or the like, alkylcarbonylalkyl of 3 to 10 carbon atoms such as methylcarbonylethyl or the like, haloalkyl of 1-10 (preferably 1-5) carbon atoms such as chloromethyl, 2-chloroethyl, 2-bromoethyl, 2-chloropropyl, 3-chloropropyl, 2-chlorobutyl, 4-chlorobutyl or the like, aralkyl of 7-15 (preferably 7-10) carbon atoms, such as benzyl, phenethyl, 3-phenylpropyl, 4-phenylbutyl, 6-phenylhexyl, 1-phenylethyl, 2-phenylpropyl or the like, $\alpha$-carboxyaralkyl of 8-15 (preferably 8-12) carbon atoms, such as $\alpha$-carboxybenzyl, $\alpha$-carboxyphenethyl or the like, $C_3$-$C_{10}$ cycloalkyl, such as cyclopropyl, cyclobutyl, cyclopentyl, cyclohexyl, cycloheptyl, cyclooctyl, cyclononyl or cyclodecyl, $C_4$-$C_{10}$ cycloalkylalkyl, such as cyclopropylmethyl, cyclopentylmethyl, cyclohexylmethyl, 2-cyclohexylethyl, cyclooctylmethyl or the like; $R_4$ is selected from the group consisting of alkyl of 1-5 carbon atoms, such as methyl, ethyl, propyl, isopropyl, butyl, isobutyl, sec-butyl, pentyl or the like, carboxy, alkoxycarbonyl of 2-10 (preferably 2-5) carbon atoms, such as methoxycarbonyl, ethoxycarbonyl, propoxycarbonyl or the like, phenyl, aralkyl of 7-12 (preferably 7-10) carbon atoms, such as benzyl, phenethyl or the like, and ring substituted benzyl wherein said substituent is alkyl of 1-5(preferably 1-3) carbon atoms, such as methyl, ethyl, propyl, or isopropyl, or alkoxy of 1-5 (preferably 1-3) carbon atoms, such as methoxy, ethoxy, propoxy or isopropoxy; $R_5$ is selected from the group consisting of hydrogen, $C_1$-$C_{10}$ alkyl, such as methyl, ethyl, propyl, butyl, tert-butyl, hexyl, octyl, decyl or the like, $C_6$-$C_{10}$ aryl, such as phenyl, m-tolyl, naphthyl or the like, aralkyl of 7-12 (preferably 7-10) carbon atoms, such as benzyl, phenethyl or the like, and 5-indanyl; and m is an integer of 0, 1 or 2; and Ar is a phenyl or naphthyl group, either substituted with one or more groups selected from the group consisting of sulfoamino, carbamoyl, N,N-dialkylcarbamoyl of 3-10 (preferably 3-7) carbon atoms, such as N,N-dimethylcarbamoyl, N,N-diethylcarbamoyl or the like, amino, alkylamino of 1-10 (preferably 1-5) carbon atoms, such as methylamino, ethylamino, propylamino, butylamino or the like, mercapto, alkylthio of 1-10 (preferably 1-5) carbon atoms, such as methylthio, ethylthio, propylthio, butylthio or the like, aralkyl of 7-12 (preferably 7-10) carbon atoms, such as benzyl, phenethyl or the like, carboxyl, alkoxycarbonyl of 2-10 (preferably 2-6) carbon atoms, such as methoxycarbonyl, ethoxycarbonyl or the like, carboxyalkyl of 2-10 (preferably 2-6) carbon atoms, such as carboxymethyl, 2-carboxyethyl, 2-carboxypropyl or the like, acylamino such as alkylcarbonylamino of 1-10 (preferably 1-5) carbon atoms, such as acetylamino, propionylamino or the like, alkylcarbonyl of 2-10 (preferably 2-6) carbon atoms, such as acetyl, propionyl or the like, hydroxyalkyl of 1-10 (preferably 1-5) carbon atoms, such as hydroxymethyl, 2-hydroxyethyl, 2-hydroxypropyl or the like, haloalkyl of 1-10 (preferably 1-5) carbon atoms, such as chloromethyl, trifluoromethyl, bromomethyl, 2-chloroethyl or the like, and phenyl optionally substituted with at least one hydroxy and/or $C_1$-$C_5$ alkoxy, such as methoxy, ethoxy, propoxy, butoxy or the like;

a phenyl or naphthyl group either substituted with one or more groups selected from the group consisting of sulfoamino, carbamoyl, N,N-dialkylcarbamoyl of 3-10 (preferably 3-7) carbon atoms, such as N,N-dimethylcarbamoyl, N,N-diethylcarbamoyl or the like, amino, alkylamino of 1-10 (preferably 1-5) carbon atoms, such as methylamino, ethylamino, propylamino, butylamino or the like, mercapto, alkylthio of 1-10 (preferably 1-5) carbon atoms, such as methylthio, ethylthio, propylthio, butylthio or the like, aralkyl of 7-12 (preferably 7-10) carbon atoms, such as benzyl, phenethyl or the like, carboxyl, alkoxycarbonyl of 2-10 (preferably 2-6) carbon atoms, such as methoxycarbonyl, ethoxycarbonyl or the like, carboxyalkyl of 2-10 (preferably 2-6) carbon atoms, such as carboxymethyl, 2-carboxyethyl, 2-carboxypropyl or the like, acylamino such as alkylcarbonylamino of 1-10 (preferably 1-5) carbon atoms, such as acetylamino, propionylamino or the like, alkylcarbonyl of 2-10 (preferably 2-6) carbon atoms, such as acetyl, propionyl or the like, hydroxyalkyl of 1-10 (preferably 1-5) carbon atoms, such as hydroxymethyl, 2-hydroxyethyl, 2-hydroxypropyl or the like, haloalkyl of 1-10 (preferably 1-5) carbon atoms, such as chloromethyl, trifluoromethyl, bromomethyl, 2-chloroethyl or the like, and phenyl optionally substituted with at least one hydroxy and/or $C_1$-$C_5$ alkoxy, such as methoxy, ethoxy, propoxy, butoxy or the like, and one or more groups selected from the group consisting of halo, nitro, cyano, hydroxy, alkyl of 1-10 (preferably 1-5) carbon atoms, such as methyl, ethyl, propyl, butyl or the like, alkoxy of 1-10 (preferably 1-5) carbon atoms, such as methoxy, ethoxy, propoxy, butoxy or the like, dialkylamino of 2-20 (preferably 2-10) carbon atoms, such as dimethylamino, diethylamino, dipropylamino or the like;

an oxanthrenyl or dibenzofuranyl group substituted with one or more groups selected from the group consisting of halo, nitro, cyano, hydroxy, alkyl of 1-10 (preferably 1-5) carbon atoms, such as methyl, ethyl, propyl, butyl or the like, alkoxy of 1-10 (preferably 1-5) carbon atoms, such as methoxy, ethoxy, propoxy, butoxy or the like, dialkylamino of 2-20 (preferably 2-10) carbon atoms, such as dimethylamino, diethylamino, dipropylamino or the like, sulfoamino, carbamoyl, N,N-dialkylcarbamoyl of 3-10 (preferably 3-7) carbon atoms, such as N,N-dimethylcarbamoyl, N,N-diethylcarbamoyl or the like, amino, alkylamino of 1-10 (preferably 1-5) carbon atoms, such as methylamino or the like, mercapto, alkylthio of 1-10 (preferably 1-5) carbon atoms, such as methylthio, ethylthio, propylthio, butylthio or the like, aralkyl of 7-12 (preferably 7-10) carbon atoms, such as benzyl, phenethyl or the like, carboxyl, alkoxycarbonyl of 2-10 (preferably 2-6) carbon atoms, such as methoxycarbonyl, ethoxycarbonyl or the like, carboxyalkyl of 2-10 (preferably 2-6) carbon atoms, such as carboxymethyl, 2-carboxyethyl, 2-carboxypropyl or the like, acylamino such as alkylcarbonylamino of 1-10 (preferably 1-5) carbon atoms, such as acetylamino, propionylamino or the like, alkylcarbonyl of 2-10 (preferably 2-6) carbon atoms, such as acetyl, propionyl, or the like, hydroxyalkyl of 1-10 (preferably 1-5) carbon atoms, such as hydroxymethyl, 2-hydroxyethyl, 2-hydroxypropyl or the like, haloalkyl of 1-10 (preferably 1-5) carbon atoms, such as chloromethyl, trifluoromethyl, bromomethyl, 2-chloroethyl or the like, and phenyl optionally substituted with at least one hydroxy and/or $C_1$-$C_5$ alkoxy, such as methoxy, ethoxy, propoxy, butoxy or the like;

a $C_7$-$C_{12}$ aralkyl, tetrahydronaphthyl, 1,2-ethylenedioxyphenyl, chromanyl, 2,3-ethylenedioxynaphthyl or xanthenyl group, any substituted with one or more groups selected from the group consisting of halo, nitro, cyano, hydroxy, alkyl of 1-10 (preferably 1-5) carbon atoms, such as methyl, ethyl, propyl, butyl or the like, alkoxy of 1-10 (preferably 1-5) carbon atoms, such as methoxy, ethoxy, propoxy, butoxy or the like, dialkylamino of 2-20 (preferably 2-10) carbon atoms, such as dimethylamino, diethylamino, dipropylamino or the like, sulfoamino, carbamoyl, N,N-dialkylcarbamoyl of 3-10 (preferably 3-7) carbon atoms, such as N,N-dimethylcarbamoyl, N,N-diethylcarbamoyl or the like, amino, alkylamino of 1-10 (preferably 1-5) carbon atoms, such as methylamino or the like, mercapto, alkylthio of 1-10 (preferably 1-5) carbon atoms, such as methylthio, ethylthio, propylthio, butylthio or the like, aralkyl or 7-12 (preferably 7-10) carbon atoms, such as benzyl, phenethyl or the like, carboxyl, alkoxycarbonyl of 2-10 (preferably 2-6) carbon atoms, such as methoxycarbonyl, ethoxycarbonyl or the like, carboxyalkyl of 2-10 (preferably 2-6) carbon atoms, such as carboxymethyl, 2-carboxyethyl, 2-carboxypropyl or the like, acylamino such as alkylcarbonylamino of 1-10 (preferably 1-5) carbon atoms, such as acetylamino, propionylamino or the like, alkylcarbonyl of 2-10 (preferably 2-6) carbon atoms, such as acetyl, propionyl, or the like, hydroxyalkyl of 1-10 (preferably 1-5) carbon atoms, such as hydroxymethyl, 2-hydroxyethyl, 2-hydroxypropyl or the like, haloalkyl of 1-10 (preferably 1-5) carbon atoms, such as chloromethyl, trifluoromethyl, bromomethyl, 2-chloroethyl or the like, oxo and phenyl optionally substituted with at least one hydroxy and/or $C_1$-$C_5$ alkoxy, such as methoxy, ethoxy, propoxy, butoxy or the like; a naphthoquinonyl, anthryl, phenanthryl, pentalenyl, heptalenyl, azulenyl, biphenylenyl, as -indacenyl, S-indacenyl, acenaphthylenyl, phenylcarbonylphenyl, phenoxyphenyl, benzofuranyl, isobenzofuranyl, benzo (b) thienyl, isobenzothienyl, thianthrenyl, dibenzothienyl, phenoxathiinyl, indolyl, 1H-indazolyl, quinolyl, isoquinolyl, phthalazinyl, 1,8-naphthyridinyl, quinoxalinyl, quinazolinyl, cinnolinyl, carbazolyl, acridinyl, phenazinyl, phenothiazinyl, phenoxazinyl or benzimidazolyl group each of which is unsubstituted or substituted with one or more groups selected from the group consisting of halo, nitro, cyano, hydroxy, alkyl of 1-10 (preferably 1-5) carbon atoms, such as methyl, ethyl, propyl, butyl or the like, alkoxy of 1-10 (preferably 1-5) carbon atoms, such as methoxy, ethoxy, propoxy, butoxy or the like, dialkylamino of 2-20 (preferably 2-10) carbon atoms, such as dimethylamino, diethylamino, dipropylamino or the like, sulfoamino, carbamoyl, N,N-dialkylcarbamoyl of 3-10 (preferably 3-7) carbon atoms, such as N,N-dimethylcarbamoyl, N,N-diethylcarbamoyl or the like, amino, alkylamino of 1-10 (preferably 1-5) carbon atoms, such as methylamino, ethylamino, propylamino, butylamino or the like, mercapto, alkylthio of 1-10 (preferably 1-5) carbon atoms, such as methylthio, ethylthio, propylthio, butylthio or the like, aralkyl of 7-12 (preferably 7-10) carbon atoms, such as benzyl, phenethyl or the like, carboxyl, alkoxycarbonyl of 2-10 (preferably 2-6) carbon atoms, such as methoxycarbonyl, ethoxycarbonyl or the like, carboxyalkyl of 2-10 (preferably 2-6) carbon atoms, such as carboxymethyl, 2-carboxyethyl 2-carboxypropyl or the like, acylamino such as alkylcarbonylamino of 1-10 (preferably 1-5) carbon atoms, such as acetylamino, propionylamino or the like, alkylcarbonyl of 2-10 (preferably 2-6) carbon atoms, such as acetyl, propionyl or the like, hydroxyalkyl of 1-10 (preferably 1-5) carbon atoms, such as hydroxymethyl, 2-hydroxyethyl, 2-hydroxypropyl or the like, haloalkyl of 1-10 (preferably 1-5) carbon atoms, such as chloromethyl, trifluoromethyl, bromomethyl, 2-chloroethyl or the like, and phenyl optionally substituted with at least one hydroxy and/or $C_1$-$C_5$ alkoxy, such as methoxy, ethoxy, propoxy, butoxy or the like;

a $C_9$-$C_{16}$ cycloalkylphenyl, such as cyclopentylphenyl, cyclohexylphenyl, cyclooctylphenyl or the like, $C_{10}$-$C_{18}$ cycloalkylalkylphenyl, such as cyclohexylmethylphenyl, (2-cyclohexylethyl)phenyl, (4-cyclohexylbutyl)phenyl, cyclooctylmethylphenyl or the like, $C_9$-$C_{16}$ cycloalkyloxyphenyl, such as cyclopentyloxyphenyl, cyclohexyloxyphenyl, cyclooctyloxyphenyl or the like, $C_9$-$C_{16}$ cycloalkylthiophenyl, such as cyclopentylthiophenyl, cyclohexylthiophenyl, cyclooctylthiophenyl or the like, 9,10-dihydroanthryl, 5,6,7,8-tetrahydroanthryl, 9,10-dihydrophenanthryl, 1,2,3,4,5,6,7,8-octahydrophenanthryl, indenyl, indanyl, fluorenyl, acenaphthenyl, phenylthiophenyl, isochromanyl, 2,3-dihydrobenzofuranyl, 1,3-dihydroisobenzofuranyl, thioxanthenyl, 2H-chromenyl, 3,4-dehydro-1-isochromanyl, 4H-chromenyl, indolinyl, isoindolinyl, 1,2,3,4-tetrahydroquinolyl, or 1,2,3,4-tetrahydroisoquinolyl group each of which is unsubstituted or substituted with one or more groups selected from the group consisting of halo, nitro, cyano, hydroxy, alkyl of 1-10 (preferably 1-5) carbon atoms, such as methyl, ethyl, propyl, butyl or the like, alkoxy of 1-10 (preferably 1-5) carbon atoms, such as methoxy, ethoxy, propoxy, butoxy or the like, dialkylamino of 2-20 (preferably 2-10) carbon atoms, such as dimethylamino, diethylamino, dipropylamino or the like, sulfoamino, carbamoyl, N,N-dialkylcarbamoyl of 3-10 (preferably 3-7) carbon atoms, such as N,N-dimethylcarbamoyl, N,N-diethylcarbamoyl or the like, amino, alkylamino of 1-10 (preferably 1-5) carbon atoms, such as methylamino or the like, mercapto, alkylthio of 1-10 (preferably 1-5) carbon atoms, such as methylthio, ethylthio, propylthio, butylthio or the like, aralkyl of 7-12 (preferably 7-10) carbon atoms, such as benzyl, phenethyl or the like, carboxyl, alkoxycarbonyl of 2-10 (preferably 2-6) carbon atoms, such as methoxycarbonyl, ethoxycarbonyl or the like, carboxyalkyl of 2-10 (preferably 2-6) carbon atoms, such as carboxymethyl, 2-carboxyethyl, 2-carboxypropyl or the like, acylamino such as alkylcarbonylamino of 1-10 (preferably 1-5) carbon atoms, such as acetylamino, propionylamino or the like, alkylcarbonyl of 2-10 (preferably 2-6) carbon atoms, such as acetyl, propionyl, or the like, hydroxyalkyl of 1-10 (preferably 1-5) carbon atoms, such as hydroxymethyl, 2-hydroxyethyl, 2-hydroxypropyl or the like, haloalkyl of 1-10 (preferably 1-5) carbon atoms, such as chloromethyl, trifluoromethyl, bromomethyl, 2-chloroethyl or the like, oxo and phenyl optionally substituted with at least one hydroxy and/or $C_1$-$C_5$ alkoxy, such as methoxy, ethoxy, propoxy, butoxy or the like; or benzene-ring substituted

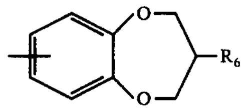

wherein $R_6$ is hydrogen, $C_1$-$C_{10}$ alkyl, such as methyl, ethyl, propyl, butyl or the like, or $C_1$-$C_{10}$ alkoxy, such as methoxy, ethoxy, propoxy, butoxy or the like, and said substituent is at least one $C_1$-$C_5$ alkyl, such as methyl, ethyl, propyl, butyl or the like, $C_1$-$C_5$ alkoxy, such as methoxy, ethoxy, propoxy or the like, or mixtures thereof.

Illustrative of suitable $N^2$-arylsulfonyl-L-argininamides are those shown in the table below. In this table, the prior art reference cited in the second column disclose a method of preparation for the compound listed in the second column. The Example No. listed in the last column refers to an Example of this application which discloses the details of a method by which the product compound of the fifth column of the table may be prepared.

TABLE I
| No. | ArSO₂CL or ArSO₃H or salts thereof (Literature reference) | Starting material Amino acid ester | Product 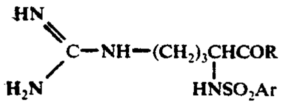 Ar | R | Preparation Procedure |
|---|---|---|---|---|---|
| 1 | 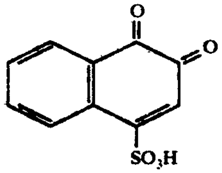 Ger. 1,123,315 | 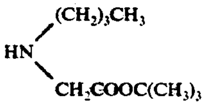 | 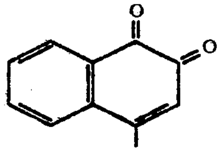 | 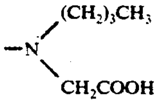 | |
| 2 | 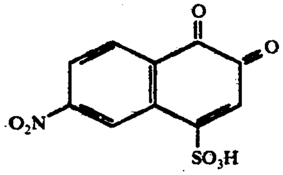 Ger. 1,123,315 | 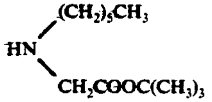 | 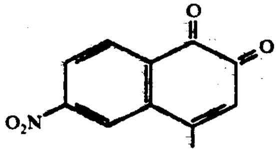 | 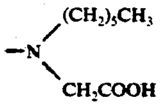 | 1 |
| 3 | 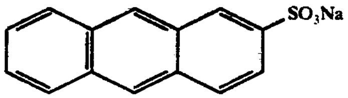 CA, 23, 1897 | 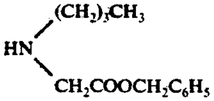 | 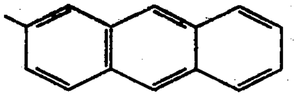 | 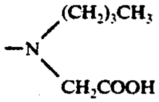 | 3 |
| 4 | 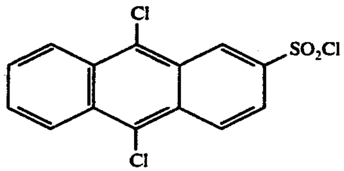 J. Gen. Chem., 6, 444 (1936) | 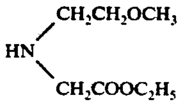 | 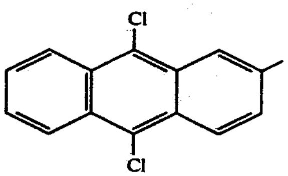 | 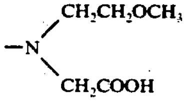 | 2 |
| 5 | 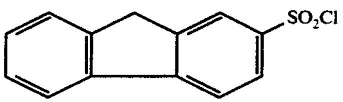 Compt. rend., 218, 973 (1944) | 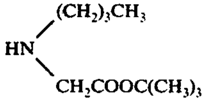 | 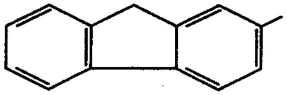 | 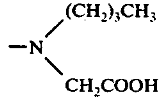 | |

TABLE I-continued
| No. | ArSO₂CL or ArSO₃H or salts thereof (Literature reference) | Starting material Amino acid ester | Product 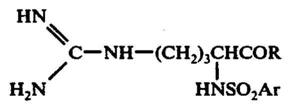 Ar | R | Preparation Procedure |
|---|---|---|---|---|---|
| 6 | 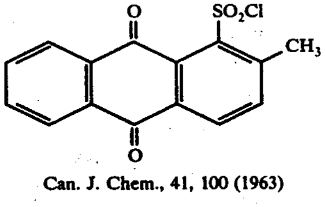 Can. J. Chem., 41, 100 (1963) | 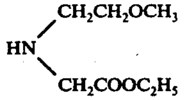 | 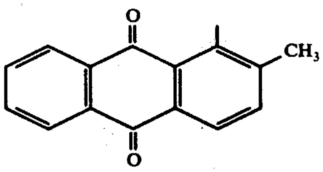 | 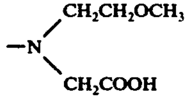 | 2 |
| 7 | 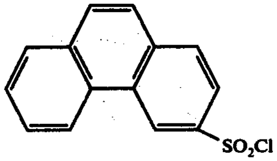 Compt. rend., 218, 973 (1944) | 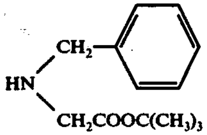 | 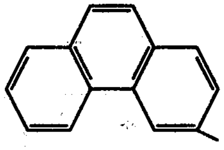 | 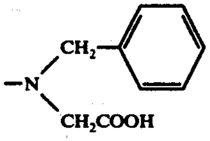 | 1 |
| 8 | 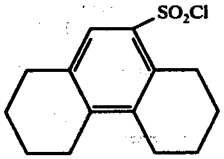 CA, 49, 5414 | 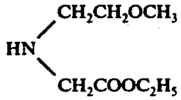 | 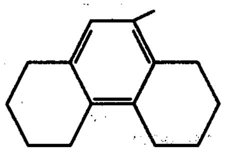 | 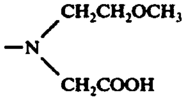 | 2 |
| 9 | 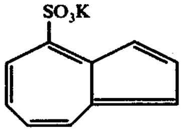 Z. Chem., 3, 426 (1963) | 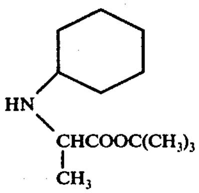 | 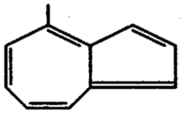 | 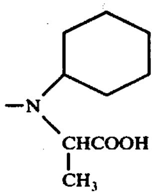 | 1 |

TABLE I-continued
| No. | $ArSO_2CL$ or $ArSO_3H$ or salts thereof (Literature reference) | Starting material Amino acid ester | Product 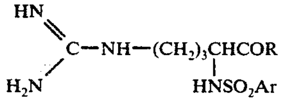 Ar | R | Preparation Procedure |
|---|---|---|---|---|---|
| 10 | 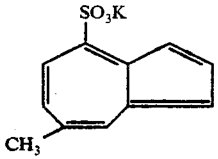 Z. Chem., 3, 426 (1963) | 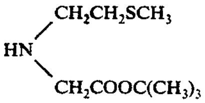 | 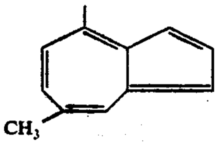 | 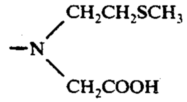 | |
| 11 | 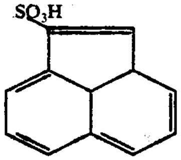 Ger. 1,219,477 | 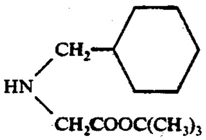 | 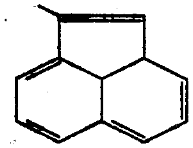 | 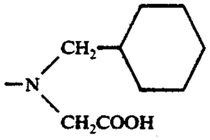 | 1 |
| 12 | 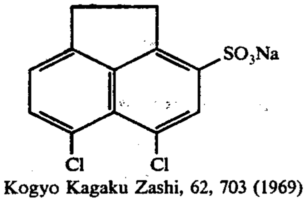 Kogyo Kagaku Zashi, 62, 703 (1969) | 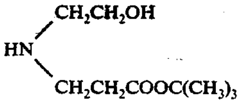 | 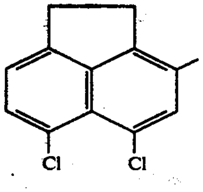 | 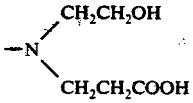 | 1 |
| 13 | 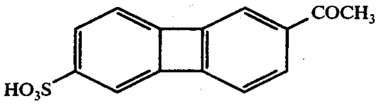 J. Chem. Soc., 1970, 2500 | 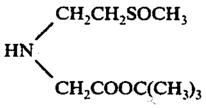 | 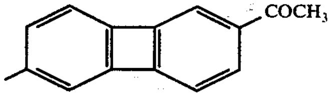 | 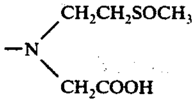 | 1 |
| 14 | 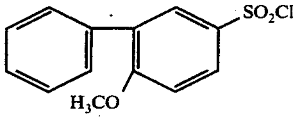 (m. p. 80–2° C) | 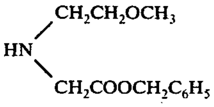 | 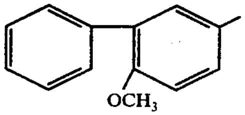 | 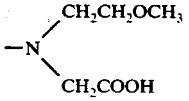 | 3 |

TABLE I-continued
| No. | ArSO$_2$CL or ArSO$_3$H or salts thereof (Literature reference) | Starting material Amino acid ester | Product 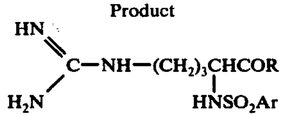 Ar | R | Prepa-ration Pro-cedure |
|---|---|---|---|---|---|
| 15 | 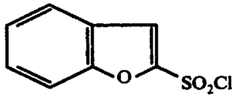 Ger. 56,780 (CA, 68, 12705) | 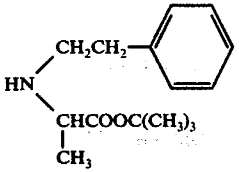 | 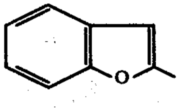 | 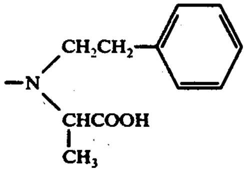 | 1 |
| 16 | 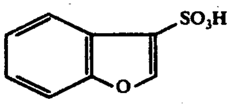 CA, 47, 10519 | 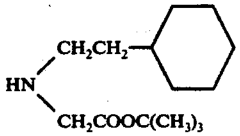 | 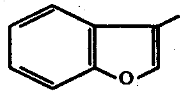 | 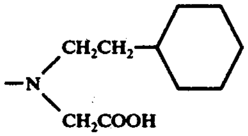 | 1 |
| 17 | 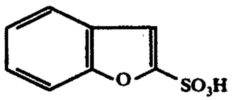 CA, 32, 2938 | 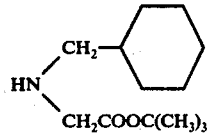 | 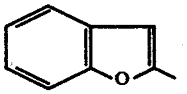 | 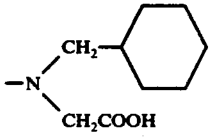 | 2 |
| 18 | 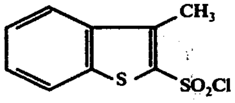 Monatsh, 92, 677 (1961) | 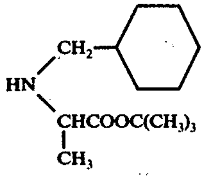 | 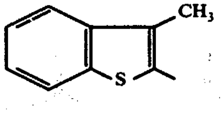 | 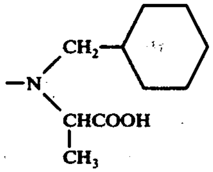 | 1 |
| 19 | 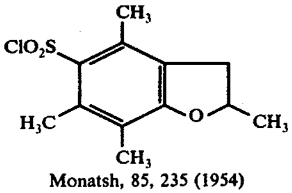 Monatsh, 85, 235 (1954) | 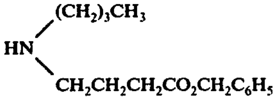 | 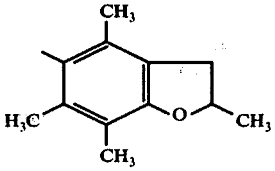 | 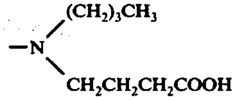 | 3 |

TABLE I-continued
| No. | $ArSO_2CL$ or $ArSO_3H$ or salts thereof (Literature reference) | Starting material Amino acid ester | Product 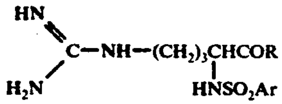 Ar | R | Preparation Procedure |
|---|---|---|---|---|---|
| 20 | 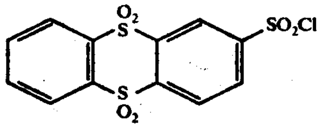 J. Ger. Chem., 10, 1077 (1940) | 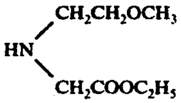 | 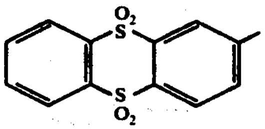 | 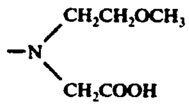 | 2 |
| 21 | 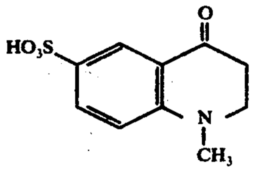 J. Chem., Soc., 1958, 3830 | 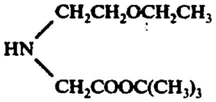 | 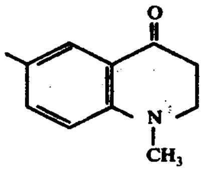 | 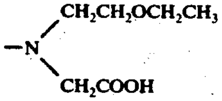 | 1 |
| 22 | 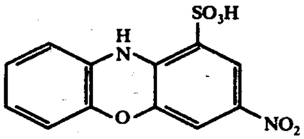 J. Chem. Soc., 1953, 1499 | 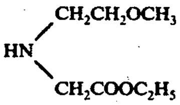 | 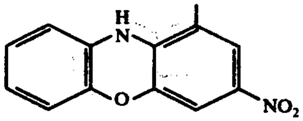 | 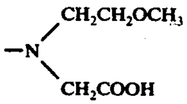 | 2 |
| 23 | 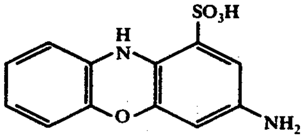 J. Chem. Soc., 1953, 1499 | 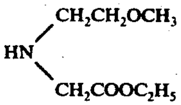 | 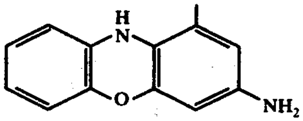 | 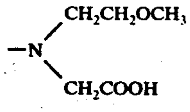 | 2 |
| 24 | 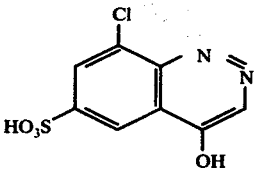 J. Chem. Soc., 1968, 687 | 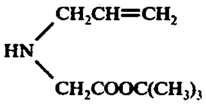 | 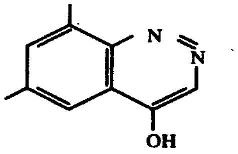 | 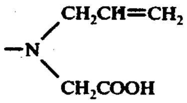 | 1 |

TABLE I-continued
| No. | $ArSO_2CL$ or $ArSO_3H$ or salts thereof (Literature reference) | Starting material Amino acid ester | Product<br>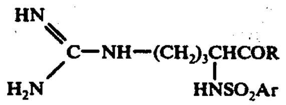<br>Ar | R | Preparation Procedure |
|---|---|---|---|---|---|
| 25 | 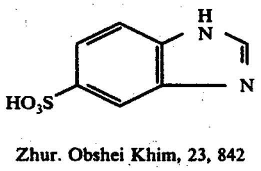<br>Zhur. Obshei Khim, 23, 842 | 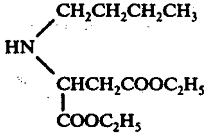 | 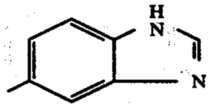 | 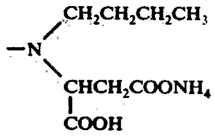 | 2 |
| 26 | 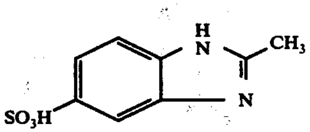<br>Zhur Obshei Khim, 23, 842 | 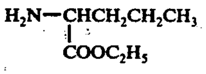 | 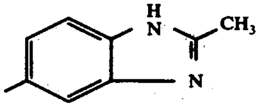 | 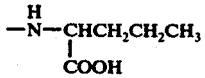 | 2 |
| 27 | 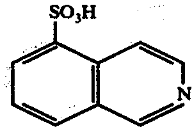<br>J. Am. Chem. Soc., 75, 2095 (1953) | 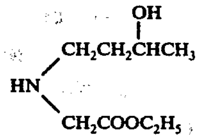 | 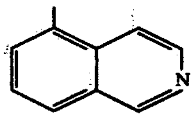 | 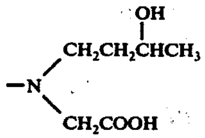 | 2 |
| 28 | 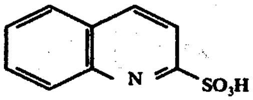<br>U.S. 2,708,669 | 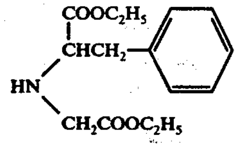 | 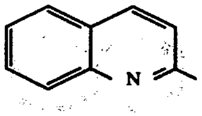 | 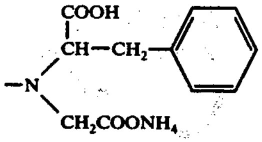 | 2 |
| 29 | 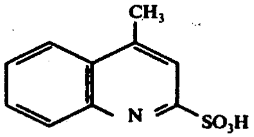<br>Gazz. chim. ital., 81,764 (1959) | 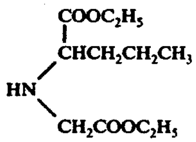 | 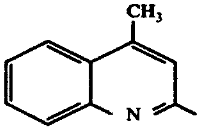 | 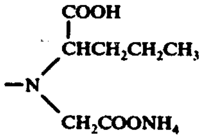 | 2 |

TABLE I-continued
| No. | ArSO2CL or ArSO3H or salts thereof (Literature reference) | Starting material Amino acid ester | Product 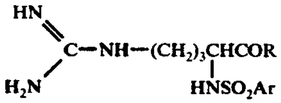 Ar | R | Preparation Procedure |
|---|---|---|---|---|---|
| 30 | 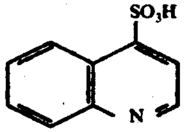 Pharm. Bull. (Japan) 2, 247 (1954) | 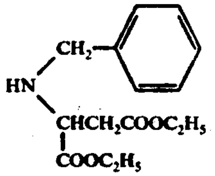 | 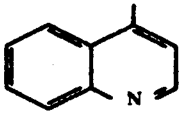 | 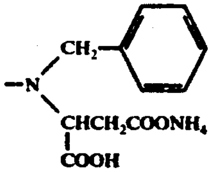 | 2 |
| 31 | 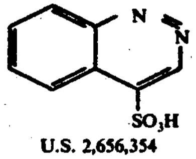 U.S. 2,656,354 | 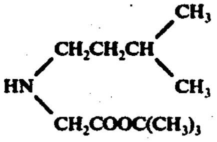 | 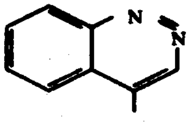 | 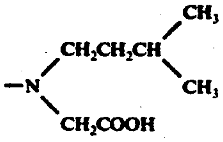 | 1 |
| 32 | 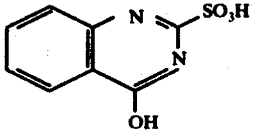 Compt. Rend. Acad. Bulgrare Sci., 18, 243 | 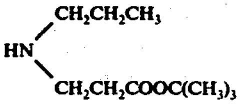 | 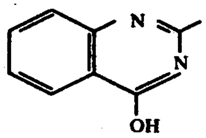 | 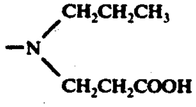 | 1 |
| 33 | 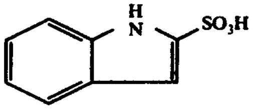 Zhur. Obshei Khim., 22, 866 (1952) | 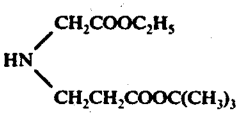 | 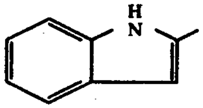 | 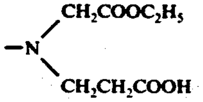 | 1 |
| 34 | 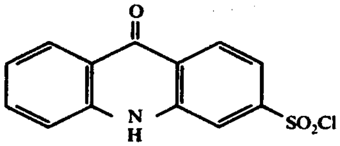 Roczniki chem., 15, 565 (1935) | 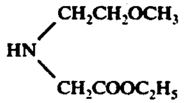 | 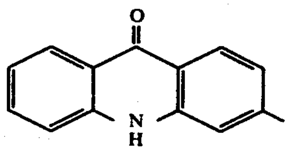 | 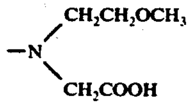 | 2 |

TABLE I-continued
| No. | $ArSO_2CL$ or $ArSO_3H$ or salts thereof (Literature reference) | Starting material Amino acid ester | Product 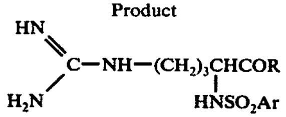 Ar | R | Preparation Procedure |
|---|---|---|---|---|---|
| 35 | 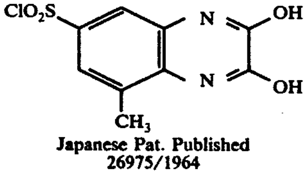 Japanese Pat. Published 26975/1964 | 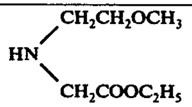 | 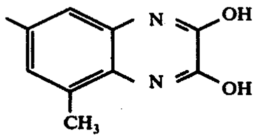 | 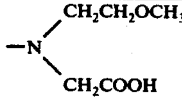 | 2 |
| 36 | 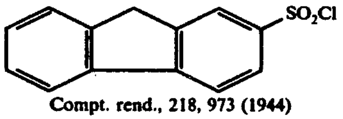 Compt. rend., 218, 973 (1944) | 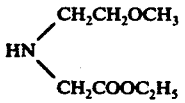 | 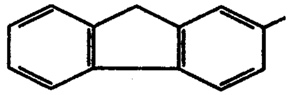 | 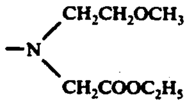 | 3 |
| 37 | 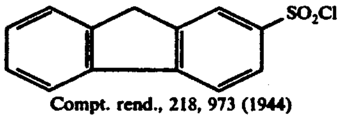 Compt. rend., 218, 973 (1944) | 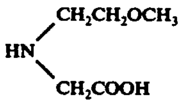 | 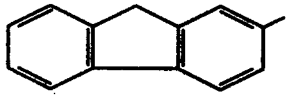 | 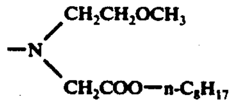 | 2 |
| 38 | " | 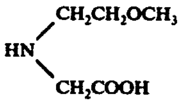 | " | 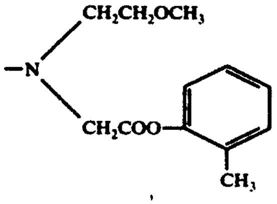 | 4 |
| 39 | " | 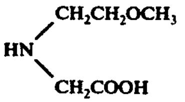 | " | 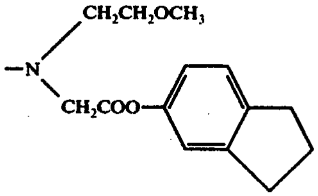 | 4 |
| 40 | " | 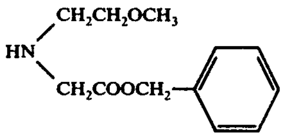 | " | 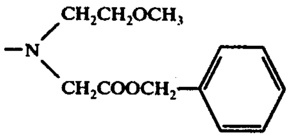 | 3 |

Also illustrative of suitable $N^2$-arylsulfonyl-L-argininamides are those shown in the table below. In this table, the Example No. listed in the sixth column refers to the Example of this application by which the compound in the first column was prepared.

| Sample No. | Compound 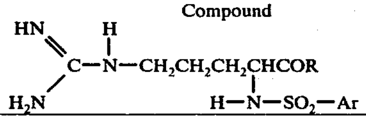 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 1 | 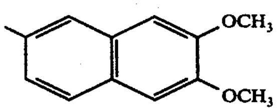 | 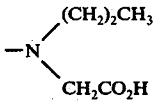 | — | 8 | 1 | powder | 52.76<br>52.68 | 6.35<br>6.21 | 13.38<br>13.30 | 3,360<br>3,160<br>1,620 |
| 2 | " | 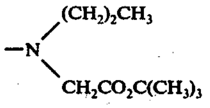 | $\frac{1}{2}H_2SO_3$ | | 1 | 134–6 | 52.25<br>52.07 | 6.82<br>6.73 | 11.29<br>10.89 | 3,360<br>3,180<br>1,740<br>1,375 |
| 3 | " | 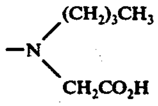 | — | 0.3 | 1 | powder | 53.62<br>53.48 | 6.56<br>6.43 | 13.03<br>12.98 | 3,360<br>3,140<br>1,622 |
| 4 | " | 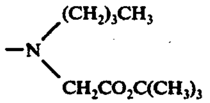 | $\frac{1}{2}H_2SO_3$ | | 1 | 164–6 | 52.98<br>52.69 | 7.00<br>6.98 | 11.04<br>10.86 | 3,390<br>3,165<br>1,735<br>1,370 |
| 5 | " | 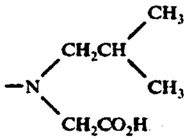 | — | 2 | 1 | powder | 53.62<br>53.43 | 6.56<br>6.51 | 13.03<br>13.12 | 3,360<br>3,160<br>1,620 |
| 6 | " | 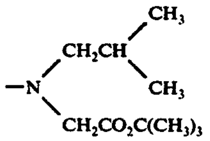 | $\frac{1}{2}H_2SO_3$ | | 1 | " | 52.98<br>52.59 | 7.00<br>6.79 | 11.04<br>10.89 | 3,390<br>3,170<br>1,737<br>1,370 |
| 7 | " | 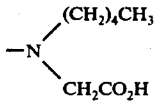 | — | 5 | 1 | " | 54.43<br>54.38 | 6.76<br>6.79 | 12.70<br>12.56 | 3,350<br>3,180<br>1,630 |

-continued

| Sample No. | Compound<br>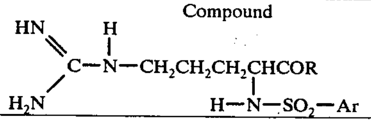 (I)<br>Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 8 | " | 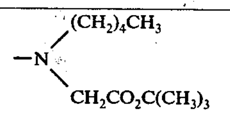 | $\frac{1}{2}H_2SO_3$ | | 1 | 195-6 | 53.69<br>53.40 | 7.15<br>7.12 | 10.80<br>10.56 | 3,380<br>3,180<br>1,738<br>1,375 |
| 9 | " | 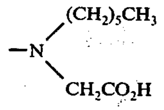 | — | 1.5 | 1 | powder | 55.21<br>54.98 | 6.95<br>7.02 | 12.38<br>12.47 | 3,360<br>3,200<br>1,622 |
| 10 | " | 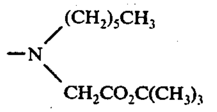 | $\frac{1}{2}H_2SO_3$ | | 1 | 198–200 | 54.37<br>54.30 | 7.30<br>7.27 | 10.57<br>10.36 | 3,360<br>3,160<br>1,730<br>1,368 |
| 11 | " | 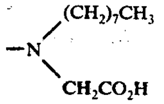 | — | | 1 | powder | 56.64<br>56.41 | 7.30<br>7.17 | 11.80<br>11.51 | 3,360<br>3,180<br>1,620 |
| 12 | " | 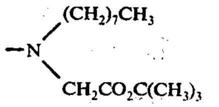 | $\frac{1}{2}H_2SO_3$ | | 1 | 172–174 | 55.64<br>55.31 | 7.59<br>7.63 | 10.14<br>10.18 | 3,380<br>3,180<br>1,740<br>1,375 |
| 13 | " | 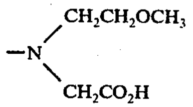 | — | 0.5 | 3 | powder | 51.20<br>50.93 | 6.17<br>6.02 | 3,380<br>3,180<br>1,630 | |
| 14 | " | 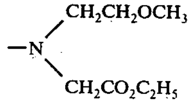 | 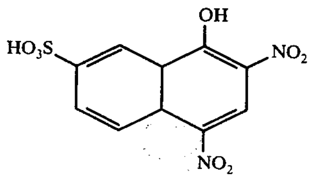 | 1.5 | 3 | 185 | 47.67<br>47.64 | 4.92<br>4.81 | 11.12<br>11.12 | 3,375<br>3,200<br>1,740 |
| 15 | " | 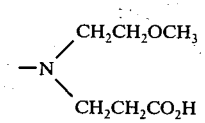 | — | 2.5 | 3 | powder | 52.07<br>52.21 | 6.37<br>6.04 | 12.67<br>12.51 | 3,380<br>3,200<br>1,620 |

-continued

| Sample No. | Compound 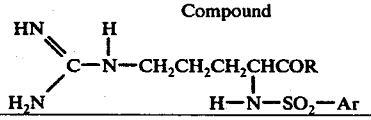 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 16 | " | 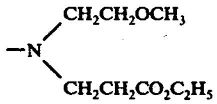 | — | | 3 | " | 53.69<br>53.53 | 6.76<br>6.69 | 12.04<br>12.38 | 3,380<br>3,200<br>1,740 |
| 17 | " | 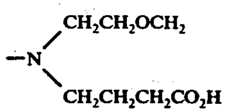 | — | 2.5 | 1 | " | 52.90<br>52.71 | 6.57<br>6.43 | 12.34<br>12.46 | 3,350<br>3,160<br>1,640 |
| 18 | " | 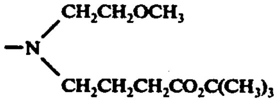 | ½$H_2SO_3$ | | 1 | " | 52.40<br>52.16 | 6.96<br>7.13 | 10.54<br>10.28 | 3,340<br>3,160<br>1,736<br>1,380 |
| 19 | " | 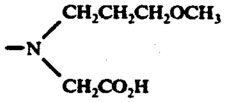 | — | 5 | 1 | " | 52.07<br>51.91 | 6.37<br>6.19 | 12.65<br>12.38 | 3,360<br>3,160<br>1,620 |
| 20 | " | 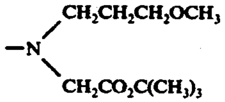 | ½$H_2SO_3$ | | 1 | " | 51.68<br>51.43 | 6.82<br>6.66 | 10.76<br>10.58 | 3,380<br>3,160<br>1,740<br>1,370 |
| 21 | " | 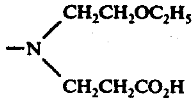 | — | 4 | 1 | " | 52.90<br>52.59 | 6.57<br>6.41 | 12.34<br>12.16 | 3,360<br>3,160<br>1,640 |
| 22 | " | 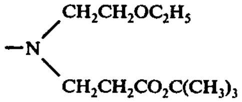 | ½$H_2SO_3$ | | 1 | " | 52.98<br>52.73 | 7.00<br>7.00 | 11.04<br>10.82 | 3,377<br>3,160<br>1,740<br>1,368 |

-continued

| Sample No. | Compound 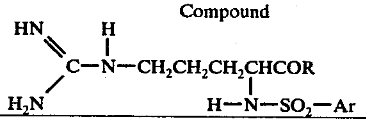 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 23 | 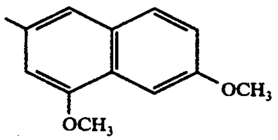 | 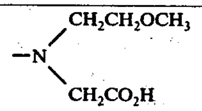 | — | 4 | 4 | " | 51.20<br>51.31 | 6.17<br>6.01 | 12.98<br>12.67 | 3,360<br>3,180<br>1,610 |
| 24 | " | 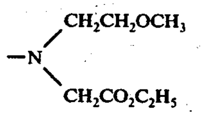 | 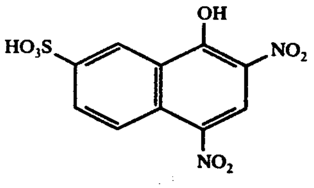 | | 4 | 225-7 | 47.67<br>47.62 | 4.92<br>4.84 | 11.12<br>11.18 | 3,375<br>3,200<br>1,742 |
| 25 | " | 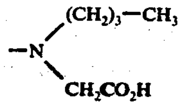 | — | 2 | 1 | powder | 53.62<br>53.58 | 6.56<br>6.48 | 13.03<br>12.94 | 3,380<br>3,200<br>1,630 |
| 26 | " | 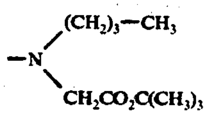 | ½$H_2SO_3$ | | 1 | 224 | 52.98<br>52.73 | 7.00<br>7.00 | 11.04<br>10.82 | 3,360<br>3,160<br>1,740<br>1,370 |
| 27 | 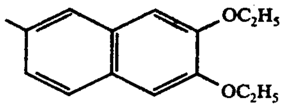 | 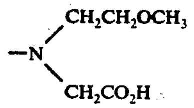 | — | 15 | 1 | powder | 52.89<br>52.77 | 6.57<br>6.80 | 12.34<br>12.59 | 3,380<br>3,200<br>1,625 |
| 28 | " | 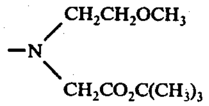 | ½$H_2SO_3$ | | 1 | " | 52.39<br>52.10 | 6.97<br>6.84 | 10.54<br>10.21 | 3,370<br>3,150<br>1,740<br>1,370 |
| 29 | " | 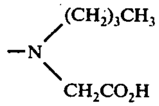 | — | | 1 | powder | 55.20<br>55.00 | 6.95<br>6.81 | 12.38<br>12.21 | 3,360<br>3,150<br>1,620 |

-continued

| Sample No. | Compound 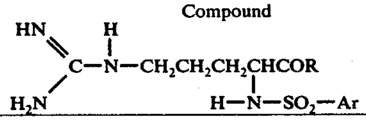 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 30 | " | 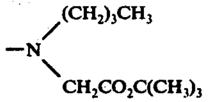 | ½$H_2SO_3$ | | 1 | " | 54.36<br>54.25 | 7.30<br>7.11 | 10.57<br>10.81 | 3,370<br>3,200<br>1,735<br>1,370 |
| 31 | 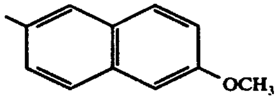 | 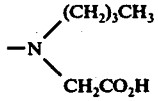 | — | 0.5 | 1 | " | 54.43<br>54.21 | 6.55<br>6.50 | 13.80<br>13.79 | 3,360<br>3,180<br>1,632 |
| 32 | " | 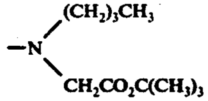 | ½$H_2SO_3$ | | 1 | " | 53.63<br>53.60 | 7.00<br>6.79 | 11.58<br>11.40 | 3,380<br>3,200<br>1,740<br>1,370 |
| 33 | " | 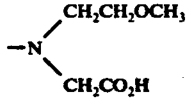 | — | | 1 | " | 51.86<br>51.64 | 6.13<br>6.09 | 13.75<br>13.84 | 3,370<br>3,200<br>1,625 |
| 34 | " | 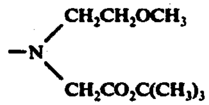 | ½$H_2SO_3$ | | 1 | " | 55.21<br>55.11 | 6.95<br>6.76 | 12.38<br>12.27 | 3,380<br>3,180<br>1,738<br>1,368 |
| 35 | 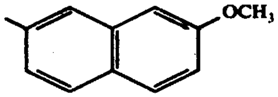 | 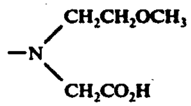 | — | 0.5 | 3 | " | 51.86<br>51.72 | 6.13<br>6.11 | 13.75<br>13.63 | 3,370<br>3,160<br>1,620 |
| 36 | " | 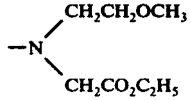 | 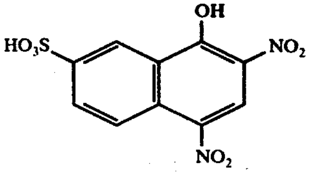 | | 3 | 158-160 | 47.94<br>47.83 | 4.85<br>4.80 | 11.51<br>11.43 | 3,375<br>3,200<br>1,740 |

-continued

| Sample No. | Compound 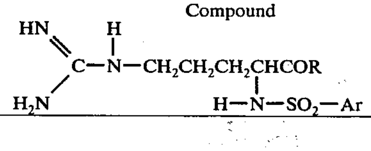 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) (cm$^{-1}$) |
|---|---|---|---|---|---|---|---|---|---|---|
| 37 | " | 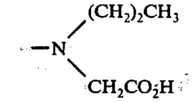 | — | | 1 | powder | 53.53<br>53.40 | 6.33<br>6.21 | 14.19<br>14.04 | 3,375<br>3,150<br>1,620 |
| 38 | " | 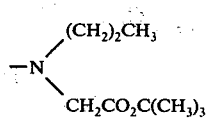 | ½$H_2SO_3$ | | 1 | " | 52.86<br>52.77 | 6.83<br>6.66 | 11.86<br>11.75 | 3,380<br>3,200<br>1,740<br>1,370 |
| 39 | " | 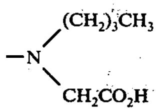 | — | 0.5 | 1 | " | 54.43<br>54.22 | 6.55<br>6.31 | 13.80<br>13.59 | 3,380<br>3,150<br>1,620 |
| 40 | " | 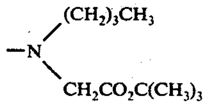 | ½$H_2SO_3$ | | 1 | 131-137 (dec.) | 53.63<br>53.40 | 7.00<br>7.10 | 11.58<br>11.40 | 3,380<br>3,160<br>1,750<br>1,640 |
| 41 | " | 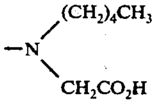 | — | | 1 | powder | 55.26<br>55.21 | 6.76<br>6.65 | 13.43<br>13.29 | 3,350<br>1,630 |
| 42 | " | 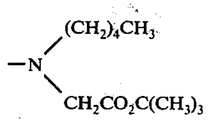 | ½$H_2SO_3$ | | 1 | 169-175 (dec.) | 54.35<br>54.27 | 7.17<br>7.00 | 11.32<br>11.08 | 3,350<br>3,180<br>1,740<br>1,640 |
| 43 | 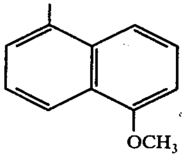 | 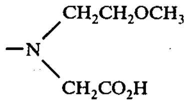 | — | 2.5 | 1 | powder | 51.86<br>51.77 | 6.13<br>6.00 | 13.75<br>13.72 | 3,365<br>3,200<br>1,620 |

-continued
| Sample No. | Compound 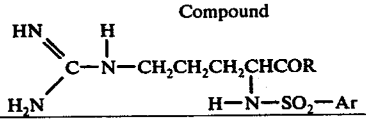 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 44 | " | 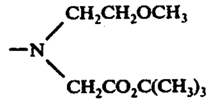 | ½$H_2SO_3$ | | 1 | " | 51.47 | 6.65 | 11.54 | 3,370 3,200 |
| | | | | | | | 51.20 | 6.35 | 11.24 | 1,740 1,370 |
| 45 | " | 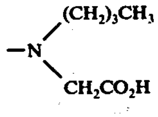 | — | | 1 | " | 54.43 | 6.55 | 13.80 | 3,375 3,200 |
| | | | | | | | 54.28 | 6.31 | 13.70 | 1,622 |
| 46 | " | 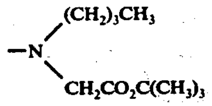 | ½$H_2SO_3$ | | 1 | " | 53.63 | 7.00 | 11.58 | 3,380 3,200 |
| | | | | | | | 53.53 | 7.08 | 11.40 | 1,740 1,370 |
| 47 | " | 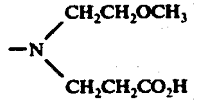 | — | | 1 | " | 52.76 | 6.35 | 13.38 | 3,375 3,180 |
| | | | | | | | 52.47 | 6.01 | 13.09 | 1,620 |
| 48 | " | 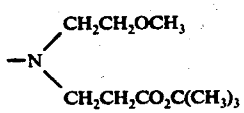 | ½$H_2SO_3$ | | 1 | " | 52.24 | 6.82 | 11.28 | 3,380 3,200 |
| | | | | | | | 52.00 | 6.55 | 11.00 | 1,740 1,368 |
| 49 | 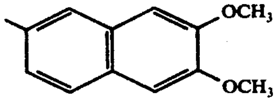 | 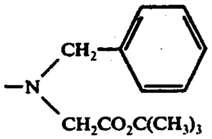 | 0.5 $H_2SO_3$ | | 1 | 189-191 (dec.) | 55.68 | 6.33 | 10.47 | 3,360 3,160 |
| | | | | | | | 55.36 | 6.35 | 10.45 | 1,730 |
| 50 | " | 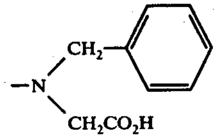 | — | 2.5 | 1 | powder | 56.73 | 5.82 | 12.25 | 3,370 3,200 |
| | | | | | | | 56.43 | 5.80 | 12.19 | 1,615 |

-continued
| Sample No. | Compound 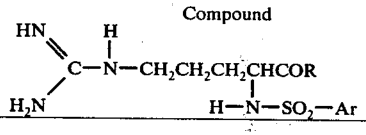 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) (cm⁻¹) |
|---|---|---|---|---|---|---|---|---|---|---|
| 51 | " | 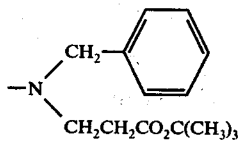 | 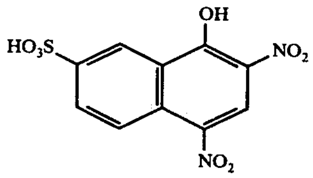 | | 1 | 132-135 (dec.) | 52.78<br>52.61 | 5.17<br>5.15 | 10.26<br>10.23 | 3,360<br>3,180<br>1,720 |
| 52 | " | 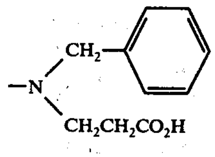 | — | 10 | 1 | powder | 57.42<br>57.19 | 6.02<br>6.10 | 11.96<br>11.73 | 3,360<br>3,160<br>1,620 |
| 53 | " | 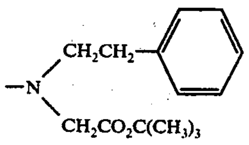 | 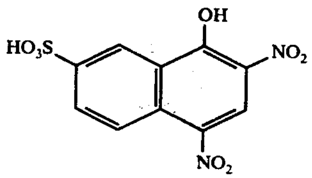 | | 1 | 157-158 (dec.) | 52.78<br>52.63 | 5.17<br>5.14 | 10.26<br>10.09 | 3,380<br>3,220<br>1,750 |
| 54 | " | 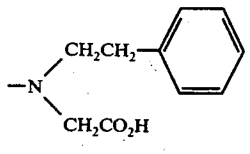 | — | 3.0 | 1 | powder | 57.42<br>57.09 | 6.02<br>6.06 | 11.96<br>11.74 | 3,360<br>3,200<br>1,590 |
| 55 | " | 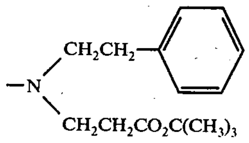 | 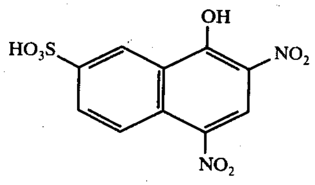 | | 1 | 155-157 (dec.) | 53.25<br>53.13 | 5.30<br>5.21 | 10.11<br>10.03 | 3,380<br>3,180<br>1,720 |

-continued
| Sample No. | Compound 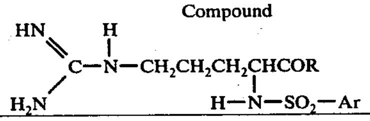 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 56 | " | 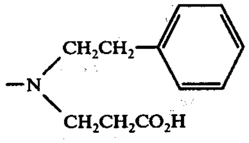 | — | 50 | 1 | powder | 58.08<br>57.93 | 6.22<br>6.04 | 11.68<br>11.54 | 3,200-3,380 (broad)<br>1,620 |
| 57 | 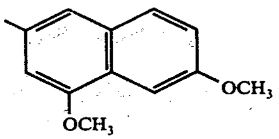 | 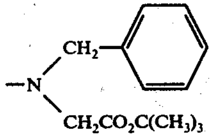 | 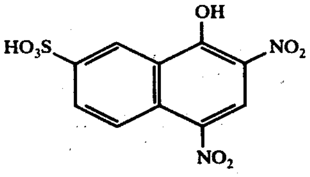 | | 1 | 153-156 (dec.) | 52.28<br>52.14 | 5.03<br>4.98 | 10.41<br>10.36 | 3,400<br>3,080<br>1,740 |
| 58 | " | 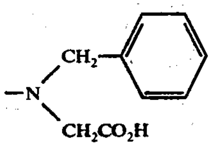 | — | 6.5 | 1 | powder | 56.73<br>56.58 | 5.82<br>5.73 | 12.25<br>12.14 | 3,000-3,400 (broad)<br>1,600 |
| 59 | 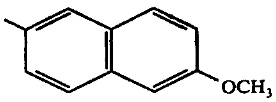 | 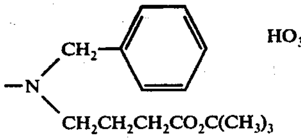 | 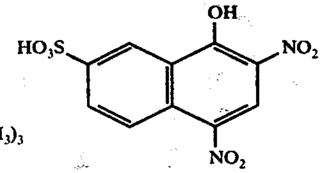 | | 1 | 144-148 (dec.) | 53.67<br>53.69 | 5.26<br>5.24 | 10.43<br>10.39 | 3,360<br>3,200<br>1,720 |
| 60 | " | 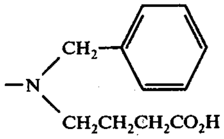 | — | 50 | 1 | powder | 59.04<br>59.14 | 6.19<br>6.15 | 12.30<br>12.28 | 3,040-3,360 (broad)<br>1,610 |

-continued
| Sample No. | Compound 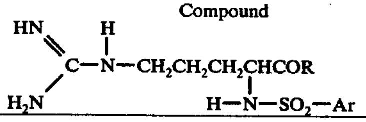 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 61 | " | 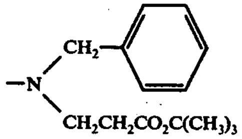 | 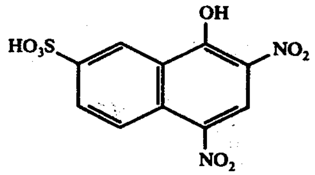 | | 1 | 155-158 (dec.) | 53.19<br>54.97 | 5.12<br>5.06 | 10.59<br>10.48 | 3,400<br>3,200<br>1,730 |
| 62 | " | 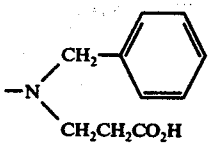 | — | 15 | 1 | powder | 58.37<br>58.19 | 6.00<br>5.98 | 12.61<br>12.49 | 3,300<br>(broad)<br>1,640 |
| 63 | 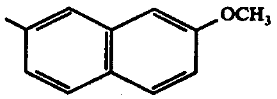 | 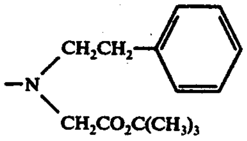 | 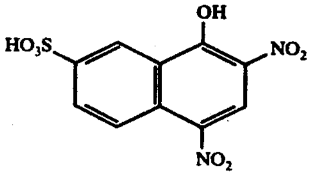 | | 1 | 147-150 (dec.) | 59.19<br>59.23 | 5.12<br>5.07 | 10.59<br>10.54 | 3,400<br>3,230<br>1,750 |
| 64 | " | 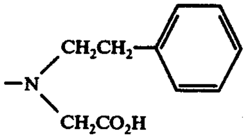 | — | 20 | 1 | powder | 58.37<br>58.21 | 6.00<br>5.93 | 12.61<br>12.46 | 3,200<br>(broad)<br>1,620 |
| 65 | 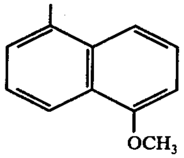 | 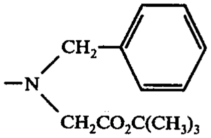 | — | | 1 | " | 60.29<br>60.21 | 6.58<br>6.56 | 11.72<br>11.64 | 3,365<br>3,170<br>1,730 |

-continued

| Sample No. | Compound 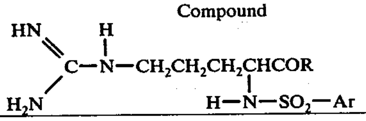 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 66 | " | 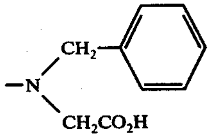 | — | 2.0 | 1 | " | 57.66<br>57.48 | 5.77<br>5.74 | 12.93<br>12.84 | 3,360<br>3,160<br>1,610 |
| 67 | 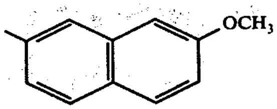 | 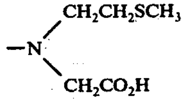 | — | 1 | 1 | " | 50.25<br>50.45 | 5.95<br>6.01 | 13.32<br>13.15 | 3,350<br>1,620<br>1,380<br>1,150 |
| 68 | 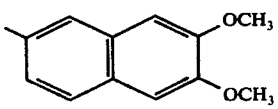 | 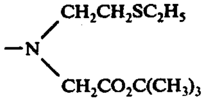 | $\frac{1}{2}$ $H_2SO_3$ | | 1 | " | 50.43<br>50.57 | 6.65<br>6.58 | 10.50<br>10.71 | 3,350<br>1,745<br>1,650<br>1,360 |
| 69 | " | 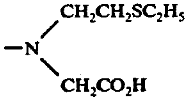 | — | 5 | 1 | 171-2 | 50.60<br>50.51 | 6.19<br>6.30 | 12.29<br>12.40 | 3,400<br>1,635<br>1,260<br>1,160 |
| 70 | " | 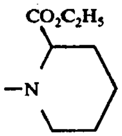 | — | | 2 | powder | 55.40<br>55.65 | 6.62<br>6.81 | 12.43<br>12.19 | 3,220<br>1,750<br>1,640 |
| 71 | 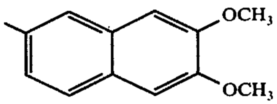 | 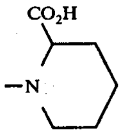 | — | 5 | 2 | powder | 53.82<br>53.66 | 6.21<br>5.96 | 13.08<br>12.81 | 3,350<br>1,625<br>1,155 |

-continued
Compound 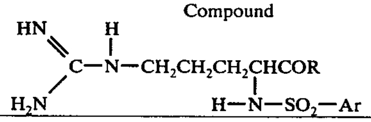 (I)
| Sample No. | Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 72 | 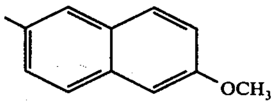 | 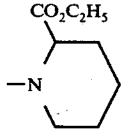 | 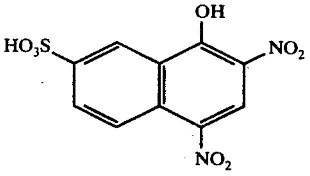 | | 2 | 192–193 | 49.58<br>49.24 | 4.87<br>4.70 | 11.56<br>11.85 | 3,210<br>1,747<br>1,638 |
| 73 | " | 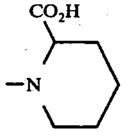 | I— | 3 | 2 | powder | 54.64<br>56.88 | 6.18<br>6.31 | 13.85<br>13.83 | 3,200<br>(broad)<br>1,620<br>1,150 |
| 74 | 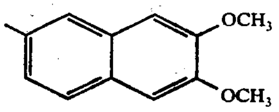 | 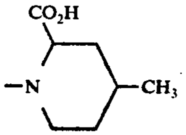 | — | 0.4 | 2 | " | 54.63<br>54.50 | 6.42<br>6.09 | 12.74<br>12.81 | 13,370<br>1,625<br>1,158 |
| 75 | 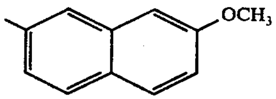 | 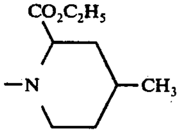 | 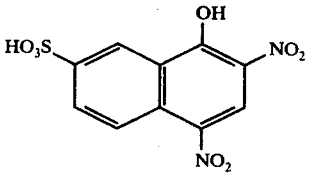 | | 2 | 188–190 | 50.17<br>50.01 | 5.03<br>4.78 | 11.38<br>11.56 | 3,200<br>1,740<br>1,635 |
| 76 | 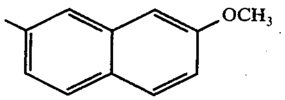 | 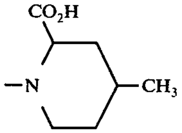 | — | 0.15 | 2 | powder | 55.47<br>55.49 | 6.40<br>6.33 | 13.98<br>13.51 | 3,250<br>(broad)<br>1,625 |

-continued
| Sample No. | Compound 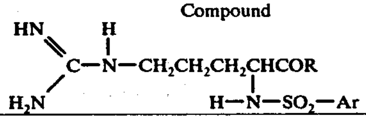 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 77 | 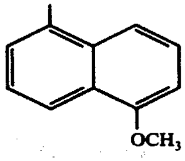 | 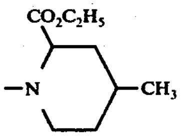 | — | | 2 | " | 57.02<br>56.81 | 6.81<br>6.91 | 12.79<br>12.78 | 3,200<br>1,740<br>1,635 |
| 78 | " | 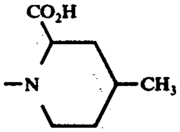 | — | | 2 | powder | 55.47<br>55.31 | 6.40<br>6.68 | 13.48<br>13.21 | 3,350<br>1,620<br>1,150 |
| 79 | 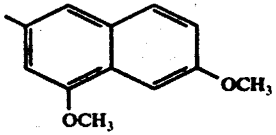 | 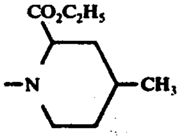 | 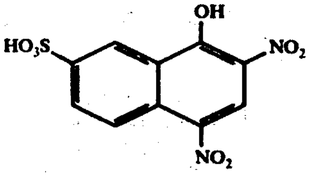 | | 2 | 222-3 | 49.82<br>49.57 | 5.09<br>4.88 | 11.99<br>11.68 | 3,200<br>1,745<br>1,630 |
| 80 | " | 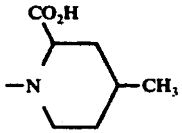 | — | 0.35 | 2 | powder | 54.63<br>54.55 | 6.42<br>6.42 | 12.74<br>12.58 | 3,350<br>(broad)<br>1,620<br>1,150 |
| 81 | 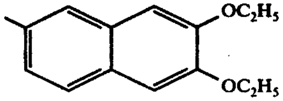 | 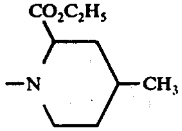 | 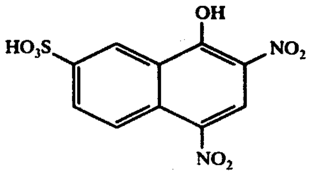 | | 2 | 154-6 | 50.92<br>51.28 | 5.37<br>5.21 | 10.66<br>10.59 | 3,400<br>1,735<br>1,635 |

-continued

| Sample No. | Compound 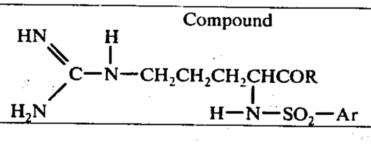 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) (cm⁻¹) |
|---|---|---|---|---|---|---|---|---|---|---|
| 82 | " | 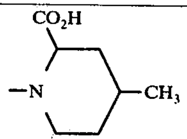 | — | | 2 | powder | 56.13<br>56.11 | 6.80<br>6.85 | 12.12<br>11.95 | 3,300 (broad)<br>1,610<br>1,255 |
| 83 | 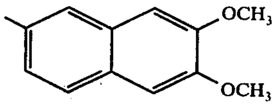 | 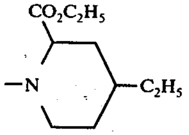 | 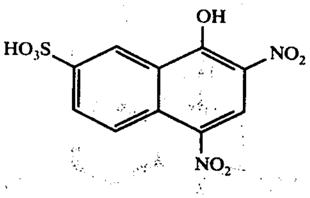 | | 2 | 179–180 | 50.38<br>50.34 | 5.23<br>5.18 | 10.82<br>11.05 | 3,380<br>1,735<br>1,635 |
| 84 | " | 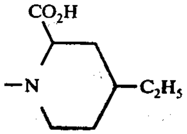 | — | | 2 | powder | 55.40<br>55.71 | 6.62<br>6.48 | 12.43<br>12.53 | 3,360<br>1,620<br>1,150 |
| 85 | 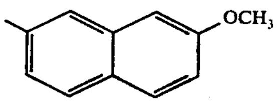 | 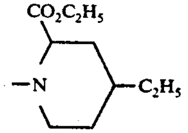 | 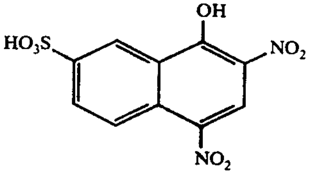 | | 2 | 125<br>(soften) | 50.73<br>50.58 | 5.18<br>5.11 | 11.19<br>10.93 | 3,380<br>1,735<br>1,638 |
| 86 | " | 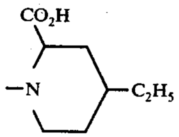 | — | | 2 | powder | 56.26<br>56.41 | 6.61<br>6.48 | 13.12<br>13.27 | 3,360<br>1,620<br>1,158 |
| 87 | 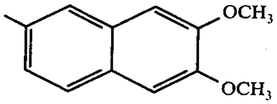 | 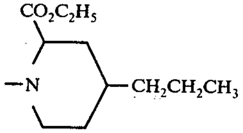 | — | | 2 | " | 57.50<br>57.56 | 7.15<br>7.08 | 11.56<br>11.71 | 3,330<br>2,960<br>1,740<br>1,640 |

-continued
| Sample No. | Compound 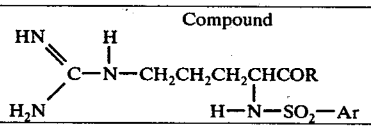 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 88 | " | 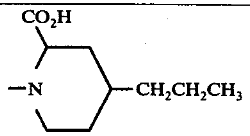 | — | 0.5 | 2 | " | 56.13<br>56.11 | 6.80<br>6.81 | 12.12<br>11.96 | 3,400<br>1,620 |
| 89 | " | 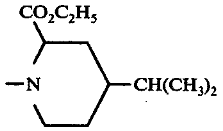 | — | | 2 | " | 57.50<br>57.15 | 7.15<br>7.21 | 11.56<br>11.62 | 3,360<br>2,960<br>1,735 |
| 90 | " | 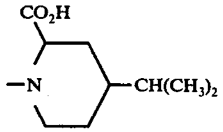 | — | | 2 | " | 56.13<br>56.21 | 6.80<br>6.81 | 12.12<br>12.03 | 3,400<br>1,620<br>1,150 |
| 91 | " | 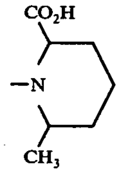 | — | | 2 | " | 54.63<br>54.54 | 6.42<br>6.40 | 12.74<br>12.68 | 3,350<br>1,620<br>1,150 |
| 92 | " | 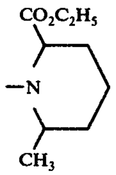 | — | | 2 | powder | 56.13<br>56.08 | 6.80<br>6.91 | 12.12<br>12.08 | 3,250<br>1,740<br>1,640 |
| 93 | 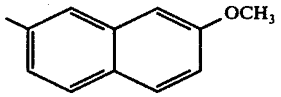 | 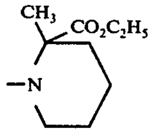 | — | | 2 | " | 57.02<br>56.86 | 6.81<br>6.83 | 12.79<br>12.68 | 3,230<br>1,740<br>1,650 |

-continued

| Sample No. | Compound 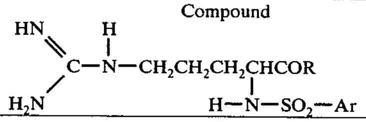 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) (cm⁻¹) |
|---|---|---|---|---|---|---|---|---|---|---|
| 94 | " | 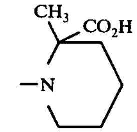 | — | | 2 | " | 54.63<br>54.59 | 6.42<br>6.38 | 12.74<br>12.68 | 3,250<br>1,620<br>1,160 |
| 95 | 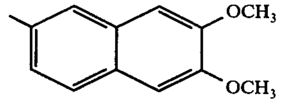 | 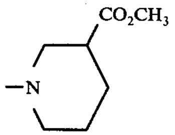 | 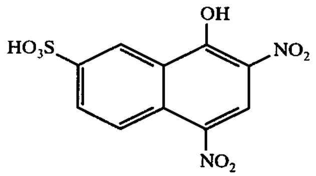 | | 2 | 161-163 | 48.97<br>49.05 | 4.71<br>4.73 | 11.76<br>11.58 | 3,340<br>1,738<br>1,635 |
| 96 | " | 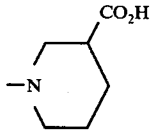 | — | | 2 | powder | 53.82<br>53.68 | 6.21<br>6.08 | 13.08<br>12.85 | 3,370<br>1,635<br>1,255<br>1,155 |
| 97 | 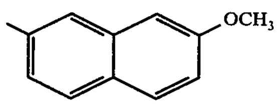 | 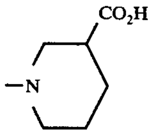 | — | | 2 | " | 54.64<br>54.58 | 6.18<br>6.09 | 13.85<br>13.93 | 3,370<br>1,640<br>1,260<br>1,155 |
| 98 | 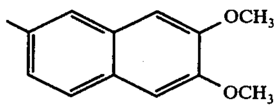 | 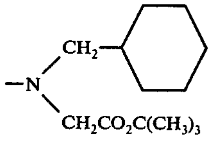 | 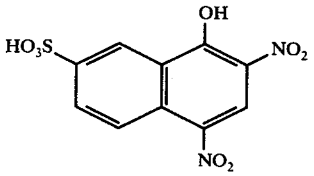 | | 1 | 165-168 (dec.) | 51.94<br>51.50 | 5.64<br>5.41 | 10.34<br>10.10 | 3,390<br>3,220<br>1,740 |
| 99 | " | 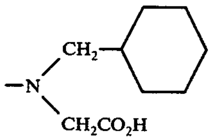 | — | | 1 | powder | 56.13<br>56.00 | 6.81<br>6.73 | 12.12<br>12.01 | 3,350 (broad)<br>1,640 |

-continued

Compound 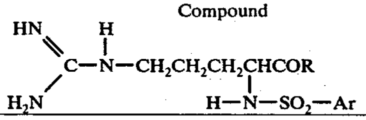 (I)

| Sample No. | Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) (cm⁻¹) |
|---|---|---|---|---|---|---|---|---|---|---|
| 100 | " | 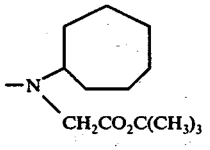 | 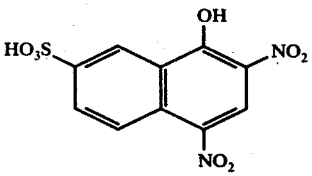 | | 1 | 178–181 (dec.) | 51.94<br>52.24 | 5.64<br>5.60 | 10.34<br>10.28 | 3,400<br>3,200<br>1,735 |
| 101 | " | 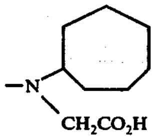 | — | | 1 | powder | 56.13<br>56.28 | 6.81<br>6.59 | 12.12<br>12.31 | 3,350<br>(broad)<br>1,640 |
| 102 | 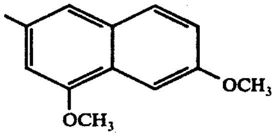 | 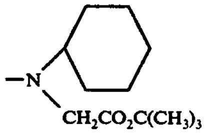 | 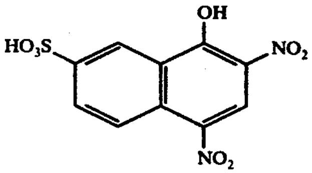 | | 1 | 162–165 (dec.) | 51.43<br>51.28 | 5.50<br>5.21 | 10.50<br>10.21 | 3,370<br>3,200<br>1,730 |
| 103 | " | 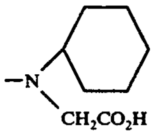 | — | | 1 | powder | 55.40<br>55.28 | 6.62<br>6.32 | 12.43<br>12.03 | 3,300<br>(broad)<br>1,610<br>(broad) |
| 104 | 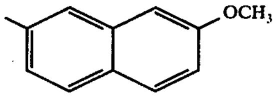 | 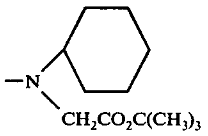 | 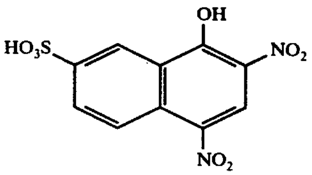 | | 1 | 158–160 (dec.) | 52.75<br>52.56 | 5.56<br>5.43 | 11.04<br>10.97 | 3,405<br>3,220<br>1,740 |

-continued

| Sample No. | Compound 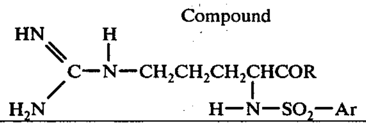 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 105 | " | 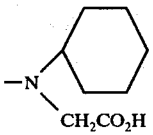 | — | | 1 | powder | 56.26<br>56.01 | 6.61<br>6.49 | 13.13<br>13.21 | 3,320<br>(broad)<br>1,640 |
| 106 | 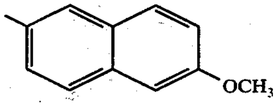 | 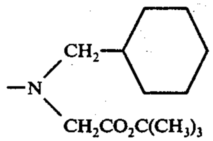 | 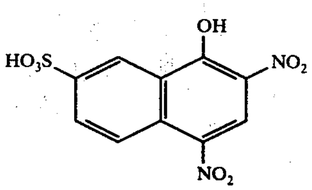 | | 1 | 160-163<br>(dec.) | 52.33<br>52.03 | 5.60<br>5.30 | 10.68<br>10.28 | 3,400<br>3,210<br>1,730 |
| 107 | " | 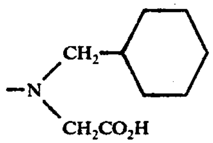 | — | | 1 | powder | 57.02<br>57.39 | 6.81<br>6.21 | 12.79<br>12.38 | 3,350<br>(broad)<br>1,620 |
| 108 | 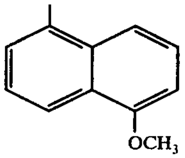 | 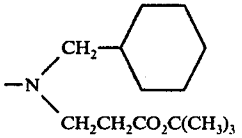 | 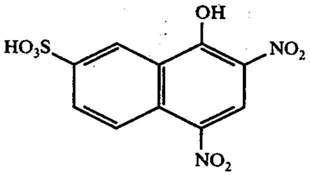 | | 1 | 152-155<br>(dec.) | 52.83<br>52.53 | 5.73<br>5.72 | 10.52<br>10.29 | 3,390<br>3,205<br>1,730 |
| 109 | " | 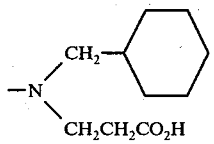 | — | | 1 | powder | 57.73<br>57.51 | 7.00<br>7.23 | 12.47<br>12.28 | 3,370<br>1,630 |

-continued
| Sample No. | Compound 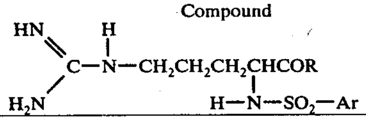 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 110 | 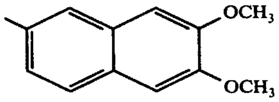 | 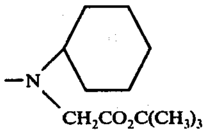 | 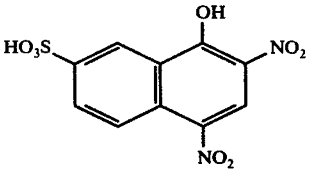 | | 1 | 170–172 (dec.) | 51.43<br>51.09 | 5.50<br>5.45 | 10.50<br>10.28 | 3,380<br>3,220<br>1,740 |
| 111 | " | 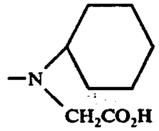 | — | 5 | 1 | powder | 55.40<br>55.30 | 6.62<br>6.28 | 12.43<br>12.11 | 3,400–3,200 (broad)<br>1,600 |
| 112 | " | 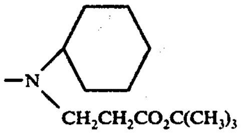 | 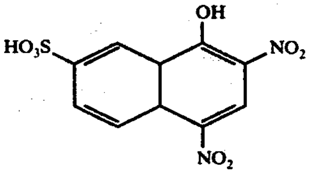 | | 1 | 155–158 (dec.) | 51.94<br>52.29 | 5.64<br>5.63 | 10.34<br>10.00 | 3,380<br>3,200<br>1,730 |
| 113 | " | 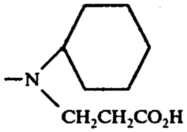 | — | | 1 | powder | 56.13<br>56.40 | 6.81<br>6.61 | 12.12<br>12.00 | 3,200–3,400 (broad)<br>1,600 |
| 114 | " | 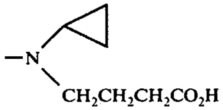 | — | | 1 | " | 54.63<br>54.40 | 6.42<br>6.30 | 12.74<br>12.50 | 3,200–3,400 (broad)<br>1,600 |

-continued
Compound
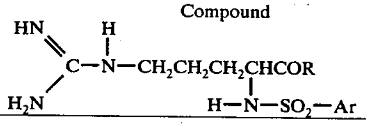 (I)
| Sample No. | Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) (cm$^{-1}$) |
|---|---|---|---|---|---|---|---|---|---|---|
| 115 | " | 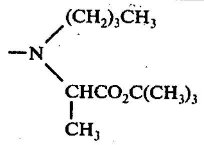 | 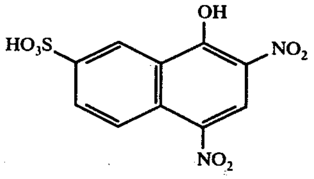 | | 1 | 165–170 (dec.) | 50.81<br>50.68 | 5.58<br>5.43 | 10.64<br>10.31 | 3,380<br>3,200<br>1,740 |
| 116 | " | 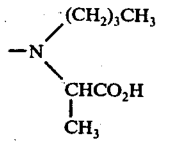 | — | | 1 | powder | 54.43<br>54.70 | 6.76<br>6.71 | 12.70<br>12.35 | 3,400<br>1,590 |
| 117 | " | 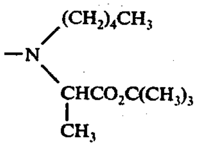 | 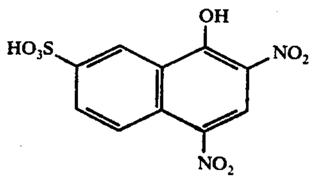 | | 1 | 164–166 | 51.33<br>51.60 | 5.71<br>5.38 | 10.48<br>10.25 | 3,360<br>3,200<br>1,735 |
| 118 | " | 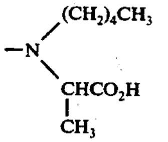 | — | 2.0 | 1 | powder | 55.21<br>55.00 | 6.95<br>6.30 | 12.38<br>12.40 | 3,400–3,200 (broad)<br>1,570 |
| 119 | " | 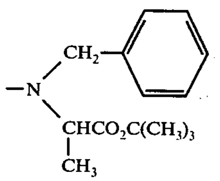 | 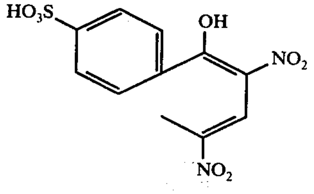 | | 1 | 168–172 | 52.77<br>52.54 | 5.17<br>4.98 | 10.26<br>10.21 | 3,380<br>3,180<br>1,740 |

-continued
| Sample No. | Compound 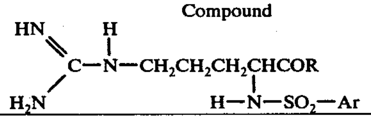 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 120 | 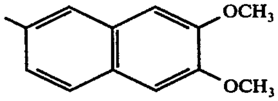 | 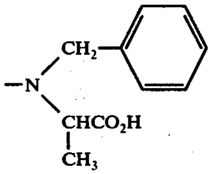 | — | 2.5 | 1 | powder | 57.42<br>57.35 | 6.02<br>5.84 | 11.96<br>12.00 | 3,350-3,160 (broad)<br>1,600 |
| 121 | " | 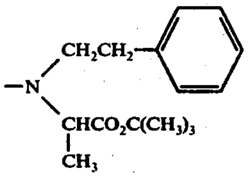 | 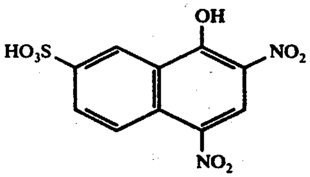 | | 1 | 130-135 | 53.25<br>53.08 | 5.30<br>5.29 | 10.11<br>10.29 | 3,400<br>3,200<br>1,730 |
| 122 | " | 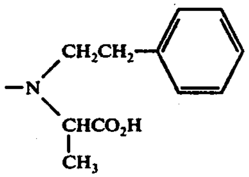 | — | 1.5 | 1 | powder | 58.08<br>57.84 | 6.22<br>6.13 | 11.68<br>11.46 | 3,360<br>3,160<br>1,600 |
| 123 | " | 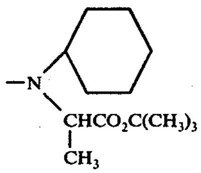 | 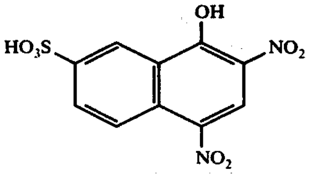 | | 1 | 158-163 (dec.) | 51.95<br>51.80 | 5.64<br>5.38 | 10.34<br>10.30 | 3,360<br>3,200<br>1,740 |

-continued
Compound 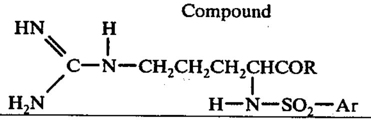 (I)
| Sample No. | Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) (cm⁻¹) |
|---|---|---|---|---|---|---|---|---|---|---|
| 124 | " | 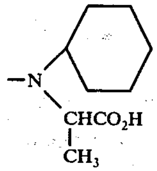 | — | | 1 | powder | 56.14<br>55.98 | 6.81<br>6.79 | 12.13<br>12.35 | 3,380–3,200 (broad)<br>1,625 |
| 125 | 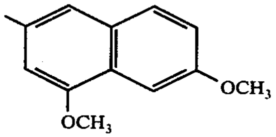 | 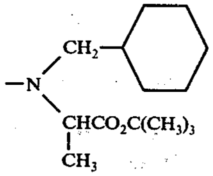 | 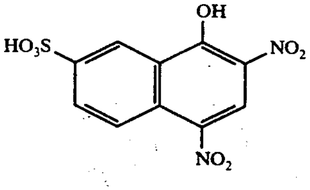 | | 1 | 160–163 (dec.) | 52.44<br>52.39 | 5.76<br>5.58 | 10.19<br>10.00 | 3,400<br>3,200<br>1,740 |
| 126 | " | 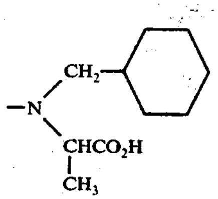 | — | 4.5 | 1 | powder | 56.84<br>56.72 | 6.99<br>6.80 | 11.84<br>11.76 | 3,380–3,250 (broad)<br>1,595 |
| 127 | 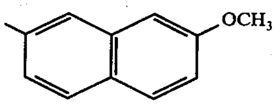 | 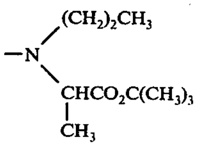 | " | | 1 | 160–165 (dec.) | 50.62<br>50.39 | 5.40<br>5.28 | 11.17<br>11.15 | 3,400<br>3,210<br>1,740 |
| 128 | " | 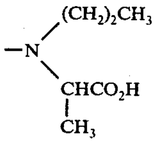 | — | | 1 | powder | 54.43<br>54.27 | 6.55<br>6.28 | 13.80<br>13.59 | 3,280<br>1,590 |

-continued

| Sample No. | Compound 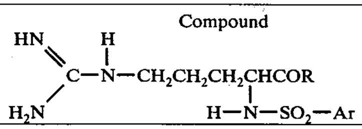 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 129 | 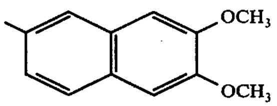 | 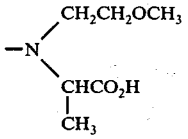 | — | 5 | 1 | " | 52.07<br>51.89 | 6.37<br>6.39 | 12.65<br>12.51 | 3,360<br>3,200<br>1,600 |
| 130 | 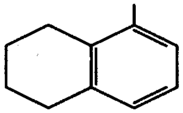 | 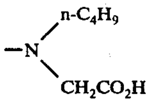 | — | 20 | 5 | 210–213 | 54.86<br>54.72 | 7.33<br>7.21 | 14.54<br>14.27 | 3,350<br>1,630 |
| 131 | 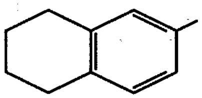 | 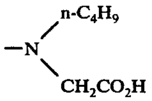 | — | | 5 | 120–130 | 55.73<br>55.82 | 7.52<br>7.50 | 14.13<br>14.01 | 3,350<br>1,630 |
| 132 | 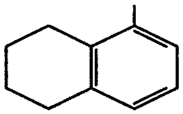 | 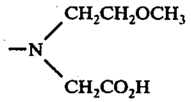 | — | 10 | 5 | 108–110 | 52.15<br>52.21 | 6.88<br>6.71 | 14.48<br>14.52 | 3,300<br>(broad)<br>1,630 |
| 133 | 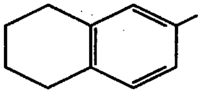 | 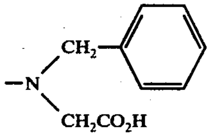 | — | 30 | 5 | powder | 58.23<br>58.01 | 6.45<br>6.35 | 13.58<br>13.46 | 3,300<br>(broad)<br>1,635 |
| 134 | 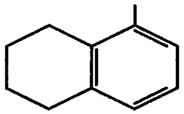 | 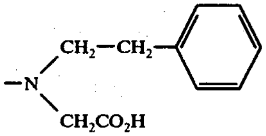 | — | | 5 | powder | 58.96<br>58.91 | 6.66<br>6.79 | 13.22<br>13.15 | 3,200<br>(broad)<br>1,635 |

-continued
| Sample No. | Compound 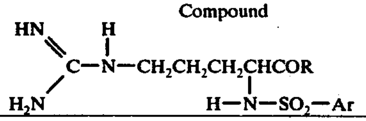 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 135 | 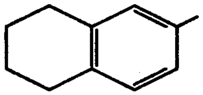 | 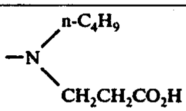 | — | | 5 | " | 55.73 | 7.52 | 14.13 | 3,300 (broad) |
| | | | | | | | 55.81 | 7.40 | 14.10 | 1,630 |
| 136 | " | 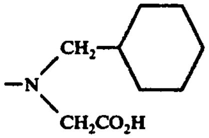 | — | | 5 | 170-173 | 57.56 | 7.54 | 13.43 | 3,335 |
| | | | | | | | 57.41 | 7.39 | 13.50 | 1,630 |
| 137 | 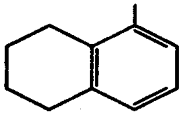 | 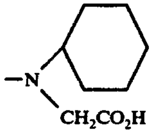 | — | | 5 | powder | 56.78 | 7.35 | 13.80 | 3,200 (broad) |
| | | | | | | | 56.85 | 7.29 | 13.71 | 1,630 |
| 138 | 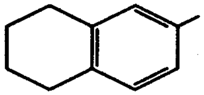 | 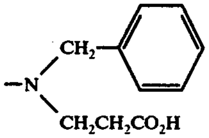 | — | | 5 | " | 58.96 | 6.66 | 13.22 | 3,300 (broad) |
| | | | | | | | 58.79 | 6.51 | 13.19 | 1,630 |
| 139 | 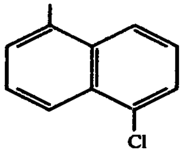 | 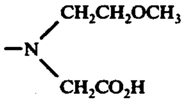 | — | | 5 | 142-145 | 49.07 | 5.49 | 13.63 | 3,150 |
| | | | | | | | 48.90 | 5.38 | 13.42 | 1,620 |
| 140 | 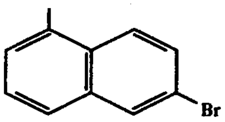 | 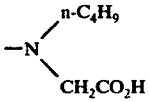 | — | | 5 | powder | 47.47 | 5.43 | 12.58 | 3,150 |
| | | | | | | | 47.29 | 5.31 | 12.39 | 1,630 |

-continued

Compound 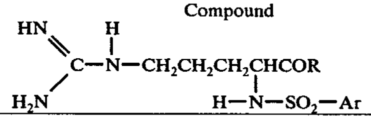 (I)

| Sample No. | Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 141 | 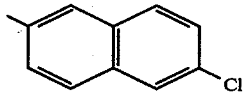 | 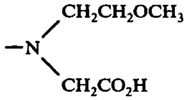 | — | | 5 | powder | 49.07<br>49.12 | 5.49<br>5.28 | 13.63<br>13.59 | 3,150<br>1,630 |
| 142 | 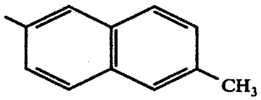 | 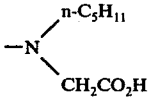 | — | | 5 | 123–130 | 57.01<br>56.88 | 6.98<br>6.71 | 13.85<br>13.65 | 3,300<br>1,635 |
| 143 | 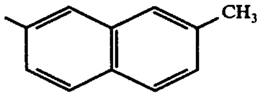 | 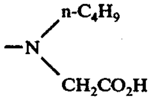 | — | 0.3 | 5 | powder | 56.19<br>56.00 | 6.77<br>6.50 | 14.25<br>14.00 | 3,300<br>3,150<br>1,630 |
| 144 | " | 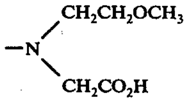 | — | 0.2 | 5 | " | 53.53<br>53.24 | 6.33<br>6.19 | 14.19<br>13.99 | 3,300<br>(broad)<br>1,630 |
| 145 | " | 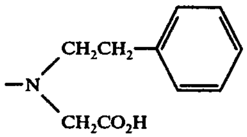 | — | | 5 | " | 60.09<br>59.79 | 6.16<br>6.02 | 12.93<br>12.61 | 3,300<br>(broad)<br>1,630 |
| 146 | " | 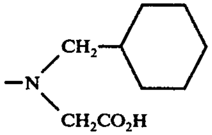 | — | 14 | 5 | " | 58.73<br>58.66 | 7.01<br>6.90 | 13.17<br>12.91 | 3,380<br>1,635 |
| 147 | 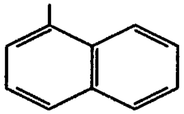 | 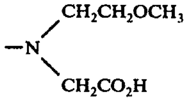 | — | | 5 | 147–150 | 52.59<br>52.31 | 6.10<br>6.01 | 14.61<br>14.33 | 3,380<br>1,640 |

-continued
| Sample No. | Compound 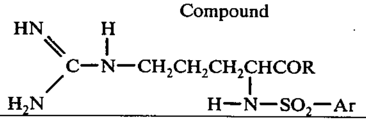 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 148 | " | 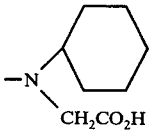 | — | | 5 | powder | 57.23<br>56.98 | 6.61<br>6.33 | 13.91<br>13.81 | 3,300 (broad)<br>1,630 |
| 149 | 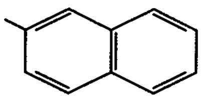 | 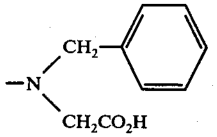 | — | | 5 | " | 58.69<br>58.79 | 5.71<br>5.55 | 13.69<br>13.39 | 3,300 (broad)<br>3,150<br>1,630 |
| 150 | " | 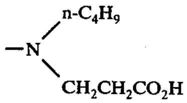 | — | | 5 | " | 56.19<br>55.95 | 6.77<br>6.58 | 14.25<br>13.97 | 3,190 (broad)<br>1,620 |
| 151 | 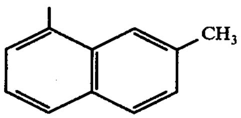 | 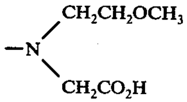 | — | 20 | 5 | 130-135 | 53.53<br>53.28 | 6.33<br>6.19 | 14.19<br>13.97 | 3,350<br>1,640 |
| 152 | 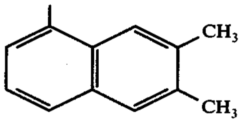 | " | — | 10 | 5 | 152-157 | 54.42<br>54.28 | 6.55<br>6.32 | 13.80<br>13.59 | 3,350<br>1,635 |
| 153 | 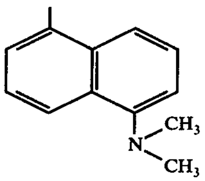 | 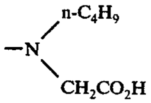 | — | 4 | 5 | powder | 55.36<br>55.10 | 6.97<br>6.76 | 16.14<br>16.07 | 3,380<br>1,630 |

-continued

| Sample No. | Compound 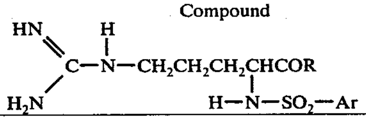 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 154 | ″ | 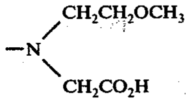 | — | | 5 | ″ | 52.86<br>52.71 | 6.56<br>6.29 | 16.08<br>16.07 | |
| 155 | 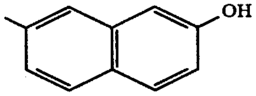 | ″ | — | | 5 | ″ | 50.90<br>50.81 | 5.90<br>5.70 | 14.13<br>13.89 | 3,180 (broad)<br>1,630 |
| 156 | 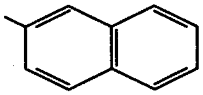 | 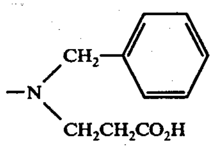 | — | | 5 | ″ | 59.41<br>59.22 | 5.95<br>5.73 | 13.33<br>13.28 | 3,170 (broad)<br>1,620 |
| 157 | ″ | 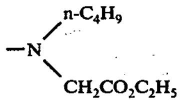 | HCl | | 6 | ″ | 53.17<br>52.89 | 6.69<br>6.52 | 12.92<br>12.74 | |
| 158 | ″ | 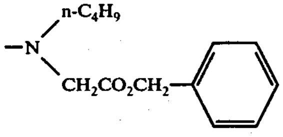 | HCl | | 6 | ″ | 57.66<br>57.31 | 6.34<br>6.14 | 11.59<br>11.16 | |
| 159 | ″ | 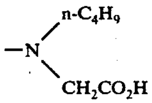 | — | | 5 | ″ | 55.33<br>55.26 | 6.54<br>6.62 | 14.67<br>14.58 | 3,200 (broad)<br>1,630 |
| 160 | 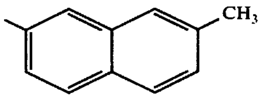 | 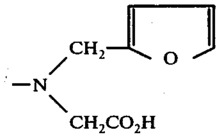 | — | 0.25 | 1 | ″ | 55.47<br>55.75 | 6.40<br>6.19 | 13.48<br>13.26 | 3,350 (broad)<br>1,630<br>1,380 |

-continued

| Sample No. | Compound 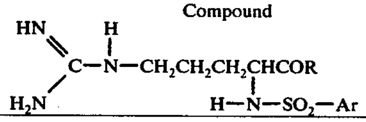 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) (cm$^{-1}$) |
|---|---|---|---|---|---|---|---|---|---|---|
| 161 | " | 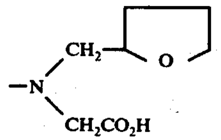 | — | 0.2 | 5 | " | 55.05<br>55.28 | 7.12<br>7.00 | 13.38<br>13.12 | 3,200 (broad)<br>1,635<br>1,380 |
| 162 | 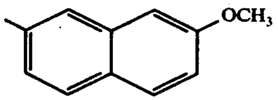 | 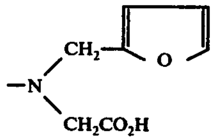 | — | 0.2 | 1 | " | 54.22<br>53.98 | 5.50<br>5.55 | 13.18<br>13.24 | 3,320 (broad)<br>1,630<br>1,380 |
| 163 | " | 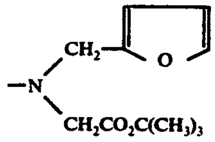 | — | | 1 | " | 57.22<br>57.23 | 6.35<br>6.36 | 11.92<br>12.08 | 3,400 (broad)<br>1,740<br>1,620 |
| 164 | " | 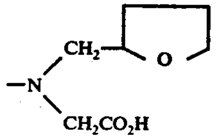 | — | 0.15 | 1 | " | 53.82<br>53.78 | 6.21<br>6.19 | 13.08<br>12.86 | 3,360 (broad)<br>1,625<br>1,380 |
| 165 | " | 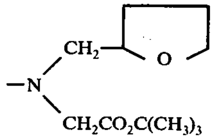 | — | | 1 | " | 56.83<br>56.95 | 6.98<br>6.83 | 11.84<br>11.98 | 3,400 (broad)<br>1,735<br>1,630 |

-continued
| Sample No. | Compound 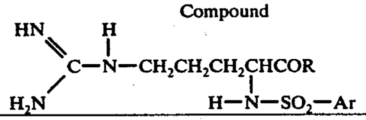 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 166 | 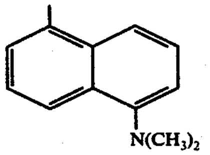 | 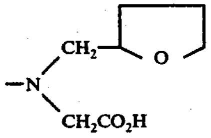 | $CH_3CO_2H$ | | 5 | " | 53.28<br>53.13 | 6.62<br>6.82 | 13.81<br>13.71 | 3,320 (broad) 1,630 1,140 |
| 167 | 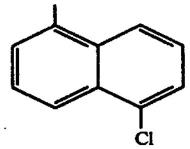 | 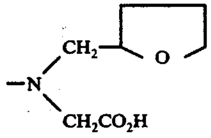 | — | | 5 | " | 51.15<br>50.86 | 5.60<br>5.66 | 12.97<br>12.87 | 3,320 (broad) 1,630 1,380 |
| 168 | 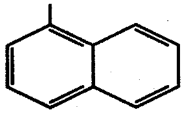 | 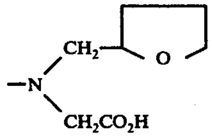 | — | | 5 | " | 54.64<br>53.36 | 6.18<br>6.00 | 13.85<br>13.58 | 3,350 (broad) 1,640 1,390 |
| 169 | 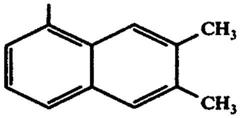 | " | — | | 5 | " | 56.27<br>55.98 | 6.61<br>6.78 | 13.12<br>13.24 | 3,350 (broad) 1,630 1,380 1,140 |
| 170 | 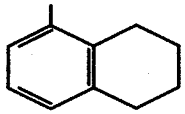 | " | — | | 5 | " | 54.21<br>54.36 | 6.92<br>6.93 | 13.74<br>13.76 | 3,300 (broad) 1,625 1,380 1,160 |
| 171 | 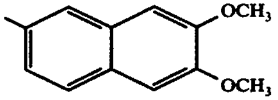 | " | — | | 1, 2 | " | 53.08<br>52.86 | 6.24<br>6.33 | 12.38<br>12.41 | 3,300 (broad) 1,640 1,160 |

-continued

| Sample No. | Compound 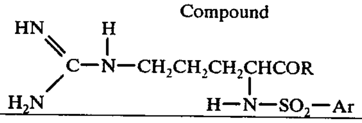 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 172 | " | 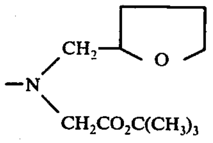 | — | | 1 | " | 56.02<br>55.83 | 6.97<br>6.88 | 11.27<br>11.28 | 3,400 (broad) 1,745 1,620 |
| 173 | 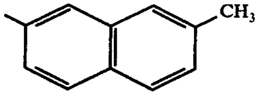 | 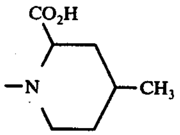 | — | 0.2 | 3 | " | 57.23<br>56.89 | 6.61<br>6.50 | 13.91<br>13.70 | 3,390 (broad) 1,625 |
| 174 | " | 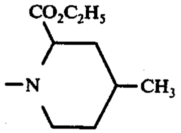 | $CH_3COOH$ | | 3 | " | 56.83<br>56.72 | 6.98<br>6.81 | 11.84<br>11.56 | 3,400 (broad) 1,735 1,640 |
| 175 | " | 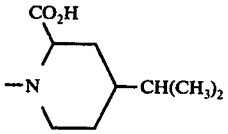 | — | 0.1 | 2 | " | 58.73<br>58.52 | 7.01<br>6.77 | 13.17<br>13.00 | 3,380 (broad) 1,620 |
| 176 | " | 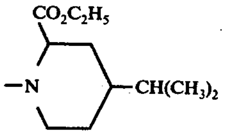 | $\frac{1}{2}H_2SO_3$ | | 2 | powder | 55.98<br>55.69 | 7.05<br>7.21 | 11.66<br>11.38 | 3,400 (broad) 1,730 1,635 |
| 177 | 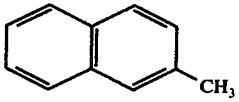 | 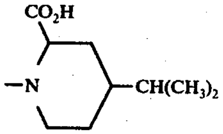 | — | | 3 | " | 58.73<br>58.81 | 7.02<br>7.03 | 13.17<br>13.17 | 3,300 (broad) 1,615 1.380 |

-continued

| Sample No. | Compound 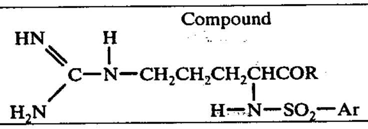 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 178 | " | 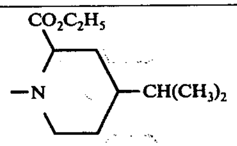 | $CH_3COOH$ | | 3 | " | 58.13<br>57.98 | 7.32<br>7.56 | 11.30<br>11.28 | 3,380 (broad) 1,730 1,630 |
| 179 | 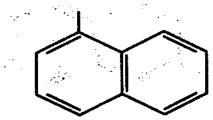 | 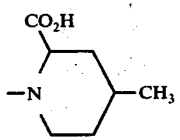 | — | 1 | 3 | " | 56.42<br>56.38 | 6.38<br>6.52 | 14.31<br>14.53 | 3,350 (broad) 1,620 1,160 |
| 180 | " | 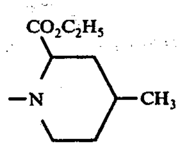 | $CH_3COOH$ | | 3 | " | 56.13<br>56.08 | 6.80<br>6.83 | 12.12<br>12.12 | 3,400 (broad) 1,740 1,630 |
| 181 | 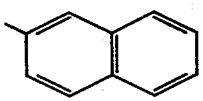 | 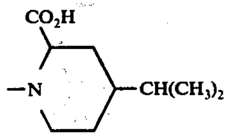 | — | 0.5 | 3 | " | 58.00<br>57.83 | 6.82<br>6.77 | 13.53<br>13.63 | 3,350 (broad) 1,620 1,160 |
| 182 | " | 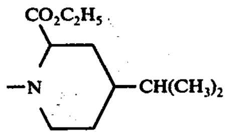 | $CH_3COOH$ | | 3 | " | 57.50<br>57.61 | 7.15<br>7.11 | 11.56<br>11.81 | 3,350 (broad) 1,730 1,620 |
| 183 | 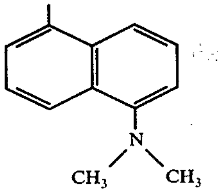 | 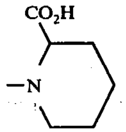 | — | 0.35 | 3 | " | 55.58<br>55.62 | 6.61<br>6.81 | 16.21<br>16.03 | 3,350 (broad) 1,620 1,140 |

-continued
| Sample No. | Compound 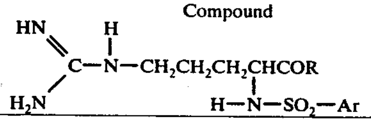 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 184 | 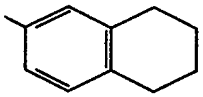 | 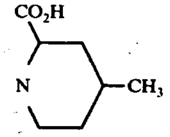 | — | | 3 | " | 55.96<br>56.12 | 7.15<br>7.28 | 14.19<br>14.07 | 3,350 (broad) 1,620 1,150 |
| 185 | " | 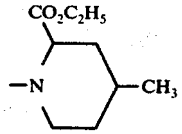 | $CH_3COOH$ | | 3 | " | 55.74<br>55.90 | 7.45<br>7.51 | 12.04<br>12.18 | 3,400 (broad) 1,730 1,625 |
| 186 | 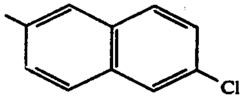 | 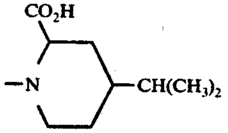 | — | | 3 | " | 54.38<br>54.08 | 6.21<br>5.91 | 12.69<br>12.39 | 3,300 (broad) 1,625 |
| 187 | 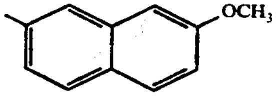 | 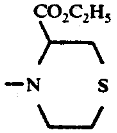 | — | | 2 | " | 52.25<br>52.36 | 6.03<br>5.98 | 12.70<br>12.51 | 3,400 1,735 1,640 1,160 |
| 188 | " | 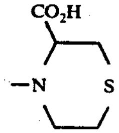 | — | | 2 | " | 50.46<br>50.61 | 5.58<br>5.63 | 13.38<br>13.40 | 3,380 1,620 1,380 1,155 |
| 189 | " | 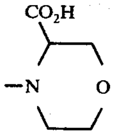 | — | 2 | 3 | " | 52.06<br>52.31 | 5.76<br>5.81 | 13.80<br>13.51 | 3,320 1,620 1,390 1,155 |

-continued

| Sample No. | Compound 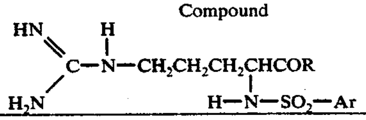 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 190 | " | 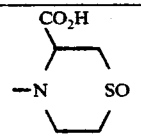 | — | | 2 | " | 48.96<br>49.13 | 5.42<br>5.38 | 12.98<br>12.75 | 3,350<br>1,620<br>1,380<br>1,150 |
| 191 | 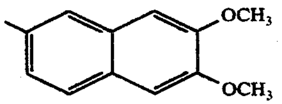 | 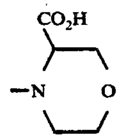 | — | 5 | 2 | " | 51.38<br>51.45 | 5.81<br>5.86 | 13.03<br>13.12 | 3,350<br>1,630<br>1,255<br>1,150 |
| 192 | 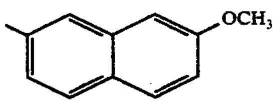 | 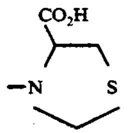 | — | | 2 | " | 49.50<br>49.31 | 5.34<br>5.40 | 13.75<br>13.68 | 3,350<br>3,200<br>1,622 |
| 193 | 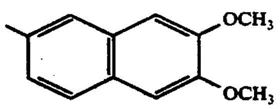 | 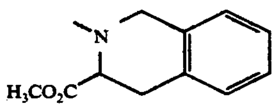 | — | | 2 | " | 58.27<br>58.45 | 5.90<br>6.03 | 11.72<br>11.53 | 3,350<br>1,740<br>1,640<br>1,260<br>1,160 |
| 194 | " | 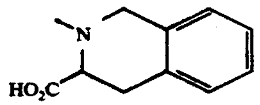 | — | 2 | 2 | " | 57.62<br>57.68 | 5.70<br>5.55 | 12.00<br>11.73 | 3,300<br>(broad)<br>1,620<br>1,250<br>1,150 |
| 195 | " | 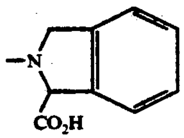 | — | 1.5 | 3 | " | 56.93<br>57.12 | 5.49<br>5.43 | 12.30<br>12.14 | 3,360<br>1,625<br>1,260<br>1,150 |
| 196 | " | 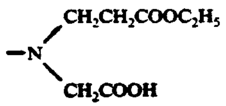 | — | 6.5 | 1 | " | 54.63<br>54.28 | 6.42<br>6.31 | 12.74<br>12.53 | 3,350<br>(broad)<br>1,740 |

-continued
Compound
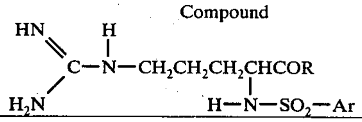 (I)
| Sample No. | Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 197 | " | 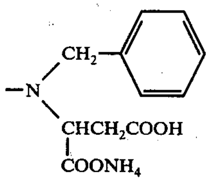 | — | | 2 | " | 53.86<br>54.16 | 5.92<br>5.62 | 13.00<br>12.70 | 3,100 (broad) 1,620 |
| 198 | " | 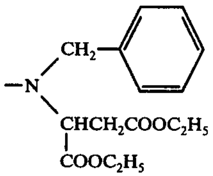 | $\frac{1}{2}H_2SO_3$ | | 2 | " | 54.53<br>54.23 | 6.10<br>5.80 | 9.64<br>9.34 | 1,720 1,630 (broad) |
| 199 | 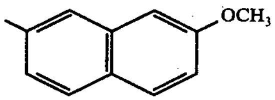 | 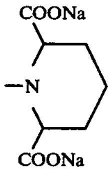 | — | | 2 | " | 48.55<br>48.31 | 4.93<br>4.64 | 11.80<br>11.53 | 3,300 (broad) 1,620 |
| 200 | 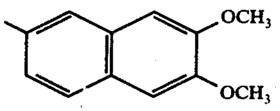 | 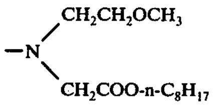 | HCl | 2 | 6 | " | 54.10<br>53.81 | 7.32<br>7.13 | 10.18<br>9.93 | 3,180 (broad) 1,740 1,630 |
| 201 | " | 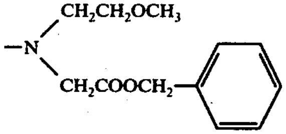 | — | | 2 | " | 57.22<br>56.98 | 6.24<br>6.18 | 11.12<br>11.31 | 3,300 3,150 1,740 1,650 |

-continued

| Sample No. | Compound 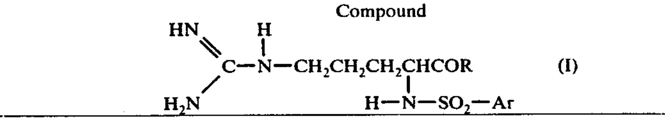 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 202 | " | 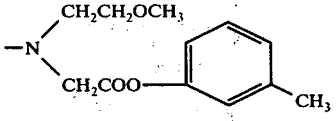 | HCl | 20 | 6 | " | 54.09<br>53.83 | 6.05<br>5.97 | 10.51<br>10.36 | 3,250<br>3,100<br>1,740<br>1,640 |
| 203 | " | 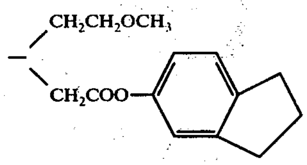 | HCl | 30 | 6 | " | 55.53<br>55.37 | 6.12<br>6.01 | 10.12<br>10.01 | 3,350<br>3,150<br>1,740<br>1,650 |
| 204 | 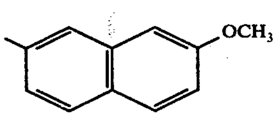 | 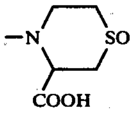 | — | 4.5 | 2 | powder | 48.96<br>49.13 | 5.42<br>5.36 | 12.98<br>13.01 | 3,350<br>1,620<br>1,380 |
| 205 | " | 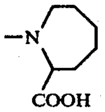 | — | 2.5 | 2 | " | 54.64<br>54.63 | 6.42<br>6.56 | 12.74<br>13.01 | 3,360<br>2,940<br>1,620<br>1.380 |
| 206 | 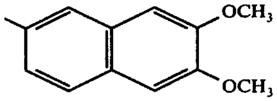 | 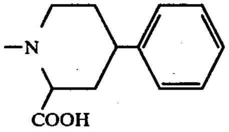 | — | 12 | 2 | " | 59.89<br>59.65 | 4.52<br>4.63 | 11.64<br>11.81 | 3,360<br>1,620<br>1,255<br>1,150 |
| 207 | " | 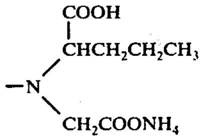 | — | 55 | 2 | " | 50.15<br>49.91 | 6.41<br>6.35 | 14.04<br>13.83 | 3,280<br>1,620 |

-continued
| Sample No. | Compound 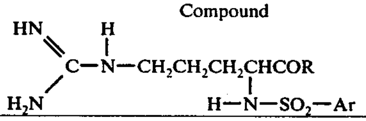 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) (cm⁻¹) |
|---|---|---|---|---|---|---|---|---|---|---|
| 208 | " | 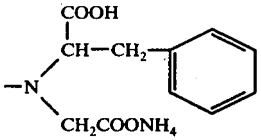 | — | | 2 | " | 53.85<br>53.61 | 5.93<br>5.76 | 13.00<br>12.84 | 3,320<br>1,610 |
| 209 | " | 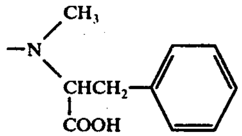 | — | 2 | 2 | " | 57.42<br>57.37 | 6.02<br>5.86 | 11.96<br>11.74 | 3,300 (broad)<br>1,600 |
| 210 | 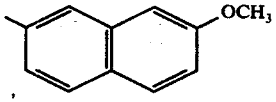 | 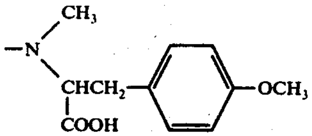 | — | | 2 | " | 57.41<br>57.33 | 6.03<br>5.94 | 11.96<br>11.73 | 3,300<br>1,610 |
| 211 | " | 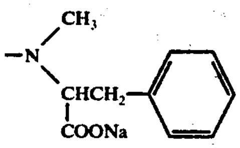 | — | 2.5 | 2 | " | 53.98<br>53.74 | 5.38<br>5.33 | 11.66<br>11.74 | 3,350<br>1,630 |
| 212 | 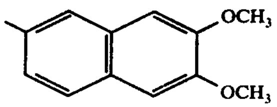 | 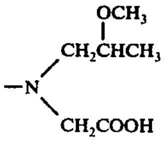 | — | 6.5 | 2 | " | 52.06<br>52.40 | 6.38<br>6.37 | 12.65<br>12.73 | 3,350 (broad)<br>1,620 |
| 213 | " | 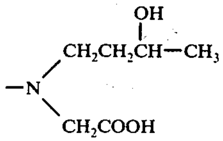 | — | | 2 | " | 52.07<br>51.95 | 6.37<br>6.27 | 12.65<br>12.84 | 3,350 (broad)<br>1,620 |

-continued

| Sample No. | Compound 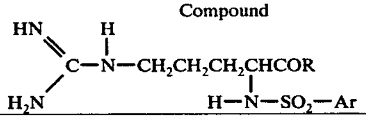 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) (cm$^{-1}$) |
|---|---|---|---|---|---|---|---|---|---|---|
| 214 | " | 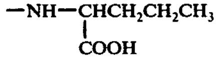 | — | 15 | 2 | " | 52.75<br>52.68 | 6.36<br>6.34 | 13.38<br>13.41 | 3,380 (broad)<br>1,620 |
| 215 | " | 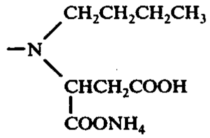 | — | | 2 | " | 50.97<br>50.67 | 6.58<br>6.61 | 13.72<br>13.39 | 3,200 (broad)<br>1,610 (broad) |
| 216 | " | 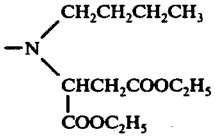 | $\frac{1}{2}H_2SO_3$ | | 2 | " | 52.01<br>51.77 | 6.69<br>6.50 | 10.11<br>10.00 | 1,725<br>1,620 |
| 217 | 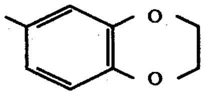 | 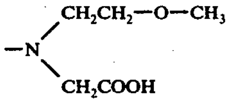 | — | | 5 | " | 46.81<br>46.63 | 6.00<br>5.94 | 14.37<br>14.23 | 3,400<br>3,300<br>1,630 |
| 218 | 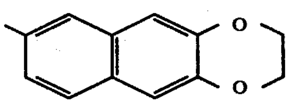 | 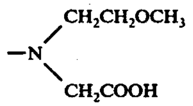 | — | | 5 | " | 51.38<br>51.24 | 5.82<br>5.79 | 13.03<br>12.87 | 3,380<br>3,300<br>1,630 |
| 219 | 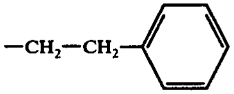 | 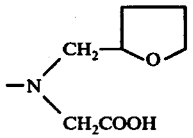 | — | | 1 | " | 52.15<br>52.03 | 6.88<br>6.73 | 14.48<br>14.68 | 3,355<br>1,630<br>1,380<br>1,305 |
| 220 | 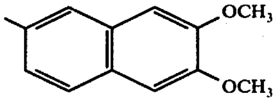 | 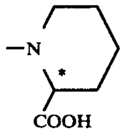 (D) | $2H_2O$ | 2 | 2 | 195-198 | 50.42<br>50.48 | 6.54<br>6.16 | 12.25<br>12.31 | 3,320<br>1,620 |

-continued

| Sample No. | Compound 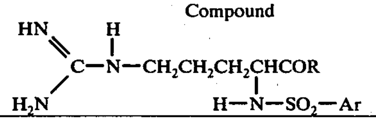 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 221 | " | 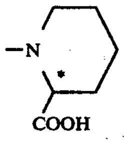 (L) | ½$H_2O$ | 15 | 2 | 229-233 | 52.94<br>52.73 | 6.30<br>6.15 | 12.87<br>12.93 | 3,350<br>1,620 |
| 222 | 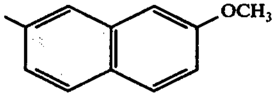 | 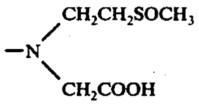 | — | 6.5 | 1 | powder | 48.78<br>48.54 | 5.77<br>5.76 | 12.93<br>13.15 | 3,320<br>1,620<br>1,390 |
| 223 | 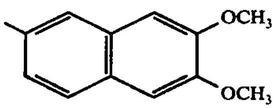 | 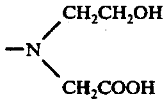 | — | | 1 | " | 50.27<br>50.11 | 5.95<br>5.87 | 13.33<br>13.34 | 3,390<br>1,630<br>1,260<br>1,160 |
| 224 | 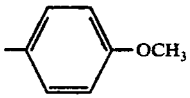 | 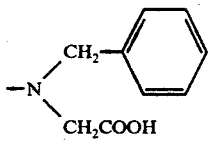 | — | | 5 | " | 53.76<br>53.66 | 5.95<br>5.83 | 14.25<br>14.19 | 3,400<br>3,200<br>1,635 |
| 225 | 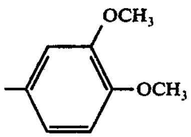 | 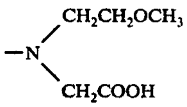 | — | | 5 | " | 46.62<br>46.53 | 6.38<br>6.21 | 14.31<br>14.43 | 3,350<br>3,150<br>1,630 |
| 226 | 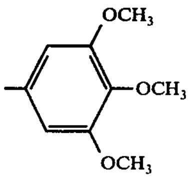 | 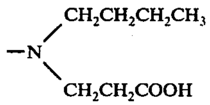 | — | | 5 | " | 49.71<br>49.84 | 7.02<br>7.26 | 13.18<br>13.36 | 3,250<br>(broad)<br>3,150<br>1,630 |

-continued
| Sample No. | Compound 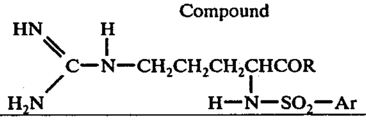 (I) Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 227 | " | 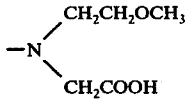 | — | | 5 | " | 46.24<br>46.31 | 6.40<br>6.53 | 13.48<br>13.41 | 3,320<br>3,150<br>1,630 |
| 228 | 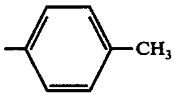 | 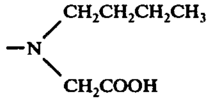 | HCl | | 1 | " | 47.74<br>47.53 | 6.75<br>6.51 | 14.65<br>14.41 | 3,340<br>3,180<br>1,640 |
| 229 | 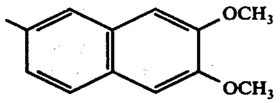 | 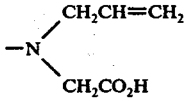 | | | 1 | | ,5278<br>52.79 | 6.00<br>5.87 | 13.43<br>13.28 | 3,350<br>3,150<br>1,620 |
| 230 | " | 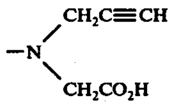 | | | 1 | | 53.16 | 5.64 | 13.48 | |
| 231 | 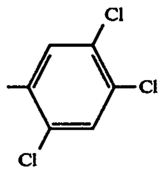 | 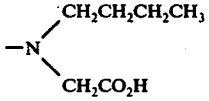 | | | 5 | | 40.71<br>40.60 | 4.95<br>4.78 | 13.19<br>13.03 | 3,360<br>3,150<br>1,620 |
| 232 | 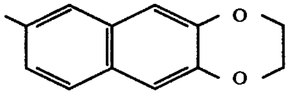 | 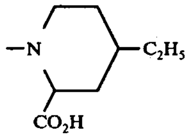 | — | | 3 | " | 55.59<br>55.54 | 6.29<br>6.14 | 12.47<br>12.35 | 3,350<br>3,150<br>1,625 |

-continued
Compound 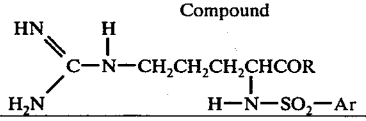 (I)
| Sample No. | Ar | R | Addition moiety | Concentration required to prolong the coagulation time by a factor of two (μ M) | Preparation process (Ex. No.) | m.p. (° C) | Elementary analysis Upper: Calculated (%) Lower: Found (%) C | H | N | I.R. (KBr) ($cm^{-1}$) |
|---|---|---|---|---|---|---|---|---|---|---|
| 233 | 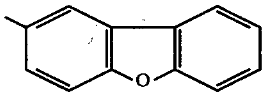 | 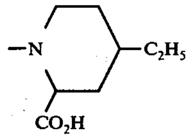 | — | | 3 | " | 57.43<br>57.26 | 6.13<br>6.04 | 12.88<br>12.71 | 3,350<br>3,130<br>1,615 |
| 234 | 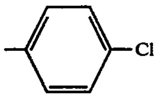 | 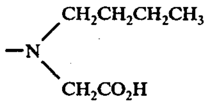 | — | | 5 | " | 46.80<br>46.61 | 6.11<br>6.05 | 15.16<br>15.23 | 3,375<br>3,150<br>1,630 |
| 235 | 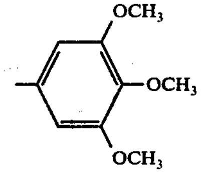 | 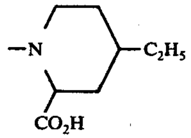 | — | | 3 | " | 50.82<br>50.71 | 6.86<br>6.69 | 12.89<br>12.57 | 3,360<br>3,120<br>1,620 |

The pharmaceutically acceptable salts of the above compounds are of course also included within the scope of this invention.

For the preparation of the compounds of this invention, various methods can be employed depending upon the particular starting materials and/or intermediates involved. Successful preparation of these compounds is possible by way of several synthetic routes which are outlined below.

(a) Condensation of an L-argininamide with an arylsulfonyl halide

This process may be illustrated as follows:

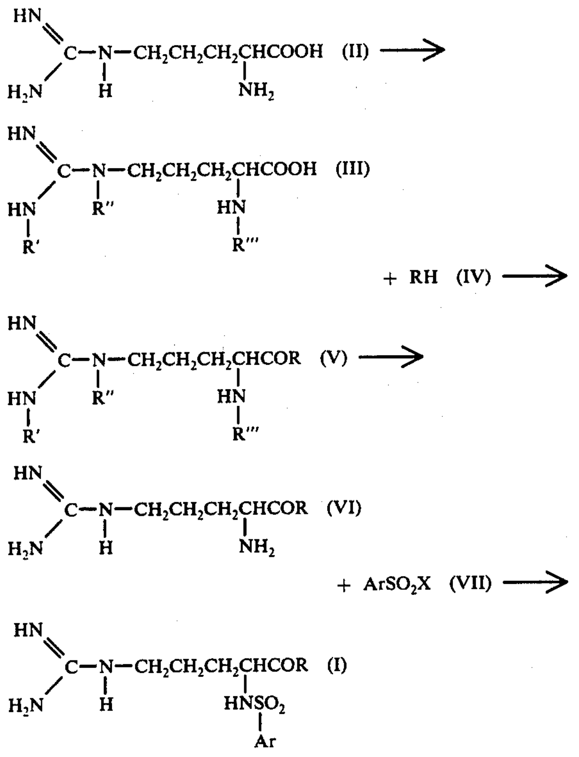

In the above formulas, R and Ar are as defined herein above; X is halogen, R''' is a protective group for the $\alpha$ -amino group, such as benzyloxycarbonyl or tert-butoxycarbonyl; R' and R'' are selected from the group consisting of hydrogen and protective groups for the guanidino group, such as nitro, tosyl, trityl, oxycarbonyl and the like; and at least one of R' and R'' is a protective group for the guanidino group. The $N^2$-arylsulfonyl-L-argininamide (I) is prepared by the condensation of an L-argininamide (VI) with a substantially equimolar amount of an arylsulfonyl halide (VII), preferably a chloride.

The condensation reaction is generally effected in a suitable reaction-inert solvent in the presence of an excess of a base, such as an organic base (triethylamine, pyridine) or a solution of an inorganic base (sodium hydroxide, potassium carbonate), at a temperature of 0° C to the boiling temperature of the solvent for a period of 10 minutes to 15 hours.

The preferred solvents for the condensation include benzene-diethyl ether, diethyl ether-water and dioxanewater.

After the reaction is complete, the formed salt is extracted with water, and the solvent is removed by such standard means as evaporation under reduced pressure to give the $N^2$-arylsulfonyl-L-argininamide (I), which can be purified by trituration or recrystallization from a suitable solvent, such as diethyl ethertetrahydrofuran, deithyl ether-methanol and watermethanol, or may be chromatographed on silica gel. The L-argininamides (VI) starting materials required for the condensation reaction can be prepared by protecting the guanidino and $\alpha$ -amino groups of L-arginine (II) via nitration, acetylation, formylation, phthaloylation, trifluoroacetylation, p-methoxybenzyloxycarbonylation, benzoylation, benzyloxycarbonylation, tert-butoxycarbonylation or tritylation and then condensing the formed $N^G$-substituted-$N^2$-substituted-L-arginine (III) with a corresponding amino acid derivative (IV) by such a conventional process as the acid chloride method, azide method, mixed anhydride method, activated ester method or carbodiimide method, and thereafter selectively removing the protective groups from the formed $N^G$-substituted-$N^2$-substituted-L-argininamide (V). The amino acid derivatives (IV) which are the starting materials for the preparation of the $N^G$-substituted-$N^2$-substituted-L-argininamides (V) are represented by the following formulas:

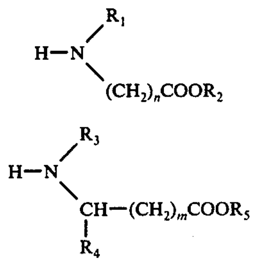

(VIII)

(IX)

In the above formulas, $R_1$, $R_2$, $R_3$, $R_4$, $R_5$, $n$ and $m$ are as defined herein above.

The amino acid derivatives of the above formula (VIII) or (IX) can be prepared by the condensation of a haloacetate, 3-halopropionate or 4-halobutyrate with an appropriate amine having the formula $R_1NH_2$ or $R_3NH_2$. (See, J. Org. Chem. 25 728-732 (1969)).

The condensation reaction is generally carried out without a solvent or in a solvent, such as benzene or ether, in the presence of an organic base, such as triethylamine or pyridine, at a temperature of 0° C to 80° C for a period of 10 minutes to 20 hours. After the reaction is complete, the formed amino acid derivative is separated by such conventional means as extraction with a suitable solvent or evaporation of the reaction solvent and thereafter purified by distillation under reduced pressure.

Among the amino acid derivatives, amino acid tert-butyl ester derivatives are preferred, because they are easily converted to other ester derivatives by acidolysis in the presence of a corresponding alcohol employing an inorganic acid (HCl, $H_2SO_4$, etc.) or an organic acid (toluenesulfonic acid, trifluoroacetic acid, etc.). The arylsulfonyl halides (VII) which are the starting materials for the preparation of the $N^2$-arylsulfonyl-L-argininamides (I) can be prepared by halogenating the requisite arylsulfonic acids or their salts, e.g., sodium salts, by conventional methods well known to those skilled in the art.

In practice, halogenation is carried out without a solvent or in a suitable solvent e.g., halogenated hydrocarbons or DMF in the presence of a halogenating agent, e.g., phosphorous oxychloride, thionyl chloride, phosphorous trichloride, phosphorous tribromide or phosphorous pentachloride, at a temperature of −10° C to 200° C for a period of 5 minutes to 5 hours. After the reaction is complete, the reaction product is poured into ice water and then extracted with a solvent such as ether, benzene, ethyl acetate, chloroform or the like.

The arylsulfonyl halide can be purified by recrystallization from a suitable solvent such as hexane, benzene or the like.

(b) Removal of the $N^G$-substituent from an $N^G$-substituted-$N^2$-arylsulfonyl-L-argininamide This process may be illustrated as follows:

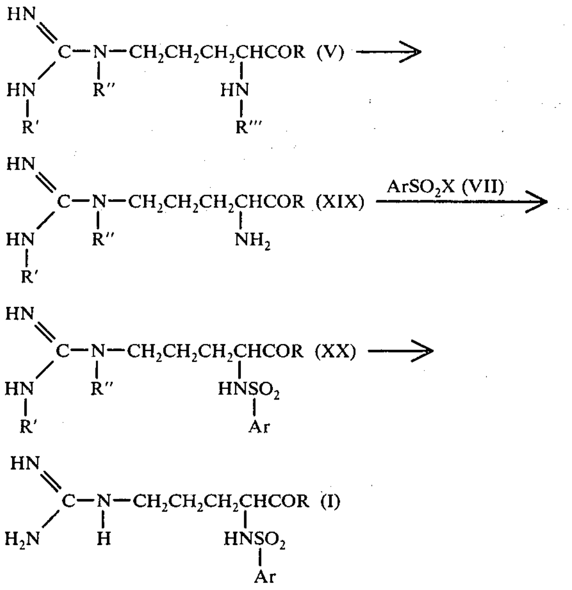

(V) (XIX) (XX) (I)

In the above formulas, R, Ar, X, R', R'' and R''' are as defined herein above.

The $N^2$-arylsulfonyl-L-argininamide (I) is prepared by removing the $N^G$-substituent from an $N^G$-substituted-$N^2$-arylsulfonyl-L-argininamide (XX) by means of acidolysis or hydrogenolysis.

The acidolysis is generally effected by contacting the $N^G$-substituted-$N^2$-arylsulfonyl-L-argininamide (XX) and an excess of an acid such as hydrogen fluoride, hydrogen chloride, hydrogen bromide or trifluoroacetic acid, without a solvent or in a solvent, such as an ether (tetrahydrofuran, dioxane), an alcohol (methanol, ethanol) or acetic acid at a temperature of −10° C to 100° C, and preferably at room temperature for a period of 30 minutes to 24 hours.

The products are isolated by evaporation of the solvent and the excess acid, or by trituration with a suitable solvent followed by filtration and drying.

Because of the use of the excess acid, the products are generally the acid addition salts of the $N^2$-arylsulfonyl-L-argininamides (I), which can be easily converted to a free amide by neutralization.

The removal of the nitro group and the oxycarbonyl group, e.g., benzyloxycarbonyl, p-nitrobenzyloxycarbonyl, is readily accomplished by the hydrogenolysis.

At the same time, the benzyl ester moiety which can be included in the R group is converted to the carboxyl group by the hydrogenolysis.

The hydrogenolysis is effected in a reaction-inert solvent, e.g., methanol, ethanol, tetrahydrofuran or dioxane, in the presence of a hydrogen-activating catalyst, e.g., Raney nickel, palladium, or platinum, in a hydrogen atmosphere at a temperature of 0° C to the boiling temperature of the solvent for a period of 2 hours to 120 hours.

The hydrogen pressure is not critical, and atmospheric pressure is sufficient.

The $N^2$-arylsulfonyl-L-argininamides (I) are isolated by filtration of the catalyst followed by evaporation of the solvent.

The $N^2$-arylsulfonyl-L-argininamides can be purified in the same manner as described above.

The $N^G$-substituted-$N^2$-arylsulfonyl-L-argininamides (XX) starting materials can be prepared by condensing an $N^G$-substituted-$N^2$-substituted L-arginine (III) (generally the $N^G$-substituent is nitro or acyl, and the $N^2$-substituent is a protective group for the amino group, such as benzyloxycarbonyl, tert-butoxycarbonyl, or the like) and a corresponding amino acid derivative (IV), selectively removing only the $N^2$-substituent of an $N^G$-substituted-$N^2$-substituted L-argininamide (V) by means of catalytic hydrogenolysis or acidolysis, and then condensing the thus obtained $N^G$-substituted-L-argininamide (XIX) with an arylsulfonyl halide (VII), preferably a chloride in the presence of a base in a solvent. These reaction conditions are as described above in the condensation of an L-argininamide with an arylsulfonyl halide, and the removal of the $N^G$-substituent from an $N^G$-substituted-$N^2$-arylsulfonyl-L-argininamide.

(c) Condensation of an $N^2$-arylsulfonyl-L-arginyl halide with an amino acid derivative This process may be illustrated as follows:

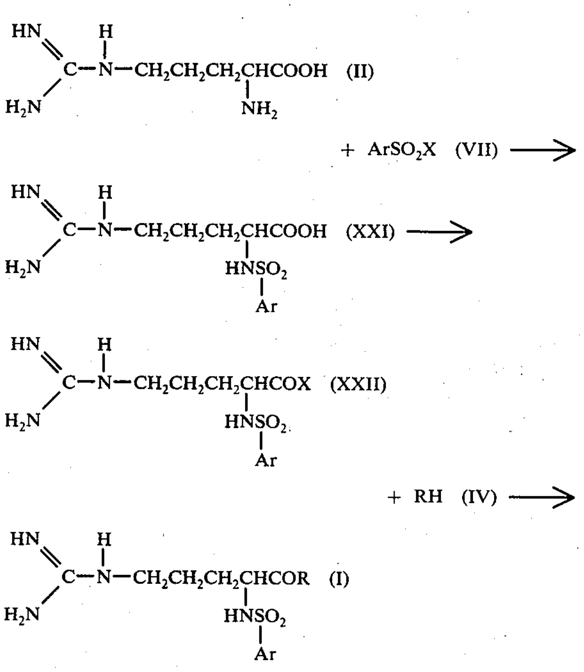

(II) (XXI) (XXII) (I)

In the above formulas, R, Ar and X are as defined herein above.

The $N^2$-arylsulfonyl-L-argininamide (I) is prepared by the condensation of an $N^2$-arylsulfonyl-L-arginyl halide (XXII), preferably a chloride with at least an equimolar amount of an amino acid derivative (IV). The condensation reaction can be carried out without an added solvent in the presence of a base. However, satisfactory results will be obtained with the use of a solvent such as basic solvents (dimethylformamide, dimethylacetamide, etc.) or halogenated solvents (chloroform, dichloromethane, etc.).

The amount of the solvent to be used is not critical and may vary from about 5 to 100 times the weight of the $N^2$-arylsulfonyl-L-arginyl halide (XXII).

Preferred condensation reaction temperatures are in the range of from $-10°$ C to room temperature. The reaction time is not critical, but varies with the amino acid derivative (IV) employed. In general, a period of from 5 minutes to 10 hours is operable. The obtained $N^2$-arylsulfonyl-L-argininamide can be isolated and purified in the same manner as described above.

The $N^2$-arylsulfonyl-L-arginyl halide (XXII) starting materials required for the condensation reaction can be prepared by reacting an $N^2$-arylsulfonyl-L-arginine (XXI) with at least an equimolar amount of a halogenating agent such as thionyl chloride, phosphorous oxychloride, phosphorus trichloride, phosphorous pentachloride or phosphorus tribromide. The halogenation can be carried out with or without an added solvent. The preferred solvents are chlorinated hydrocarbons such as chloroform and dichloromethane, and ethers such as tetrahydrofuran and dioxane.

The amount of the solvent to be used is not critical and may vary from about 5 to 100 times the weight of the $N^2$-arylsulfonyl-L-arginine (XXI).

Preferred reaction temperature are in the range of $-10°$ C to room temperature. The reaction time is not critical, but varies with the halogenating agent and reaction temperature. In general, a period of 15 minutes to 5 hours is operable.

The $N^2$-arylsulfonyl-L-arginines (XXI) which are the starting materials for the preparation of the $N^2$-arylsulfonyl-L-arginyl halides (XXII) can be prepared by the condensation of L-arginine (II) with a substantially equimolar amount of arylsulfonyl halides (VII), by a method similar to that described in the condensation of an L-argininamide with an arylsulfonyl halide.

(d) Guanidylation of an $N^2$-arylsulfonyl-L-ornithinamide or an acid addition salt thereof This process may be illustrated as follows:

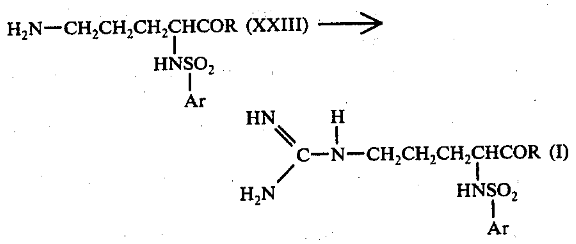

(XXIII)

(I)

In the above formulas, R and Ar are as defined herein above.

The $N^2$-arylsulfonyl-L-argininamide (I) is prepared by guanidylating an $N^2$-arylsulfonyl-L-ornithinamide (XXIII) with an ordinary guanidylating agent such as an O-alkylisourea, S-alkylisothiourea, 1-guanyl-3,5-dimethylphrazole or carbodiimide. The preferred guanidylating agents are the O-alkylisourea and the S-alkylisothiourea.

The guanidylation of the $N^2$-arylsulfonyl-L-ornithinamide (XXIII) with the O-alkylisourea or S-alkylisothiourea is generally effected in a solvent in the presence of a base at a temperature of from 0° C to the boiling temperature of the solvent for a period of from 30 minutes to 50 hours. Examples of the preferred bases are triethylamine, pyridine, sodium hydroxide and sodium methoxide. The base is used in an amount of 0.01 to 0.1 equivalent to the $N^2$-arylsulfonyl-L-ornithinamide.

Example of the preferred solvents are water, water-ethanol and water-dioxane.

After the reaction is complete, the $N^2$-arylsulfonyl-L-argininamide (I) is isolated by evaporation of the solvent followed by removal of the excess base and the formed salt by a water wash.

It is well recognized in the art that an ester derivative of the $N^2$-arylsulfonyl-L-argininamide (I) wherein $R_2$ or $R_5$, is alkyl, aralkyl, aryl or 5-indanyl, can be prepared from a carboxylic acid derivative of the $N^2$-arylsulfonyl-L-argininamide wherein $R_2$ or $R_5$ is hydrogen, by the conventional esterification methods well known to those skilled in the art. It is also well recognized in the art that the carboxylic acid derivative can be prepared from the ester derivative by the conventional hydrolysis or acidolysis methods. The conditions under which esterification, hydrolysis or acidolysis would be carried out will be each apparent to those skilled in the art.

The $N^2$-arylsulfonyl-L-argininamide (I) of this invention forms acid addition salts with any of a variety of inorganic and organic acids. Some of the $N^2$-arylsulfonyl-L-argininamides containing a free carboxyl group, wherein $R_2$ and $R_5$ is hydrogen, forms salts with any of a variety of inorganic and organic bases.

The product of the reactions described above can be isolated in the free form or in the form of salts. In addition, the product can be obtained as pharmaceutically acceptable acid addition salts by reacting one of the free bases with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like. In a similar manner, the product can be obtained as pharmaceutically acceptable salts by reacting one of the free carboxylic acids with a base, such as sodium hydroxide, potassium hydroxide, ammonium hydroxide, triethylamine, procaine, dibenzylamine, 1-ephenamine, N,N'-dibenzylethylenediamine, N-ethylpiperidine or the like.

Likewise, treatment of the salts with a base or acid results in a regeneration of the free amide.

As stated above, the $N^2$-arylsulfonyl-L-argininamides, and the salts thereof of this invention are characterized by their highly specific inhibitory activity in mammals against thrombin as well as by their substantial lack of toxicity, and therefore these compounds are useful in the determination of thrombin in blood as diagnostic reagents, and/or for the medical control or prevention of thrombosis.

The compounds of this invention are also useful as an inhibitor of platelet aggregation.

The antithrombotic activity of the $N^2$-arylsulfonyl-L-argininamide of this invention was compared with that of a known antithrombotic agent, $N^2$-(p-tolylsulfonyl)-L-arginine methyl ester, by determining the fibrinogen coagulation time. The measurement of the fibrinogen coagulation time was conducted as follows:

An 0.8 ml aliquot of a fibrinogen solution, which had been prepared by dissolving 150 mg of bovine fibrinogen (Cohn fraction I) supplied by Armour Inc. in 40 ml of a borate saline buffer (pH 7.4), was mixed with 0.1 ml of a borate saline buffer, pH 7.4, (control) or a sample solution in the same buffer, and 0.1 ml of a thrombin solution (5 units/ml) supplied by Mochida Pharmaceutical Co., Ltd. was added to the solutions in an ice bath.

Immediately after mixing, the reaction mixture was transferred from the ice bath to a bath maintained at 25° C. Coagulation times were taken as the period between the time of transference to the 25° C bath and the time of the first appearance of fibrin threads. In the cases where no drug samples were added, the coagulation time was 50–55 seconds. The experimental results are summarized in Table 1. The term "concentration required to prolong the coagulation time by a factor of two" is the concentration of an active ingredient required to prolong the normal coagulation time 50–55 seconds to 100–110 seconds.

The concentration required to prolong the coagulation time by a factor of two for the known antithrombotic agent, $N^2$-(p-tolylsulfonyl)-L-arginine methyl ester, was 1,100μm. The inhibitors are shown in Table 1 by indicating R and Ar in the formula (I) and the addition moiety.

When a solution containing an $N^2$-arylsulfonyl-L-argininamide of this invention was administered intravenously into animal bodies, the high antithrombotic activity in the circulating blood was maintained for from 1 to 3 hours. The halflife for decay of the antithrombotic compounds of this invention in circulating blood was shown to be approximately 60 minutes; the physiological conditions of the host animals (rat, rabbit, dog and chimpanzee) were well maintained. The experimental decrease of fibrinogen in animals caused by infusion of thrombin was satisfactorily controlled by simultaneous infusion of the compounds of this invention.

The acute toxicity values ($LD_{50}$) determined by intraperitoneal administration of substances of formula (I) in mice (male, 20 g) range from about 1,000 to 10,000 milligrams per kilogram of body weight.

Representative $LD_{50}$ values for the compounds of this invention are shown in the following Table.

| Compound | $LD_{50}$ (mg/kg) |
|---|---|
| $N^2$-(7-methyl-2-naphthylsulfonyl)-L-arginyl-N-butylglycine | > 1,500 |
| $N^2$-(6,7-dimethoxy-2-naphthylsulfonyl)-L-arginyl-N-(2-methoxyethyl)glycine | 1,900–2,400 |
| $N^2$-(6,7-dimethoxy-2-naphthylsulfonyl)-L-arginyl-N-(2-ethoxyethyl)-β-alanine | 660–1,000 |
| $N^2$-(4,6-dimethoxy-2-naphthylsulfonyl)-L-arginyl-N-(2-methoxyethyl)glycine | 660–1,000 |
| $N^2$-(7-methoxy-2-naphthylsulfonyl)-L-arginyl-N-(2-methoxyethyl)glycine | 2,000 |
| $N^2$-(5,6,7,8-tetrahydro-1-naphthylsulfonyl)-L-arginyl-N-(2-methoxyethyl)glycine | > 1,500 |
| $N^2$-(6,7-dimethyl-1-naphthylsulfonyl)-L-arginyl-N-(2-methoxyethyl)glycine | > 1,500 |
| $N^2$-(6,7-dimethoxy-2-naphthylsulfonyl)-L-arginyl-N-(2-ethylthioethyl)glycine | > 1,000 |
| $N^2$-(6,7-dimethoxy-2-naphthylsulfonyl)-L-arginyl-N-benzylglycine | > 1,000 |
| $N^2$-(4,6-dimethoxy-2-naphthylsulfonyl)-L-arginyl-N-benzylglycine | > 1,000 |
| $N^2$-(5-methoxy-1-naphthylsulfonyl)-L-arginyl-N-benzylglycine | > 1,000 |
| $N^2$-(6,7-dimethoxy-2-naphthylsulfonyl)-L-arginyl-N-phenethylglycine | > 1,500 |
| $N^2$-(6,7-dimethoxy-2-naphthylsulfonyl)-L-arginyl-N-cyclohexylglycine | > 1,500 |
| $N^2$-(6,7-dimethoxy-2-naphthylsulfonyl)-L-arginyl-N-cyclohexylmethylglycine | > 1,500 |
| $N^2$-(7-methyl-2-naphthylsulfonyl)-L-arginyl-N-tetrahydrofurfurylglycine | 600 |
| $N^2$-(6,7-dimethoxy-2-naphthylsulfonyl)-L-arginyl-N-tetrahydrofurfurylglycine | 620 |
| $N^2$-(6,7-dimethoxy-2-naphthylsulfonyl)-L-arginyl-N-butylalanine | > 1,500 |
| $N^2$-(4,6-dimethoxy-2-naphthylsulfonyl)-L-arginyl-N-cyclohexylmethylalanine | > 1,500 |
| 1-[$N^2$-(6,7-dimethoxy-2-naphthylsulfonyl)-L-arginyl]-2-piperidinecarboxylic acid | 1,500 |
| Ethyl [1-$N^2$-(7-methoxy-2-naphthylsulfonyl)-L-arginyl]-4-methyl-2-piperidinecarboxylate | 670–1,000 |
| 1-[$N^2$-(4,6-dimethoxy-2-napthylsulfonyl)-L-arginyl]-4-methyl-2-piperidinecarboxylic acid | 670–1,000 |
| 1-[$N^2$-(1-naphthylsulfonyl)-L-arginyl]-4-methyl-2-piperidinecarboxylic acid | 700–1,000 |
| 1-[$N^2$-(5-dimethylamino-1-naphtylsulfonyl)-L-arginyl]-2-piperidinecarboxylic acid | 700–1,000 |
| 4-[$N^2$-(7-methoxy-2-naphthylsulfonyl)-L-arginyl]-3-morpholinecarboxylic acid | > 1,000 |
| 2-[$N^2$-(6,7-dimethoxy-2-naphthylsulfonyl)-1-arginyl]1,2,3,4-tetrahydroisoquinoline-3-carboxylic acid | > 1,000 |
| 2-[$N^2$-(6,7-dimethoxy-2-naphthylsulfonyl)-1-arginyl]-1-isoindolinecarboxylic acid | > 1,000 |

On the other hand, $LD_{50}$ values for $N^2$-dansyl-N-butyl-L-argininamide and $N^2$-dansyl-N-methyl-N-butyl-L-argininamide are 75 and 70 milligrams per kilogram, respectively.

The therapeutic agents in this invention may be administered to mammals, including humans, alone or in combination with pharmaceutically acceptable carriers, the proportion of which is determined by the solubility and chemical nature of the compound, chosen route of administration and standard pharmaceutical practice. For example, the compounds may be injected parenterally, that is, intramuscularly, intravenously or subcutaneously. For parenteral administration, the compounds may be used in the form of sterile solutions containing other solutes, for example, sufficient saline or glucose to make the solution isotonic. The compounds may be administered orally in the form of tablets, capsules, or granules containing suitable excipients such as starch, lactose, white sugar and the like. The compounds may be administered sublingually in the form of troches or lozenges in which each active ingredient is mixed with sugar or corn syrups, flavoring agents and dyes, and then dehydrated sufficiently to make the mixture suitable for pressing into solid form. The compounds may be administered orally in the form of solutions which may contain coloring and flavoring agents. Physicians will determine the dosage of the present therapeutic agents which will be most suitable for humans, and dosages vary with the mode of administration and the particular compound chosen. In addition, the dosage will vary with the particular patient under treatment.

When the composition is administered orally, a larger quantity of the active agent will be required to produce the same effect as caused with a smaller quantity given parenterally.

The therapeutic dosage is generally 10–50 mg/kg of active ingredient parenterally, 10–500 mg/kg orally per day. Having generally described the invention, a more complete understanding can be obtained by reference to certain specific examples, which are included for purposes of illustration only and are not intended to be limiting unless otherwise specified.

It is to be understood that the present invention includes pharmaceutical compositions containing a compound of the invention as an active ingredient. Such compositions may be in the forms described above. In particular, the invention includes such compositions in unit dose form.

EXAMPLE 1

(A) $N^2$-(2-dibenzothienylsulfonyl)-L-arginine:

To a well stirred solution of 83.6 g of L-arginine in 800 ml of 10% potassium carbonate solution was added 112.7 g of 2-dibenzothiophenesulfonyl chloride in 800 ml of benzene. The reaction mixture was stirred at 60° C for 5 hours, during which time the product precipitated. After one hour at room temperature, the precipitate was filtered and washed successively with benzene and water to give 127 g (76 percent) of $N^2$-(2-dibenzothienylsulfonyl)-L-arginine.

(B) $N^2$-(2-dibenzothienylsulfonyl)-L-arginyl chloride:

A suspension of 4.21 g of $N^2$-(2-dibenzothienylsulfonyl)-L-arginine in 20 ml of thionyl chloride was stirred for 2 hours at room temperature. Addition of cold dry diethyl ether resulted in a precipitate which was collected by filtration and washed several times with dry diethyl ether to give $N^2$-(2-dibenzothienylsulfonyl)-L-arginyl chloride.

(C) $N^2$-(2-dibenzothienylsulfonyl)-L-arginyl-N-butylglycine tert-butyl ester:

To a stirred solution of 2.67 g of N-butylglycine tert-butyl ester in 20 ml of chloroform was carefully added $N^2$-(2-dibenzothienylsulfonyl)-L-arginyl chloride obtained above. The reaction mixture was allowed to stand at room temperature for one hour.

At the end of this period, the reaction mixture was washed twice with 20 ml of saturated sodium chloride solution and evaporated to dryness.

The residue was triturated with a small amount of diethyl ether to give an amorphous solid. This was collected by filtration and reprecipitated from ethanol-ethyl ether to give 3.1 g (49 percent) of $N^2$-(2-dibenzothienylsulfonyl)-L-arginyl-N-butylglycine tert-butyl ester.

I.R. (KBr): 3350, 1740, 1625 $cm^{-1}$

Analysis - Calcd. for $C_{28}H_{39}O_5N_5S_2.\frac{1}{2}H_2SO_3$ (percent): C, 53.31; H, 6.39; N, 11.10 Found (percent): C, 53.21; H, 6.46; N, 10.89

(D) $N^2$-(2-dibenzothienylsulfonyl)-L-arginyl-N-butylglycine: To a solution of 2.00 g of $N^2$-(2-dibenzothienylsulfonyl)-L-arginyl-N-butylglycine tert-butyl ester in 20 ml of chloroform was added 50 ml of 15% HCl-ethyl acetate. The reaction mixture was stirred for 5 hours at room temperature. At the end of this period, the reaction mixture was evaporated to dryness. The residue was washed several times with dry diethyl ether and chromatographed on 80 ml of Daiaion ® SK 102 ion exchange resin (200–300 mesh, $H^{30}$ form, manufactured by Mitsubishi Chemical Industries Limited) packed in water, washed with water and eluted with 3% ammonium hydroxide solution.

The fraction eluted from 3% ammonium hydroxide solution was evaporated to dryness to give 0.9 g (53 percent) of $N^2$-(2-dibenzothienylsulfonyl)-L-arginyl-N-butylglycine as an amorphous solid, I.R. (KBr): 3350, 1640, 1270 $cm^{-1}$ Analysis-Calcd. for $C_{24}H_{31}N_5O_5S_2$ (percent): C, 54.01; H, 5.86; N, 13.12 Found (percent): C, 53.78; H, 5.97; N, 12.96

EXAMPLE 2

(A) $N^2$-(2-dibenzothienylsulfonyl)-L-arginyl-N-(2-methoxyethyl)glycine ethyl ester To a stirred solution of 2.42 g of N-(2-methoxyethyl) glycine ethyl ester and 4.0 ml of triethylamine in 50 ml of chloroform, which was cooled in an ice-salt bath, was added in portions $N^2$-(2-dibenzothienylsulfonyl)-L-arginyl chloride obtained above. The reaction mixture was stirred overnight at room temperature. At the end of this period, 50 ml of chloroform was added and the chloroform solution was washed twice with 25 ml of saturated sodium chloride solution, dried over anhydrous sodium sulfate and evaporated in vacuo. The oily residue was washed with ethyl ether to give 5.5 g of powdery $N^2$-(2-dibenzothienylsulfonyl)-L-arginyl-N-(2-methoxyethyl)glycine ethyl ester Analysis calcd for $C_{25}H_{23}O_6N_5S_2.\frac{1}{2}$ $H_2SO_3$ (percent): C, 50.49; H, 4.07; N, 11.78 Found (percent): C, 50.22; H, 4.18; N, 11.51

(B) $N^2$-(2-dibenzothienylsulfonyl)-L-arginyl-N-(2-methoxyethyl)glycine:

A solution of 5.5 g of $N^2$-(2-dibenzothienylsulfonyl)-L-arginyl-N-(2-methoxyethyl)glycine ethyl ester in 15 ml of methanol and 15 ml of 2N-NaOH solution was warmed to 40° C and held at that temperature for 10 hours. At the end of this period, the reaction mixture was concentrated and chromatographed on 200 ml of Daiaion ® SK 102 ion exchange resin (200–300 mesh, $H^{30}$ form, manufactured by Mitsubishi Chemical Industries Limited) packed in water, washed with ethanol-water (1 : 4) and eluted with ethanol-water-$NH_4OH$ (10 : 9 : 1). The main fraction was evaporated to dryness and washed with ethyl ether to give 3.05 g (62 percent) of $N^2$-(2-dibenzothienylsulfonyl)-L-arginyl-N-(2-methoxyethyl)glycine as an amorphous solid. I.R. (KBr): 3,400, 1,630, 1,280 $cm^{-1}$ Analysis-Calcd for $C_{23}H_{29}O_6N_5S_2$ (percent): C, 51.57; H, 5.46; N, 13.08 Found (percent): C, 51.35; H, 5.63; N, 12.86

EXAMPLE 3

(A) $N^G$-nitro-$N^2$-(tert-butoxycarbonyl)-L-arginyl-N-butylglycine benzyl ester To a stirred solution of 28.4 g of $N^G$-nitro-$N^2$-(tert-butoxycarbonyl)-L-arginine in 450 ml of dry tetrahydrofuran were added in turn 12.4 ml of triethylamine and 12.4 ml of isobutyl chloroformate while keeping the temperature at −5° C. After 15 minutes, to this were added 35.0 g of N-butylglycine benzyl ester p-toluenesulfonate, 12.4 ml of triethylamine and dry tetrahydrofuran, and then the mixture was stirred for 15 minutes at −5° C. At the end of this period, the reaction mixture was warmed to room temperature. The solvent was evaporated and the residue taken in 400 ml of ethyl acetate, and washed successively with 200 ml of water, 100 ml of 5% sodium bicarbonate solution, 100 ml of 10% citric acid solution and 200 ml of water. The ethyl acetate solution was dried over anhydrous sodium sulfate. Upon evaporation of the solvent, the residue was dissolved in 20 ml of chloroform, and the solution was applied to a column (80 cm × 6 cm) of 500 g of silica gel packed in chloroform.

The product was eluted first with chloroform, and then 3% methanol-chloroform. The fraction eluted from 3% methanol-chloroform was evaporated to dryness to give 26.0 g (56 percent) of $N^G$-nitro-$N^2$-(tert-butoxycarbonyl)-L-arginyl-N-butylglycine benzyl ester in the form of a syrup. I.R. (KBr): 3,300, 1,740, 1,690 $cm^{-1}$ (B) $N^G$-nitro-L-arginyl-N-butylglycine benzyl ester hydrochloride:

To a stirred solution of 26.0 g of $N^G$-nitro-$N^2$-(tert-butoxycarbonyl)-L-arginyl-N-butylglycine benzyl ester in 50 ml of ethyl acetate was added 80 ml of 10% dry HCl-ethyl acetate at 0° C. After 3 hours, to this solution was added 200 ml of dry ethyl ether to precipitate a viscous oily product. This was filtered and washed with dry ethyl ether to give 20.8 g of $N^G$-nitro-L-arginyl-N-butylglycine benzyl ester hydrochloride as an amorphous solid.

(C) $N^G$-nitro-$N^2$-(3-cyclohexyl-4-methoxyphenylsulfonyl)-L-arginyl-N-butylglycine benzyl ester:

To a stirred solution of 2.33 g of $N^G$-nitro-L-arginyl-N-butylglycine benzyl ester hydrochloride in 10 ml of water and 40 ml of dioxane were added in turn 1.26 g of sodium bicarbonate, and 2.2 g of 3-cyclohexyl-4-methoxyphenylsulfonyl chloride at 5° C, and stirring was continued for 3 hours at room temperature. At the end of this period, the solvent was evaporated and the residue dissolved in 100 ml of ethyl acetate, and washed successively with 10 ml of 1N hydrochloric acid solution, 20 ml of water, 20 ml of 5% sodium bicarbonate and 10 ml of water.

The ethyl acetate solution was dried over anhydrous sodium sulfate. Upon evaporation of the solvent, the residue was chromatographed on 50 g of silica gel packed in chloroform, washed with chloroform and eluted with 3% methanol-chloroform. The fraction eluted from 3% methanol-chloroform was evaporated to give 2.6 g (77 percent) of $N^G$-nitro-$N^2$-(3-cyclohexyl-4-methoxyphenylsulfonyl)-L-arginyl-N-butylglycine benzyl ester in the form of an amorphous solid. I.R. (KBr): 3,300, 2,920, 1,740, 1,640, 1,250 $cm^{-1}$ Analysis - Calcd. for $C_{32}H_{46}O_8N_6S$ (percent): C, 56.95; H, 6.87; N, 12.46 Found (percent): C, 56.49; H, 6.63; N, 12.38

(D) $N^2$-(3-cyclohexyl-4-methoxyphenylsulfonyl)-L-arginyl-N-butylglycine

To a solution of 3.00 g of $N^G$-nitro-$N^2$-(3-cyclohexyl-4-methoxyphenylsulfonyl)-L-arginyl-N-butylglycine benzyl ester in 50 ml of ethanol, 10 ml of acetic acid and 10 ml of water was added 0.5 g of palladium-black and then the mixture was shaken in a hydrogen atmosphere for 50 hours at room temperature. At the end of this period, the ethanol solution was filtered to remove the catalyst and evaporated to dryness. The residue was washed several times with dry ethyl ether and chromatographed on 80 ml of Daiaion® SK 102 ion exchange resin (200–300 mesh, $H^+$ form, manufactured by Mitsubishi Chemical Industries Limited) packed in water, washed with water, and eluted with 3% ammonium hydroxide solution. The fraction eluted from 3% ammonium hydroxide solution was evaporated to dryness to give 1.5 g (72%) of $N^2$-(3-cyclohexyl-4-methoxyphenylsulfonyl)-L-arginyl-N-butylglycine as an amorphous solid. I.R. (KBr): 3,350, 2,920, 1,630, 1,250 $cm^{-1}$ Analysis - Calcd. for $C_{25}H_{41}N_6O_5S_1$ (percent): C, 55.63; H, 7.66; N, 12.98 Found (percent): C, 55.32; H, 7.39; N, 12.84

EXAMPLE 4

(A) $N^2$-(6,7-dimethoxy-2-naphthylsulfonyl)-L-arginyl-N-(2-methoxyethyl)glycyl chloride hydrochloride:

A suspension of 2.00 g of $N^2$-(6,7-dimethoxy-2-naphthylsulfonyl)-L-arginyl-N-(2-methoxyethyl)glycine in 20 ml of thionyl chloride was stirred for 2 hours at room temperature. Addition of cold dry ethyl ether resulted in a precipitate which was collected by filtration and washed several times with dry ethyl ether to give $N^2$-(6,7-dimethoxy-2-naphthylsulfonyl)-L-arginyl-N-(2-methoxyethyl)glycyl chloride hydrochloride.

(B) $N^2$-(6,7-dimethoxy-2-naphthylsulfonyl)-L-arginyl-N-(2-methoxyethyl)glycine m-tolyl ester hydrochloride:

A mixture of 2.00 g of m-cresol and $N^2$-(6,7-dimethoxy-2-naphthylsulfonyl)-L-arginyl-N-(2-methoxyethyl)glycyl chloride hydrochloride obtained above was heated at 90° C for 50 minutes. At the end of this period, the reaction mixture was cooled, washed several times with dry ethyl ether, and then dissolved in 10 ml of dry ethyl alcohol. Addition of cold dry ethyl ether resulted in a precipitate which was washed several times with dry ethyl ether to give 2.12 g (86 percent) of $N^2$-(6,7-dimethoxy-2-naphthylsulfonyl)-L-arginyl-N-(2-methoxyethyl)glycine m-tolyl ester hydrochloride in the form of a powder. I.R. (KBr): 3,250, 3,100, 1,740, 1,640 $cm^{-1}$. Various other $N^2$-arylsulfonyl-L-argininamides or acid addition salts thereof were synthesized in accordance with the procedures of the above examples, and the test results are summarized in Table 2.

TABLE 2

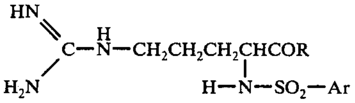

| Sample No. | Ar | R | Addition moiety | Concentration required to prolong the coagulation time by a factor of two (μM) | Preparation process (Ex. No.) | Physical properties | Elemental analysis Upper: Calculated Lower: Found C | H | N | I.R. (KBr) ($cm^{-1}$) |
|---|---|---|---|---|---|---|---|---|---|---|
| 1 | 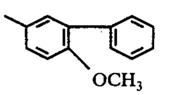 | 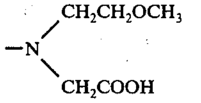 | | 20 | 3 | | 53.82<br>53.59 | 6.21<br>6.11 | 13.08<br>12.78 | 3,350, 1,630<br>1,270, 1,160 |
| 2 | 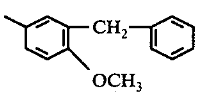 | 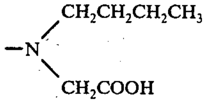 | | 38 | 3 | | 57.02<br>56.69 | 6.81<br>6.65 | 12.79<br>12.84 | 3,400, 1,630<br>1,260 |
| 3 | 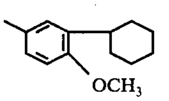 | 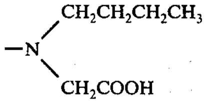 | | 5 | 3 | | 55.63<br>55.32 | 7.66<br>7.39 | 12.98<br>12.84 | 3,350, 2,920<br>1,630, 1,250 |
| 4 | 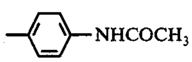 | 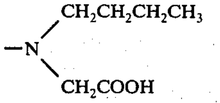 | | | 3 | | 49.57<br>49.24 | 6.66<br>6.79 | 17.34<br>17.48 | 3,400, 1,640<br>1,530, 1,160 |

TABLE 2-continued

| Sample No. | 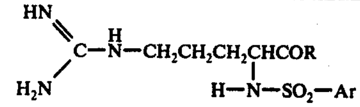<br>Ar | R | Addition moiety | Concentration required to prolong the coagulation time by a factor of two (μM) | Preparation process (Ex. No.) | Physical properties | Elemental analysis Upper: Calculated Lower: Found C | H | N | I.R. (KBr) ($cm^{-1}$) |
|---|---|---|---|---|---|---|---|---|---|---|
| 5 | 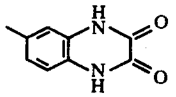 | 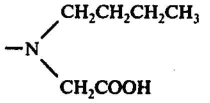 | | | 3 | | 46.95<br>46.67 | 5.71<br>5.79 | 19.17<br>18.87 | 3,400,<br>1,680<br>1,630,<br>1,380 |
| 6 | 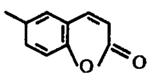 | 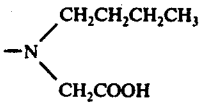 | | | 2 | | 50.89<br>50.79 | 5.96<br>5.98 | 14.13<br>13.86 | 3,400,<br>1,740<br>1,630 |
| 7 | 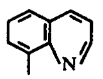 | 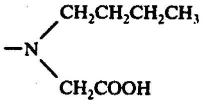 | | 19 | 3 | | 52.70<br>52.66 | 6.32<br>6.19 | 17.56<br>17.82 | |
| 8 | 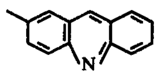 | 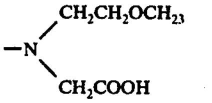 | | | 2 | | 54.32<br>54.08 | 5.70<br>5.96 | 15.84<br>15.73 | 3,400<br>1,635<br>1,510 |
| 9 | 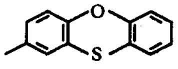 | 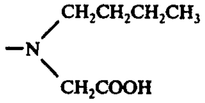 | | | 2 | | 52.44<br>52.43 | 5.69<br>5.86 | 12.74<br>12.58 | 3,400<br>1,630<br>1,290 |
| 10 | 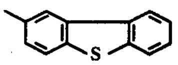 | 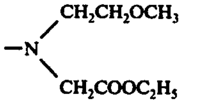 | ½$H_2SO_3$ | | 2 | | 50.49<br>50.22 | 4.07<br>4.18 | 11.78<br>11.51 | 3,350<br>1,735<br>1,620 |
| 11 | 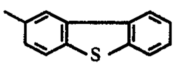 | 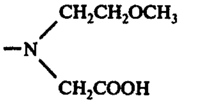 | | | 2 | | 51.57<br>51.35 | 5.46<br>5.63 | 13.08<br>12.86 | 3,400<br>1,630<br>1,280 |
| 12 | 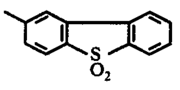 | 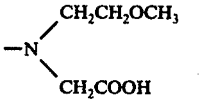 | | | 2 | | | | | |
| 13 | 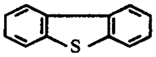 | 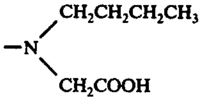 | | | 1 | | 54.01<br>53.78 | 5.86<br>5.97 | 13.12<br>12.96 | 3,350<br>1,640<br>1,270 |
| 14 | 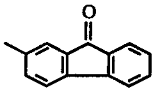 | 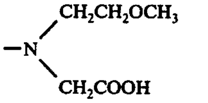 | | | 2 | | 54.22<br>54.08 | 5.50<br>5.36 | 13.18<br>12.95 | 3,400<br>1,700<br>1,635 |

EXAMPLE 5

Tablets suitable for oral administration

Tablets containing the ingredients indicated below may be prepared by conventional techniques.

| Ingredient | Amount per tablet (mg) |
|---|---|
| $N^2$-(3-cyclohexyl-4-methoxy-phenylsulfonyl)-L-arginyl-N-butylglycine | 250 |
| Lactose | 140 |
| Corn starch | 35 |
| Talcum | 20 |
| Magnesium stearate | 5 |
| Total | 450 mg |

EXAMPLE 6

Capsules for oral administration

Capsules of the below were made up by thoroughly mixing together batches of the ingredients and filling hard gelatin capsules with the mixture.

| Ingredient | Amount per capsule (mg) |
|---|---|
| $N^2$-(3-cyclohexyl-4-methoxy-phenylsulfonyl)-L-arginyl-N-butylglycine | 250 |
| Lactose | 250 |
| Total | 500 mg |

EXAMPLE 7

Sterile solution for infusion

The following ingredients are dissolved in water for intravenous perfusion and the resulting solution is then sterilized.

| Ingredients | Amount (g) |
|---|---|
| $N^2$-(3-cyclohexyl-4-methoxy-phenylsulfonyl)-L-arginyl-N-butylglycine | 25 |
| Buffer system | As desired |
| Glucose | 25 |
| Distilled water | 500 |

PREPARATION A

Arylsulfonyl chlorides (A) Sodium 6,7-dimethoxy-2-naphthalenesulfonate

To a well stirred solution of 70.8 g of sodium 6,7-dihydroxy-2-naphthalenesulfonate and 77.2 g of sodium hydroxide in 450 ml of water was added dropwise 230 ml of dimethyl sulfate at 60° C over a period of 1 hour, during which time the product precipitated. To this reaction mixture was added in portions 38.8 g of sodium hydroxide, and stirring was continued for one hour. After one hour at room temperature, the precipitate was filtered, washed with ethanol and dried to give 50 g of sodium 6,7-dimethoxy-2-naphthalenesulfonate.

(B) 6,7-dimethoxy-2-naphthalenesulfonyl chloride

To a stirred suspension of 50 g of finely divided sodium 6,7-dimethoxy-2-naphthalenesulfonate in 100 ml of dimethylformamide was added dropwise 62.2 ml of thionyl chloride at room temperature. After 30 minutes, the reaction mixture was poured into 1 l of ice water, and the precipitate filtered and then dissolved into 250 ml of benzene. The benzene solution was repeatedly washed with water and dried over anhydrous sodium sulfate. The solvent was evaporated to dryness in vacuo, and the residue was recrystallized from benzene-n-hexane (1:1) to give 32 g of 6,7-dimethoxy-2-naphthalenesulfonyl chloride, M.P. 127.5°–129.5° C Analysis - Calcd. for $C_{12}H_{11}O_4SCl$ (percent): C, 50.26; H, 3.87; Cl, 12.37 Found (percent): C, 50.45; H, 4.00; Cl, 12.33

The following arylsulfonyl chlorides not previously reported in the chemical literature were synthesized by the aforementioned procedure which is essentially that as described in E. H. Rodd, "Chemistry of Carbon Compounds", Elsevier Publishing Company, 1954, Vol III, P. 441–469.

| No. | Arylsulfonyl Chloride | M.P. (° C) |
|---|---|---|
| 1 | 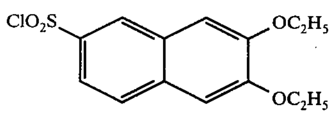 | 118 - 119.5 |
| 2 | 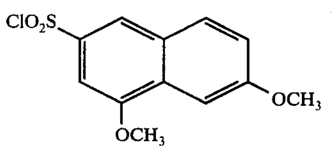 | 136.5 - 138.5 |
| 3 | 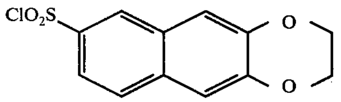 | 137 - 139 |

PREPARATION B

Amino acid derivatives (A) N-butylglycine tert-butyl ester

To 36.5 g of butylamine was added with stirring 15.05 g of tert-butyl chloroacetate over a period of 30 minutes, while maintaining the temperature at 30°–70° C. The reaction mixture was held at 70° C for an additional one hour. At the end of this period, the excess butyl amine was evaporated in vacuo, and the residue was taken up in 40 ml of 2N NaOH solution and 50 ml of benzene, transferred into a separatory funnel and well shaken. The benzene solution was separated, washed with water, dried over anhydrous sodium sulfate and filtered. After evaporation of benzene, the residue was distilled under reduced pressure to give 17.0 g (90.9 percent) of N-butylglycine tert-butyl ester, B.P. 76° C/4 mmHg.

The following amino acid tert-butyl esters not previously reported in the chemical literature were synthesized by the aforementioned procedure which is essentially that as taught by A. J. Speziale et al., J. Org. Chem. 25, 731 (1960).

| No. | Amino Acid Derivative | B.P. |
|---|---|---|
| 1 | 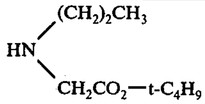 | 95° C/20 mmHg |
| 2 | 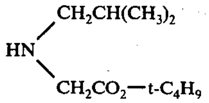 | 65° C/5 mmHg |
| 3 | 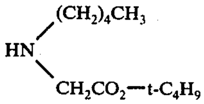 | 89 - 90° C/2.5 mmHg |
| 4 | 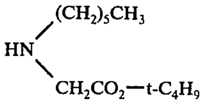 | 83 - 5° C/1.5 mmHg |
| 5 | 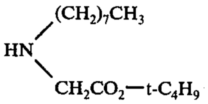 | 125 - 130° C/4 mmHg |
| 6 | 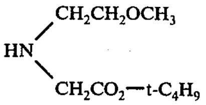 | 61 - 2° C/2 mmHg |
| 7 | 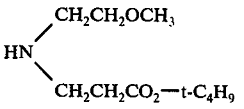 | 94° C/3 mmHg |
| 8 | 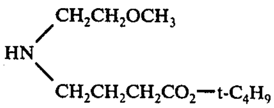 | 60 - 3° C/3 mmHg |
| 9 | 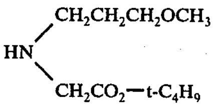 | 95 - 7° C/5 mmHg |

-continued
| No. | Amino Acid Derivative | B.P. |
|---|---|---|
| 10 | 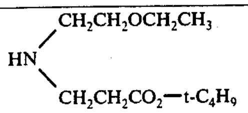 | 102° C/4 mmHg |
| 11 | 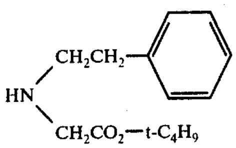 | 166° C/10 mmHg |
| 12 | 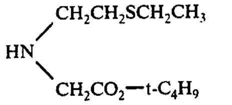 | 106 - 9° C/1.5 mmHg |
| 13 | 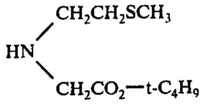 | 97° C/2.5 mmHg |
| 14 | 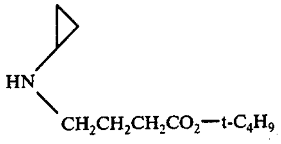 | 101° C/5 mmHg |
| 15 | 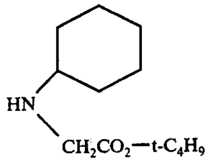 | 101° C/5 mmHg |
| 16 | 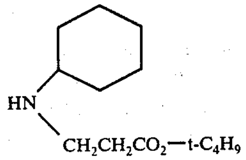 | 105° C/4 mmHg |
| 17 | 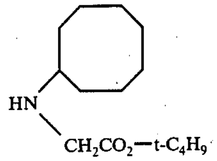 | 129 - 130° C/8 mmHg |
| 18 | 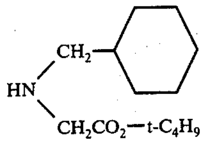 | 145° C/15 mmHg |
| 19 | 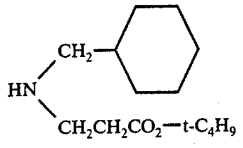 | 156° C/10 mmHg |
| 20 | 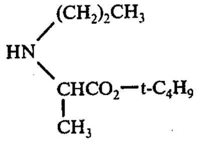 | 93° C/26 mmHg |
-continued
| No. | Amino Acid Derivative | B.P. |
|---|---|---|
| 21 | 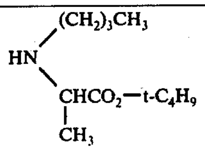 | 110° C/27 mmHg |
| 22 | 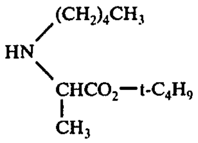 | 124° C/26 mmHg |
| 23 | 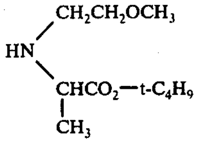 | 88 - 90° C/6 mmHg |
| 24 | 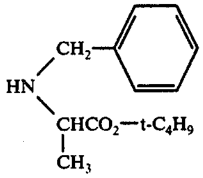 | 116 - 8° C/2 mmHg |
| 25 | 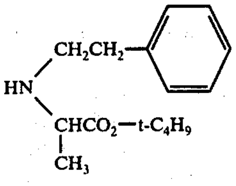 | 167° C/16 mmHg |
| 26 | 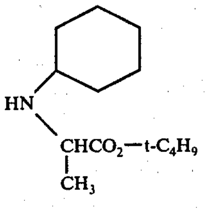 | 125° C/16 mmHg |
| 27 | 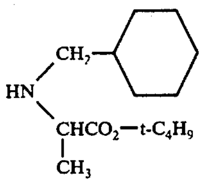 | 141° C/15 mmHg |
| 28 | 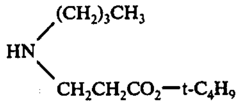 | 89° C/3 mmHg |
| 29 | 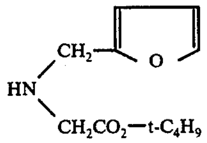 | 111° C/1 mmHg |
| 30 | 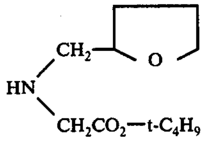 | 91 - 2° C/1 mmHg |

-continued

| No. | Amino Acid Derivative | B.P. |
|---|---|---|
| 31 | 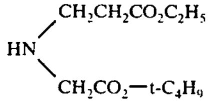 | 115° C/2 mmHg |
| 32 | 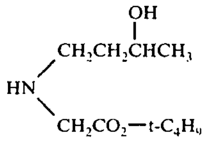 | 82 - 84° C/2 mmHg |
| 33 | 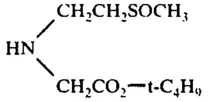 | 150° C/0.5 mmHg |
| 34 | 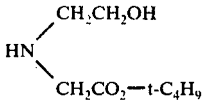 | 95 - 6° C/2 mmHg |
| 35 | 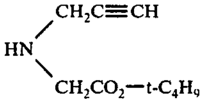 | |

(B) N-(2-methoxyethyl)glycine ethyl ester

To a stirred solution of 165.2 g of 2-methoxyethylamine and 202.4 g of triethylamine in 1 l of benzene was added dropwise a solution of 334.0 g of ethyl bromoacetate in 200 ml of benzene in one hour at room temperature. At the end of this period, the mixture was heated at reflux for 2 hours to complete the reaction. Upon chilling, the triethylamine hydrobromide was removed by filtration and washed with benzene. After removal of the solvent, the product was distilled in vacuo to yield 242.8 g (75.3 percent) of N-(2-methoxyethyl)glycine ethyl ester, B.P. 73°-5° C/4 mmHg.

The following amino acid ethyl esters not previously reported in the chemical literature were synthesized by the aforementioned procedure which is essentially that as taught by A. J. Speziale et al., J. Org. Chem., 25 731 (1960).

| No. | Amino Acid Ethyl Ester | M.P. (° C) or B.P. (° C/mmHg) |
|---|---|---|
| 1 | 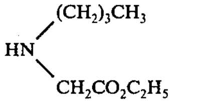 | 57 - 8° C/3 mmHg |
| 2 | 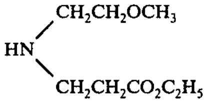 | 63 - 4° C/3 mmHg |
| 3 | 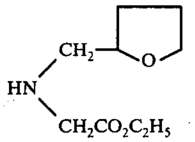 | 91 - 3° C/2 mmHg |
| 4 | 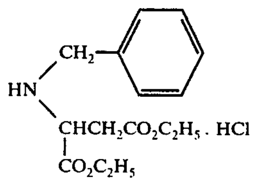 | 101 - 2° C |
| 5 | 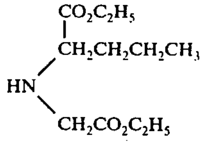 | 113 - 6° C/3 mmHg |
| 6 | 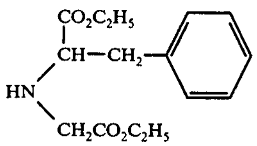 | 116 - 7° C/1 mmHg |
| 7 | 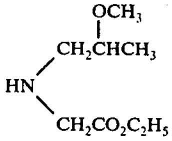 | 78 - 80° C/2 mmHg |
| 8 | 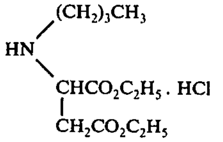 | 63 - 4° C |

(C) N-(2-methoxyethyl)glycine benzyl ester p-toluenesulfonate

To a solution of 55.8 g of N-(2-methoxyethyl)glycine tert-butyl ester in 200 ml of benzene was added 63.8 g of benzyl alcohol and 72.9 g of p-toluenesulfonic acid monohydrate. The mixture was heated at reflux for 10 hours with the continuous removal of water through a Dean-Stark water trap. At the end of this period, the solution was concentrated in vacuo, and to the residue was added 300 ml of dry ethyl ether. After 2 hours at room temperature, the formed precipitate was filtered, washed with dry ethyl ether and then recrystallized from ethyl acetate to yield 99.2 g (85 percent) of N-(2-methoxyethyl)glycine benzyl ester p-toluenesulfonate, M.P. 95°-6° C.

The following amino acid benzyl ester p-toluenesulfonate not previously reported in the chemical literature were synthesized by the aforementioned procedure.

| No. | Amino Acid Benzyl Ester p-Toluenesulfonate | M.P. (° C) |
|---|---|---|
| 1 | 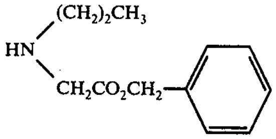 | 97 - 9 |
| 2 | 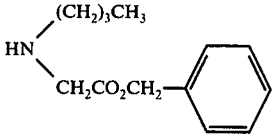 | 122 - 4 |

-continued

| No. | Amino Acid Benzyl Ester p-Toluenesulfonate | M.P. (° C) |
|---|---|---|
| 3 | 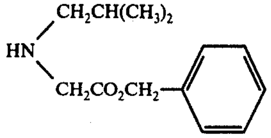 | 94 - 5 |
| 4 | 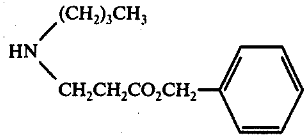 | 66 - 8 |
| 5 | 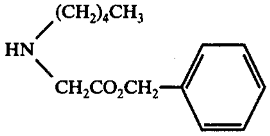 | 101 - 2 |
| 6 | 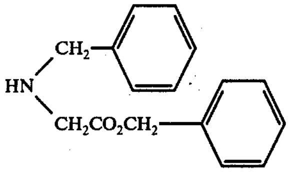 | 140 - 3 |
| 7 | 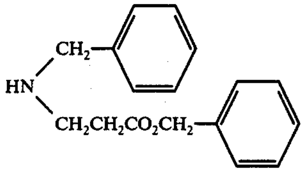 | 154 - 6 |
| 8 | 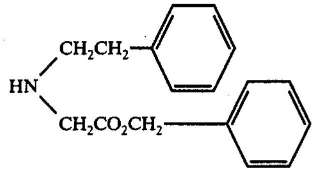 | 133 - 5 |
| 9 | 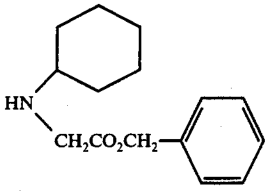 | 133 - 5 |
| 10 | 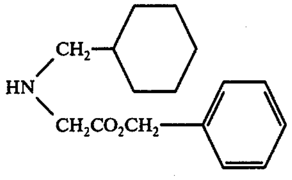 | 133 - 8 |
| 11 | 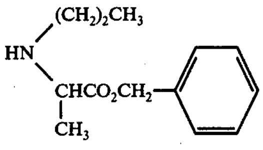 | 103 - 6 |
| 12 | 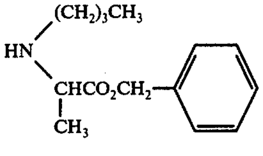 | 92 - 4 |

-continued

| No. | Amino Acid Benzyl Ester p-Toluenesulfonate | M.P. (° C) |
|---|---|---|
| 13 | 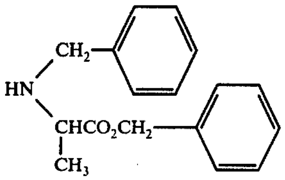 | 123 - 6 |
| 14 | 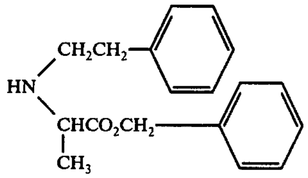 | 119 - 123 |

Having now fully described the invention, it will be apparent to one of ordinary skill in the art that many changes and modifications can be made thereto without departing from the spirit of the invention as set forth herein.

What is claimed as new and desired to be secured by Letters Patent of the United States is:

1. An $N^2$-arylsulfonyl-L-argininamide having the formula (I)

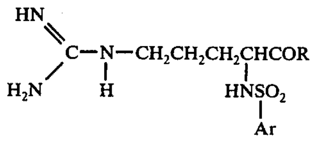
(I)

or a pharmaceutically acceptable salt thereof, wherein R is

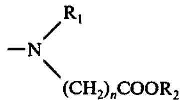
(I)

wherein $R_1$ is $C_2$–$C_{10}$ alkyl, $C_3$–$C_{10}$ alkenyl, $C_3$–$C_{10}$ alkynyl, $C_2$–$C_{10}$ alkoxyalkyl, $C_2$–$C_{10}$ alkylthioalkyl, $C_2$–$C_{10}$ alkylsulfinylalkyl, $C_1$–$C_{10}$ hydroxyalkyl, $C_2$–$C_{10}$ carboxyalkyl, $C_3$–$C_{10}$ alkoxycarbonylalkyl, $C_1$–$C_{10}$ haloalkyl, $C_7$–$C_{15}$ aralkyl, $C_8$–$C_{15}$ $\alpha$-carboxyaralkyl, $C_3$–$C_{10}$ cycloalkyl or $C_4$–$C_{10}$ cycloalkyl; $R_2$ is hydrogen, $C_1$–$C_{10}$ alkyl, $C_6$–$C_{10}$ aryl, $C_7$–$C_{12}$ aralkyl or 5-indanyl; and $n$ is an integer of 1,2 or 3; or

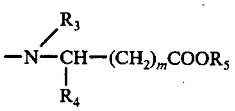
(2)

wherein $R_3$ is hydrogen, $C_1$–$C_{10}$ alkyl, $C_3$–$C_{10}$ alkenyl, $C_3$–$C_{10}$ alkynyl, $C_2$–$C_{10}$ alkoxyalkyl, $C_2$–$C_{10}$ alkylthioalkyl, $C_2$–$C_{10}$ alkylsulfinylalkyl, $C_1$–$C_{10}$ hydroxyalkyl $C_2$–$C_{10}$ carboxyalkyl, $C_3$–$C_{10}$ alkoxycarbonylalkyl, $C_1$–$C_{10}$ haloalkyl, $C_7$–$C_{15}$ aralkyl, $C_8$–$C_{15}$$\alpha$-carboxyaralkyl, $C_3$–$C_{10}$ cycloalkyl or $C_4$–$C_{10}$ cycloalkylalkyl; $R_4$ is $C_1$–$C_5$ alkyl, carboxy, $C_2$–$C_{10}$ alkoxycarbonyl, phenyl, $C_7$–$C_{12}$ aralkyl or ring substituted benzyl wherein said substituent is $C_1$–$C_5$ alkyl or $C_1$–$C_5$ alkoxy; $R_5$ is hydrogen, $C_1$–$C_{10}$ alkyl, $C_6$–$C_{10}$ aryl, $C_7$–$C_{12}$ aralkyl or 5-indanyl; and *m* is an integer of 0, 1 or 2;

Ar is a phenyl or naphthyl group, either substituted with at least one substituent selected from the group consisting of sulfoamino, carbamoyl, $C_3$–$C_{10}$ N,N-dialkylcarbamonyl, amino, $C_1$–$C_{10}$ alkylamino, mercapto, $C_1$–$C_{10}$ alkylthio, $C_7$ –$C_{12}$ aralkyl, carboxy, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl and phenyl optionally substituted with at least one hydroxy, $C_1$–$C_5$ alkoxy, or mixtures thereof;

a phenyl or naphthyl group, either substituted with at least one substituent selected from the group consisting of sulfoamino, carbamoyl, $C_3$–$C_{10}$N,N-dialkylcarbamonyl, amino, $C_1$–$C_{10}$ alkylamino, mercapto, $C_1$–$C_{10}$ alkylthio, $C_7$–$C_{12}$ aralkyl, carboxy, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl and phenyl optionally substituted with at least one hydroxy, $C_1$–$C_5$ alkoxy, or mixutres thereof, and at least one substituent selected from the group consisting of halo, nitro, cyano, hydroxy, $C_1$–$C_{10}$ alkyl, $C_1$–$C_{10}$ alkoxy and $C_2$–$C_{20}$ dialkylamino;

an oxanthrenyl or dibenzofuranyl group substituted with at least one substituent selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl, and phenyl optionally substituted with at least one hydroxy, $C_1$–$C_5$ alkoxy, or mixtures thereof;

a $C_7$–$C_{12}$ aralkyl, tetrahydronaphthyl, 1,2-ethylenedioxyphenyl, chromanyl, 2,3-ethylenedioxynaphthyl or xanthenyl group, any substituted with at least one substituent selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino, carbamoyl, $C_3$–$C_{10}$ N,N-dialkylcarbamonyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl, oxo and phenyl optionally substituted with at least one hydroxy, $C_1$–$C_5$ alkoxy, or mixtures thereof; a naphthoquinonyl, anthryl, phenanthryl, pentalenyl, heptalenyl, azulenyl, biphenylenyl, as-indacenyl, S-indacenyl, acenaphthylenyl, phenylcarbonylphenyl, phenoxyphenyl, benzofuranyl, isobenzofuranyl, benzo (b) thienyl, isobenzothienyl, thianthrenyl, dibenzothienyl, phenoxathiinyl, indolyl, 1H-indazolyl, quinolyl, isoquinolyl, phthalazinyl, 1,8-naphthridinyl, quinoxalinyl, quinazolinyl, cinnolinyl, carbazolyl, acridinyl, phenazinyl, phenothiazinyl, phenoxazinyl or benzimidazolyl group any of which is unsubstituted or substituted with one or more groups selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino, carbamoyl $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$ hydroxyalkyl, $C_1$–$C_{10}$ haloalkyl and phenyl optionally substituted with at least one hydroxy, $C_1$–$C_5$ alkoxy, or mixtures thereof;

a $C_9$–$C_{16}$ cycloalkylphenyl, $C_{10}$–$C_{18}$ cycloalkylalkylphenyl, $C_9$–$C_{16}$ cycloalkyloxyphenyl, $C_9$–$C_{16}$ cycloalkylthiophenyl, 9,10-dihydroanthryl, 5,6,7,8-tetrahydroanthryl, 9,10-dihydrophenanthryl, 1,2,3,4,5,6,7,8-octahydrophenanthryl, indenyl, indanyl, fluorenyl, acenaphthenyl, phenylthiophenyl, isochromanyl, 2,3-dihydrobenzofuranyl, 1,3-dihydroisobenzofuranyl, thioxanthenyl, 2H-chromenyl, 3,4-dehydro-1-isochromanyl, 4H-chromenyl, indolinyl, isoindolinyl, 1,2, 3,4-tetrahydroquinolyl or 1,2,3,4-tetrahydroisoquinolyl group any of which is unsubstituted or substituted with one or more groups selected from the group consisting of halo, nitro, cyano, hydroxy, $C_1$–$C_{10}$ alkyl, $C_1$–$C_{10}$ alkoxy, $C_2$–$C_{20}$ dialkylamino, sulfoamino, carbamoyl, $C_3$–$C_{10}$ N,N-dialkylcarbamoyl, amino, $C_1$–$C_{10}$ alkylamino, mercapto, $C_1$–$C_{10}$ alkylthio, $C_7$–$C_{12}$ aralkyl, carboxyl, $C_2$–$C_{10}$ alkoxycarbonyl, $C_2$–$C_{10}$ carboxyalkyl, $C_1$–$C_{10}$ acylamino, $C_2$–$C_{10}$ alkylcarbonyl, $C_1$–$C_{10}$hydroxyalkyl, $C_1$–$C_{10}$ haloalkyl, oxo and phenyl optionally substituted with at least one hydroxyl, $C_1$–$C_5$ alkoxy, or mixtures thereof; or benzene ring-substituted

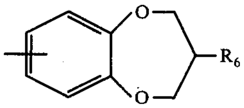

wherein $R_6$ is hydrogen, $C_1$–$C_{10}$ alkyl or $C_1$–$C_{10}$ alkoxy, and said substituent is at least one $C_1$–$C_5$ alkoxy or mixtures thereof.

2. The compound of claim 1 wherein said Ar group is substituted with at least one $C_1$–$C_5$ alkoxy, $C_1$–$C_5$ alkyl group or mixtures thereof.

3. A method of inhibiting activity and suppressing activation of thrombin in vivo which comprises administering a mammal pharmaceutically effective amount of a compound of claim 1.

* * * * *